(12) United States Patent
Veliss et al.

(10) Patent No.: US 11,077,272 B2
(45) Date of Patent: *Aug. 3, 2021

(54) RESPIRATORY MASK

(71) Applicant: ResMed Pty Ltd, Bella Vista (AU)

(72) Inventors: Lee James Veliss, Rotterdam (NL); Carmel Theresa Harrington, Sydney (AU); Philip Rodney Kwok, Sydney (AU); Philip John Gunning, Sydney (AU); Joshua Adam Gudiksen, Sydney (AU); Bart Jeremy Caffin, Sydney (AU); Richard Sokolov, Sydney (AU); Ian Frederick Johnson, Sydney (AU); Eric Siu, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 286 days.

This patent is subject to a terminal disclaimer.

(21) Appl. No.: 15/961,138

(22) Filed: Apr. 24, 2018

(65) Prior Publication Data

US 2018/0236198 A1    Aug. 23, 2018

Related U.S. Application Data

(63) Continuation of application No. 12/377,801, filed as application No. PCT/AU2008/000270 on Feb. 29, 2008, now Pat. No. 9,981,102.
(Continued)

(30) Foreign Application Priority Data

Mar. 2, 2007    (AU) ................................ 2007901078
Feb. 29, 2008   (WO) ................. PCT/AU2008/000270

(51) Int. Cl.
*A61M 16/06*     (2006.01)
*A61M 16/08*     (2006.01)

(52) U.S. Cl.
CPC ........ *A61M 16/06* (2013.01); *A61M 16/0616* (2014.02); *A61M 16/0622* (2014.02);
(Continued)

(58) Field of Classification Search
CPC ........ A61M 16/00; A61M 16/06–0694; A61M 16/20–209; A61M 16/0003–0012;
(Continued)

(56) References Cited

U.S. PATENT DOCUMENTS 428,592 A     5/1890  Chapman
1,206,045 A   11/1916 Smith
(Continued)

FOREIGN PATENT DOCUMENTS

NZ    526168    10/2004
NZ    539836     5/2007
(Continued)

OTHER PUBLICATIONS

Partial European Search Report dated Sep. 6, 2019 issued in European Application No. 19179877.6 (15 pages).
(Continued)

*Primary Examiner* — Jan Christopher L Merene
*Assistant Examiner* — Ned T Heffner
(74) *Attorney, Agent, or Firm* — Nixon & Vanderhye P.C.

(57) ABSTRACT

A respiratory mask for use with a patient, and that is suited for use with children, includes a flexible cushion arranged to interface with and deliver air to the patient's nose. The cushion has a tube connection portion at one or both sides adjacent the patient's nares, the tube connection portion being arranged to connect to an air delivery tube. This location, plus the very low profile of the mask, allows a patient (e.g. an infant) to sleep on their face more comfortably. A more rigid support structure adjacent the cushion is provided to stabilize the cushion and prevent it from col-
(Continued)

lapsing. Headgear is also provided and arranged for releasable attachment to the support structure.

42 Claims, 45 Drawing Sheets

Related U.S. Application Data

(60) Provisional application No. 61/025,427, filed on Feb. 1, 2008, provisional application No. 60/947,509, filed on Jul. 2, 2007.

(52) U.S. Cl.
CPC .... *A61M 16/0683* (2013.01); *A61M 16/0825* (2014.02); *A61M 16/0816* (2013.01); *A61M 2210/0618* (2013.01)

(58) Field of Classification Search
CPC . A61M 2016/0015–0042; B63C 11/12; B63C 11/18; A62B 7/00; A62B 7/04; A62B 7/14; A62B 18/00; A62B 18/10
See application file for complete search history.

(56) References Cited

U.S. PATENT DOCUMENTS

| | | | |
|---|---|---|---|
| 1,395,948 A | 11/1921 | Bernhard | |
| 1,632,449 A | 6/1927 | McKesson | |
| 2,023,267 A | 12/1935 | De Saint et al. | |
| 2,104,016 A * | 1/1938 | Biggs | A62B 18/025 |
| | | | 128/206.24 |
| 2,241,535 A | 5/1941 | Boothby | |
| 2,290,885 A | 7/1942 | Lehmberg | |
| 2,348,277 A | 5/1944 | Boothby et al. | |
| 2,625,155 A | 1/1953 | Engelder | |
| 3,667,475 A | 6/1972 | Venturelli et al. | |
| 3,828,773 A | 8/1974 | Buch et al. | |
| 4,015,598 A | 5/1977 | Brown | |
| 4,219,020 A | 8/1980 | Czajka | |
| 4,265,239 A | 5/1981 | Fischer, Jr. et al. | |
| 4,354,488 A | 10/1982 | Bartos | |
| 4,449,526 A | 5/1984 | Elam | |
| 4,459,983 A | 7/1984 | Beyreuther et al. | |
| 4,590,951 A | 5/1986 | O'Connor | |
| 4,603,692 A * | 8/1986 | Montesi | A62B 18/084 |
| | | | 128/207.11 |
| 4,751,924 A | 6/1988 | Hammerschmidt et al. | |
| 4,770,169 A | 9/1988 | Schmoegner et al. | |
| 4,782,832 A | 11/1988 | Trimble et al. | |
| 4,803,981 A | 2/1989 | Vickery | |
| 5,018,519 A | 5/1991 | Brown | |
| 5,086,769 A | 2/1992 | Niemeyer | |
| 5,109,839 A | 5/1992 | Blasdell et al. | |
| 5,269,296 A | 12/1993 | Landis | |
| 5,662,101 A | 9/1997 | Ogden et al. | |
| 5,711,296 A | 1/1998 | Kolobow | |
| 5,722,392 A | 3/1998 | Skimming et al. | |
| 6,019,101 A | 2/2000 | Cotner et al. | |
| 6,374,826 B1 | 4/2002 | Gunaratnam et al. | |
| 6,418,928 B1 | 7/2002 | Bordewick et al. | |
| 6,457,472 B1 | 10/2002 | Schwartz | |
| 6,595,215 B2 | 7/2003 | Wood | |
| 6,631,718 B1 * | 10/2003 | Lovell | A61M 16/06 |
| | | | 128/206.24 |
| 6,851,428 B2 | 2/2005 | Dennis | |
| 6,996,857 B2 | 2/2006 | Fukasawa | |
| 7,827,990 B1 | 11/2010 | Melidis et al. | |
| 9,981,102 B2 * | 5/2018 | Veliss | A61M 16/0683 |
| 2002/0059935 A1 | 5/2002 | Wood | |
| 2003/0116160 A1 | 6/2003 | Kwok | |
| 2003/0154978 A1 | 8/2003 | Gradon et al. | |
| 2003/0154980 A1 | 8/2003 | Berthon-Jones et al. | |
| 2003/0183227 A1 | 10/2003 | Klemperer | |
| 2003/0196656 A1 | 10/2003 | Moore et al. | |
| 2003/0221691 A1 | 12/2003 | Biener et al. | |
| 2004/0045550 A1 | 3/2004 | Lang | |
| 2004/0226566 A1 | 11/2004 | Gunaratnam et al. | |
| 2005/0066976 A1 | 3/2005 | Wondka | |
| 2005/0199242 A1 * | 9/2005 | Matula, Jr. | A61M 16/0816 |
| | | | 128/207.13 |
| 2005/0241644 A1 | 11/2005 | Gunaratnam et al. | |
| 2006/0005840 A1 | 1/2006 | Cannon | |
| 2006/0180149 A1 | 8/2006 | Matarasso | |
| 2006/0243279 A1 | 11/2006 | Hinkle | |
| 2007/0044804 A1 | 3/2007 | Matula et al. | |
| 2010/0313891 A1 | 12/2010 | Veliss et al. | |

FOREIGN PATENT DOCUMENTS

| | | |
|---|---|---|
| WO | 96/17643 A1 | 6/1996 |
| WO | 01/32250 A1 | 5/2001 |
| WO | 01/62326 | 8/2001 |
| WO | 03/090827 A1 | 11/2003 |
| WO | 2004/032727 A2 | 4/2004 |
| WO | 2004/073777 A1 | 9/2004 |
| WO | 2004/073778 | 9/2004 |
| WO | 2005/063328 | 7/2005 |
| WO | 2005/097247 | 10/2005 |
| WO | 2007/009182 | 1/2007 |
| WO | 2007/009782 A1 | 1/2007 |
| WO | 2007/022562 | 3/2007 |
| WO | 2007/041786 A1 | 4/2007 |
| WO | 2007/045023 A1 | 4/2007 |

OTHER PUBLICATIONS

Extended European Search Report dated Jan. 13, 2020 issued in European Application No. 19179877.6 (14 pages).
First Amended Counterstatement dated Feb. 20, 2017 filed in New Zealand Application No. 615209 (32 pages).
Communication dated Nov. 16, 2016 issued in European Application No. 08706150.3 (8 pages).
Further Examination Report dated Dec. 1, 2014 issued in New Zealand Application No. 615209 (2 pages).
Further Examination Report dated May 4, 2015 issued in New Zealand Application No. 615209 (2 pages).
Further Examination Report dated Jun. 24, 2015 issued in New Zealand Application No. 615209 (2 pages).
Patent Examination Report No. 1 dated Aug. 14, 2014 in Australian Application No. 2013219139 (3 pages).
Merriam-Webster website, dictionary entry for "structure". Jul. 14, 2014. http://www.meriam-webster.com/dictionary/structure.
Extended European Search Report dated Jan. 16, 2014 in European Appln. No. EP 08706150.3 (12 pages).
Further Examination Report dated Oct. 2, 2013 in New Zealand Application No. 600517 (2 pages).
First Examination Report dated Sep. 13, 2013 in New Zealand Application No. 615209 (2 pages).
Examination Report dated Jun. 14, 2012 in New Zealand Application No. 600517 (2 pages).
Examiner's First Report dated Jun. 6, 2012 in Australian Appln. No. 2008222587 (3 pages).
International Preliminary Report on Patentability dated Sep. 8, 2009 in PCT/AU2008/000270.
International Search Report dated Jul. 30, 2008 in PCT/AU2008/000270.
Examination Report dated Feb. 16, 2011 in New Zealand Application No. 580173 (2 pages).

* cited by examiner

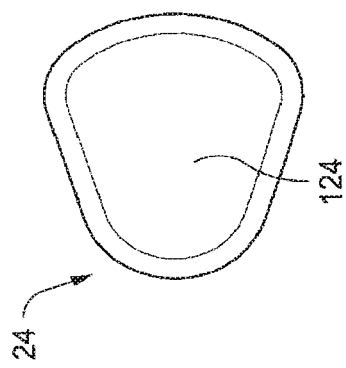
Fig. 13c
Fig. 13g
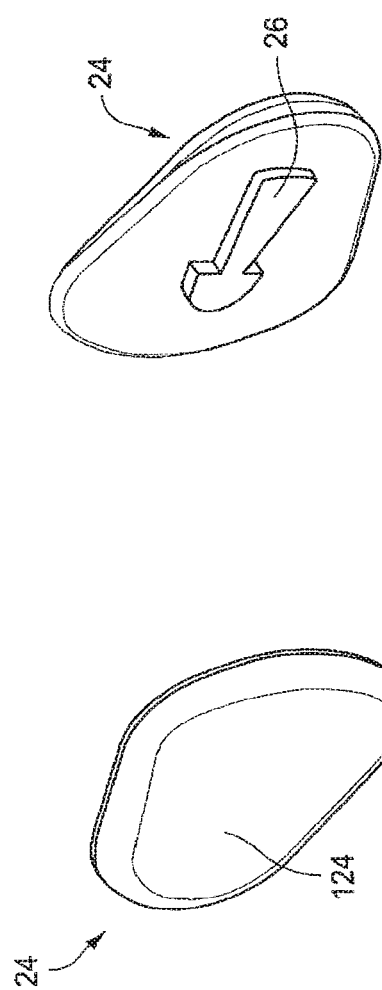
Fig. 13b
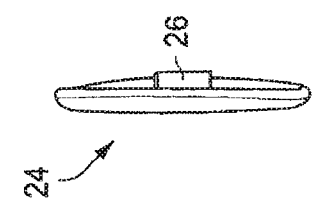
Fig. 13f
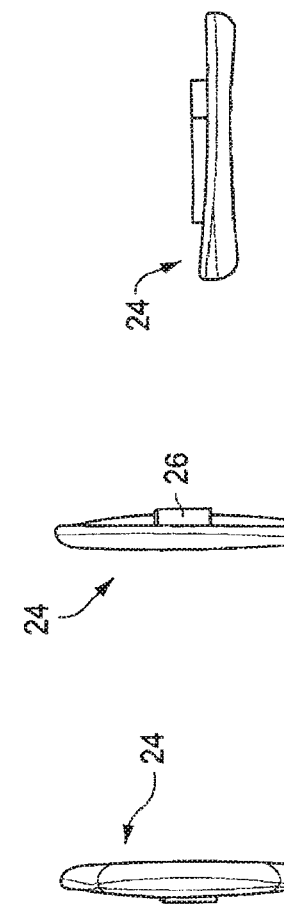
Fig. 13e
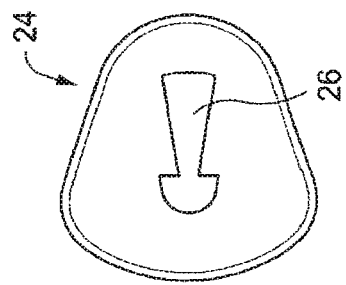
Fig. 13a
Fig. 13d

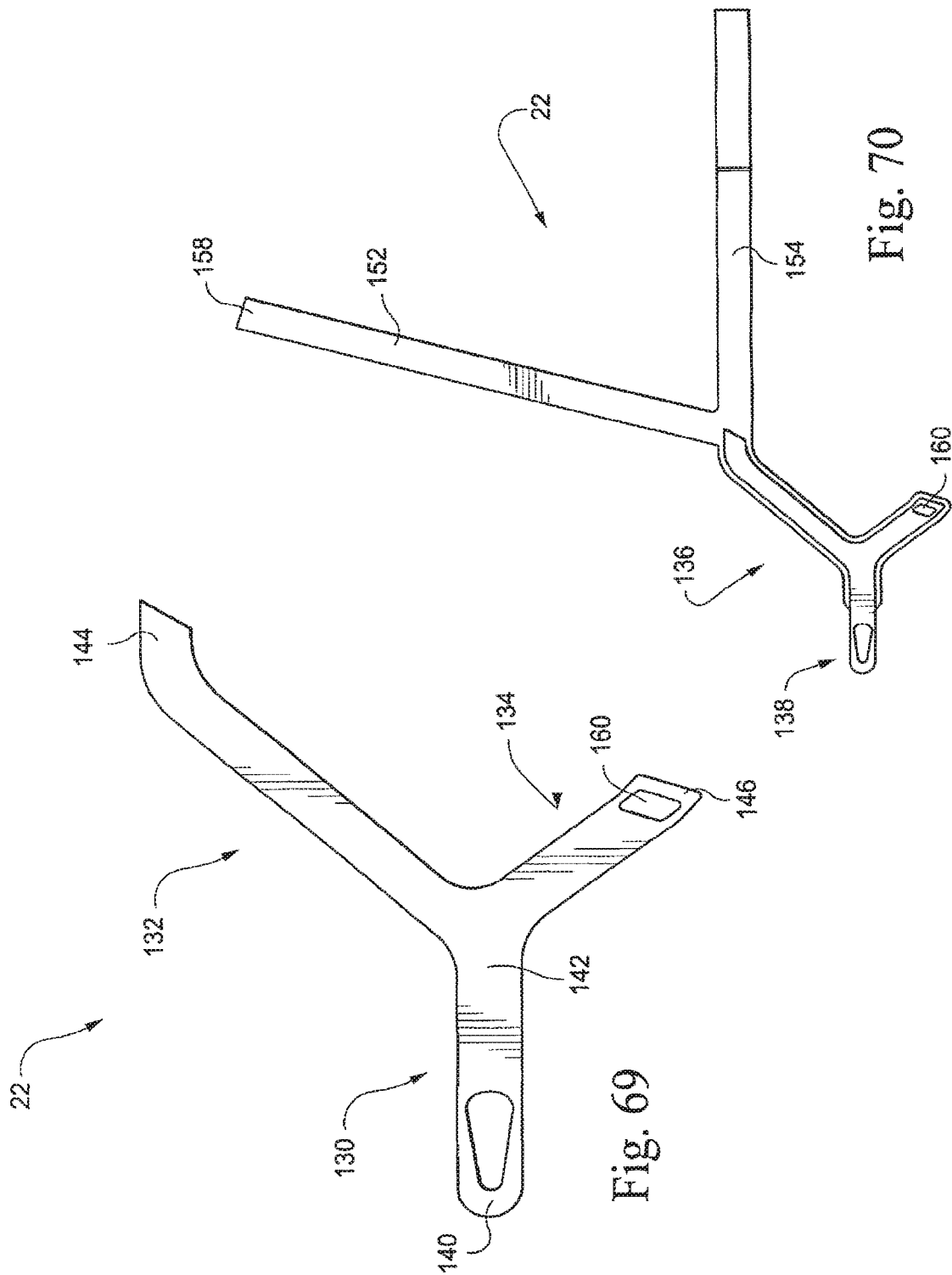

RESPIRATORY MASK

CROSS-REFERENCE TO APPLICATION

This application is the continuation of U.S. application Ser. No. 12/377,801, filed Feb. 17, 2009, now allowed, which is the U.S. national phase of International Application No. PCT/AU2008/000270, filed Feb. 29, 2008, which designated the U.S. and claims priority to Australian Provisional Application 2007901078, filed Mar. 2, 2007, and U.S. Application Nos. 60/947,509, filed Jul. 2, 2007 and 61/025,427, filed Feb. 1, 2008, each of which are incorporated herein by reference in their entirety.

The contents of PCT Application PCT/AU2004/001832, filed Dec. 24, 2004, are incorporated herein by reference in their entirety.

BACKGROUND OF THE INVENTION

The provision of a supply of air at positive pressure to the airways of a patient is well established as part of treatment of a range of respiratory conditions. Devices used for this treatment include a source of air at positive pressure, some form of air delivery conduit and some form of mask or "patient interface" as it is sometimes more generally described.

Patient interfaces, such as a nasal mask assembly, for use with Continuous Positive Airway Pressure Devices (CPAP), flow generators or blowers in the treatment of sleep disordered breathing (SDB) typically include a soft-patient contacting portion, such as a cushion, and a rigid shell or frame. In use, the patient interface is held in a sealing position by headgear so as to enable a supply of air at positive pressure to be delivered to the patient's airways.

Factors in the efficacy of therapy and compliance of patients with therapy are:
  mask comfort;
  sealing;
  stability (e.g. aids in sealing);
  fit; and
  ease of use.

Another problem encountered in the prior art is manufacturability, particularly when manufactured on a large scale.

While there are a large number of patient interfaces designed for adults, there are relatively few designed to suit infants and children. These include the ResMed Infant Bubble mask, the masks described in International Patent Applications WO/2001/032250 (Sullivan & Wilkie assigned to the Australian Centre for Advanced Medicine Technology Ltd); WO/2004/073777 (Ging, Kwok et al. assigned to ResMed Ltd); WO/2007/045023 (Kwok, Slvarajan et al., assigned to ResMed Ltd) and WO/2007/041786 (Selvarajan, Kwok et al assigned to ResMed Ltd).

Infants present a different series of challenges for the mask designer beyond simply making the mask smaller. The faces of young children are not only smaller, but a different shape to adults. Children's faces and skulls are soft and not fully formed, and there is a risk that excessive forces could lead to negative consequences. Furthermore, young children cannot articulate reasons why should they become distressed and rely on adults to fit their masks.

SUMMARY OF THE INVENTION

The present invention relates to an improved respiratory mask for use with a patient, particularly for use with infants and children. A mask in accordance with the invention provides a comfortable, unobtrusive, effective seal with the airways of a patient.

One aspect of the invention is that patients are able to sleep on their stomachs, or to roll on their faces while still using the mask. This is facilitated in part by a low profile design that has sufficient structural stability that it will not collapse. Other aspects facilitating this include reducing the size of the mask, eliminating the forehead support and placing the air delivery tube to one side of the mask to allow more of the face to contact the pillow/bed; flexible and smaller air delivery tube and decoupling of the cushion to air delivery to enable greater range of movement; allowing the cushion to flex under loading so that it is more comfortable to sleep in alternative positions; and a headgear configuration to maintain the mask in position during patient movement.

Another aspect of the invention is the generally unobtrusive nature of the mask. With their child wearing an unobtrusive mask, parents of the patient are less anxious about their child receiving respiratory therapy. Unobtrusiveness has been achieved by making the patient interface generally smaller, for example; a lower profile cushion with a streamlined supporting structure to fit the patient snugly, elimination of the forehead support, side mounted air delivery tube, small diameter air delivery tube and preferably a translucent or transparent mask. Additionally, the lack of forehead support and configuration of the headgear means that the patient's line of vision is not impeded, making the mask system look and feel unobtrusive.

Another aspect of the invention is to provide a mask with a clear vision of the patient's nares to ensure it is not blocked.

Aspects of the invention will also ensure developing tissues of the patient are not impaired or damaged by hard components. This has been achieved by soft, flexible contacting portions cushion and headgear on the patient, elimination of the forehead support, reduced size of the supporting structure when compared to frames of previous mask designs, absorption of forces due to the configuration of the cushion and preferably cheek supports.

Aspects of the invention will allow easy fitting of the mask to the patient by a third party. This has been achieved by easy release headgear attachment as minimal force and movement of the headgear is needed to disengage the support structure from the headgear, intuitive attachment due to the shape of the headgear and cushion, and efficient locking mechanism of the headgear to support structure.

Aspects of the invention will ensure the mask sealingly engages with the airways of the patient so that the respiratory therapy is effective. This has been achieved by headgear to stabilize the mask system, a cushion with a conforming membrane to engage with the patient's face, variation in the geometry of the membrane to ensure the mask seals while distributing force appropriately on the patient's face, connection of the air delivery tube to the cushion decoupling tube drag forces to maintain the seal during movement and allowed movement of the cushion with respect to the support structure so that movement of the support structure will not affect the seal of the cushion.

A further aspect of the present invention relates to a respiratory mask for use with a patient and that is particularly suited for use with children, e.g. for treatment of SDB, such as obstructive sleep apnea (OSA), or congenital abnormalities. The mask includes a flexible cushion arranged to interface with and deliver air to the patient's nose. The cushion has a tube connection portion at one or both sides adjacent the patient's nares, the tube connection portion being arranged to connect to an air delivery tube. This location, plus the very low profile of the mask, allows a patient (e.g. an infant) to sleep on their stomach more comfortably. This location also reduces destabilising moments produced by tube drag forces. A more rigid support structure adjacent the cushion is provided to stabilize the cushion and prevent it from collapsing. Headgear is also provided and arranged for releasable attachment to the support structure.

A further aspect of the present invention relates to a connection arrangement for connecting a respiratory mask to headgear. The connection arrangement includes a thin, plate-like female portion having a substantially triangular or trapezoidal aperture, and a male portion comprising a body and a cooperating substantially triangular or trapezoidal lug extending from the body, the lug having a body portion and a lip overhanging at least a portion of the body portion. The connection arrangement is such that when the lip of the lug is inserted through the aperture of the female portion and the male portion is pulled towards the apex of the aperture, an edge of the aperture locates between an under-surface of the lip and the body of the male portion to form a releasable connection. This connection is advantageous in that it is intuitive and easy for a third person (e.g. clinician or parent) to use. In a sample embodiment, both the female and male portions are relatively rigid.

A further aspect of the present invention relates to a connection portion of a respiratory mask for receiving an air delivery tube. The connection portion includes a relatively thin-walled flexible portion having an aperture configured to substantially sealingly receive an air delivery tube, and a relatively rigid surround to which the flexible portion is connected, such that when a tube is inserted into the aperture the mask is substantially decoupled from movement of the tube. Advantageously, the mask seal is not disturbed or is disturbed less by movement of the air delivery tube (e.g. tube drag).

A further aspect of the present invention provides a respiratory mask for use with a patient including a flexible cushion arranged to interface with and deliver air to the patient's nose, a more rigid support structure adjacent the cushion, and headgear arranged for releasable attachment to the support structure. The support structure extends over the patient's nasal bridge but not over the apex of the patient's nose, such that the support structure substantially stops the cushion from collapsing when a force is applied to a front side of the mask. This allows a patient to sleep on their face and still receive effective respiratory treatment.

The cushion may be translucent to the extent that the patient's nares can be inspected through the cushion, or the cushion may be substantially transparent (e.g. water clear).

A method of providing respiratory therapy is also provided by the present invention, the method including providing a mask according to any of the above aspects, connecting an air delivery conduit to the mask, connecting the air delivery conduit to a CPAP device and activating the CPAP device.

It should be noted that the word 'mask' and the word 'patient interface' are used synonymously in this specification.

An air delivery tube, for interconnection between a Continuous Positive Airway Pressure Device and a Patient Interface, may have an internal diameter of between 4 mm and 8 mm. One benefit of this sample embodiment is that it reduces the weight and/or bulk of the tube and the friction that results from movement of the tube across a surface and therefore reduces the pull (i.e., "tube drag") on the patient interface and better facilitates side, and stomach, sleeping.

BRIEF DESCRIPTION OF THE DRAWINGS

The accompanying drawings facilitate an understanding of the various embodiments of this invention. In such drawings:

FIGS. 13a-13g schematically depict views of a cheek pad of the mask of FIG. 1, and in particular FIG. 13a is a front perspective view, FIG. 13b schematically depicts a rear perspective view, FIG. 13c schematically depicts a front view, FIG. 13d schematically depicts a rear view, FIG. 13e schematically depicts a left side view, FIG. 13f schematically depicts a right side view and FIG. 13g schematically depicts a top view;

FIG. 69 schematically depicts a right one of the relatively rigid members of the headgear for the mask of FIG. 1;

FIG. 70 schematically depicts a portion of the headgear for the mask of FIG. 1 including the right relatively rigid member, upper strap and middle strap;

DETAILED DESCRIPTION

Figure 1:
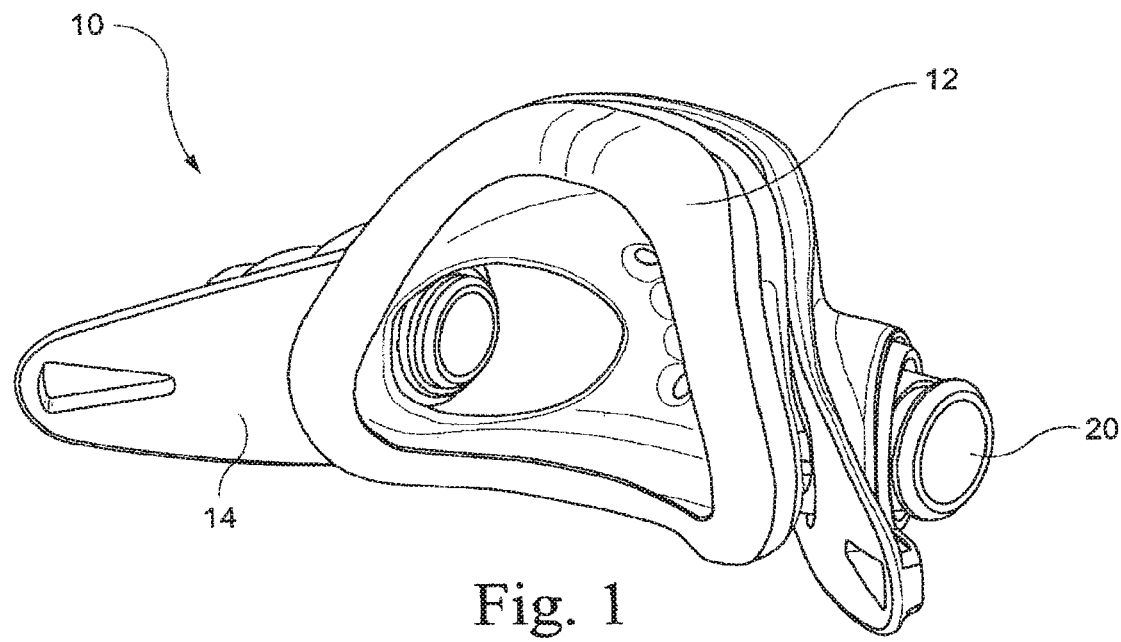
FIG. 1 schematically depicts a front perspective view of a mask without headgear according to a first embodiment of the invention.
Figure 2:
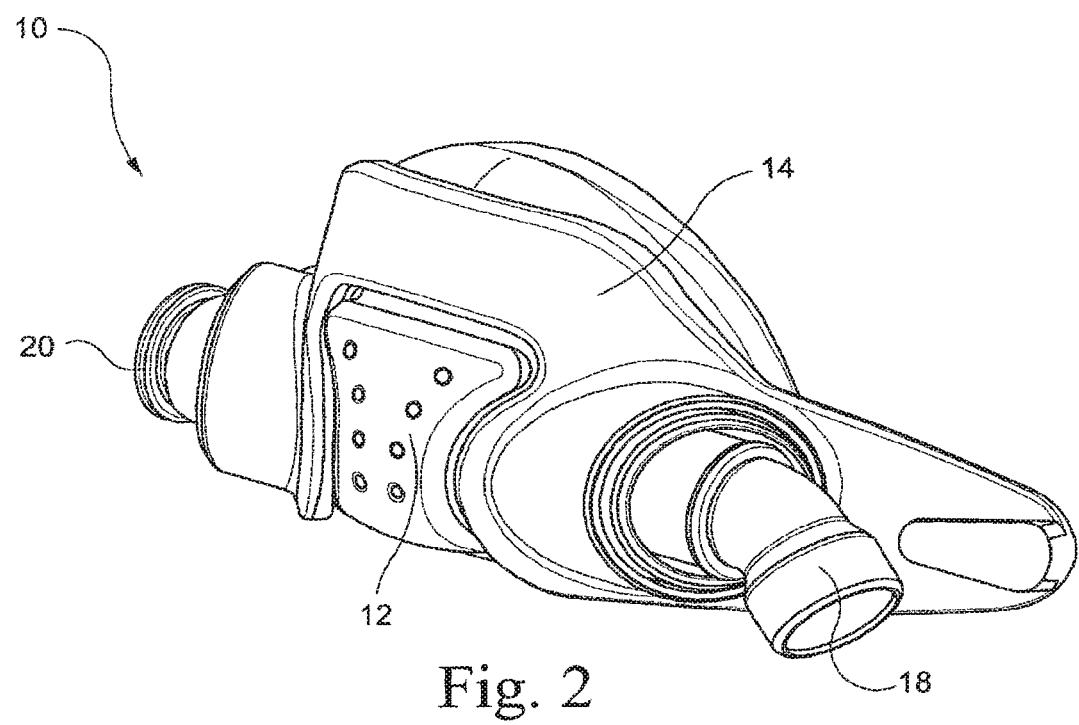
FIG. 2 schematically depicts a rear perspective view of the mask of FIG. 1.
Figure 3:
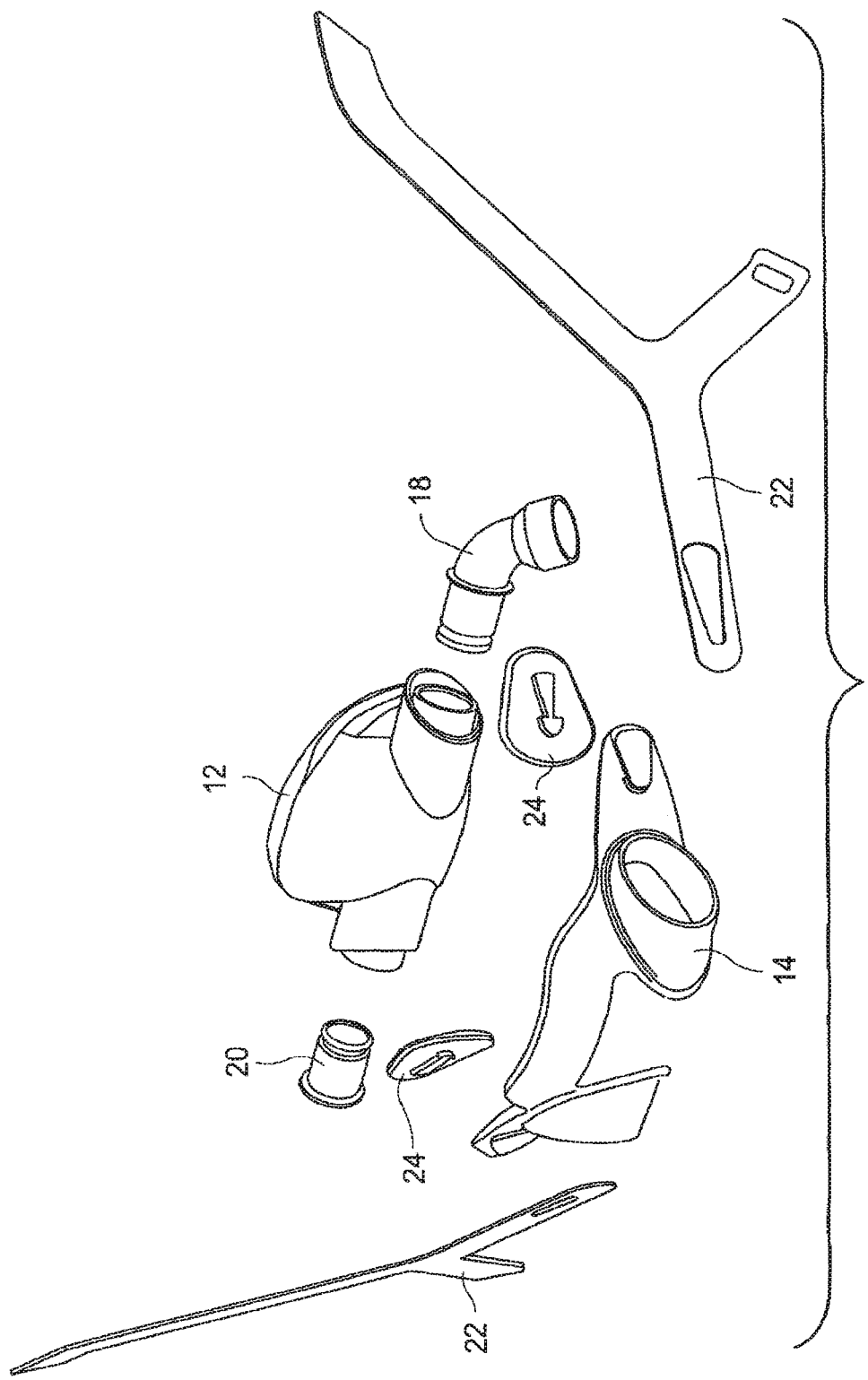
FIG. 3 schematically depicts an exploded view of the mask of FIG. 1 with relatively rigid members.
Figure 4:
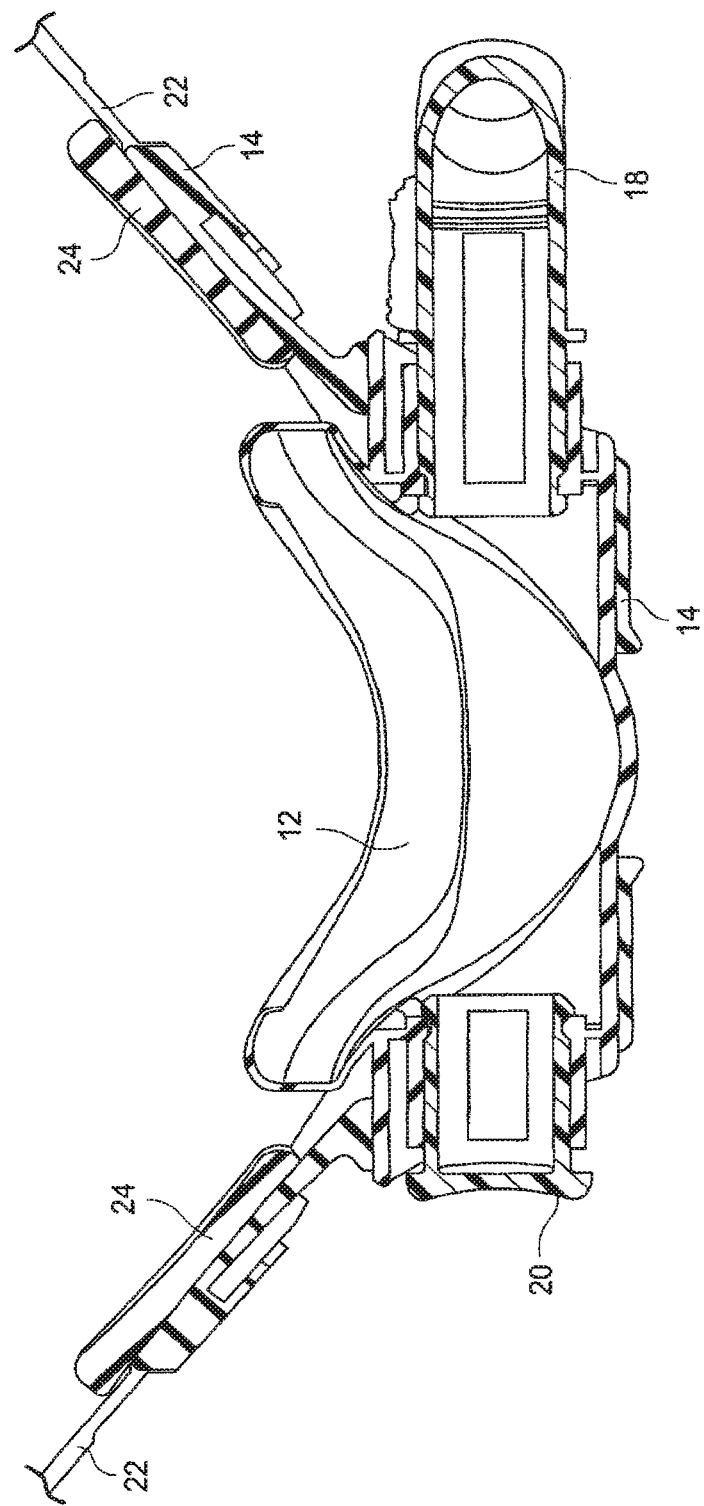
FIG. 4 schematically depicts a cross-sectional view of the mask of FIG. 1 with relatively rigid members through a lateral plane of the mask.
Figure 5:
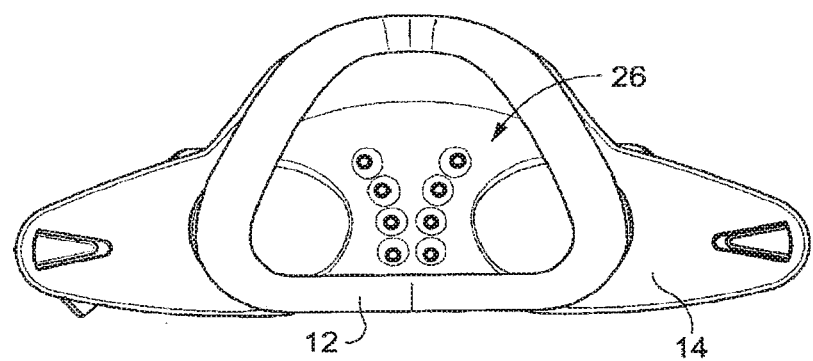
FIG. 5 schematically depicts a rear view of the mask of FIG. 1.
Figure 6:
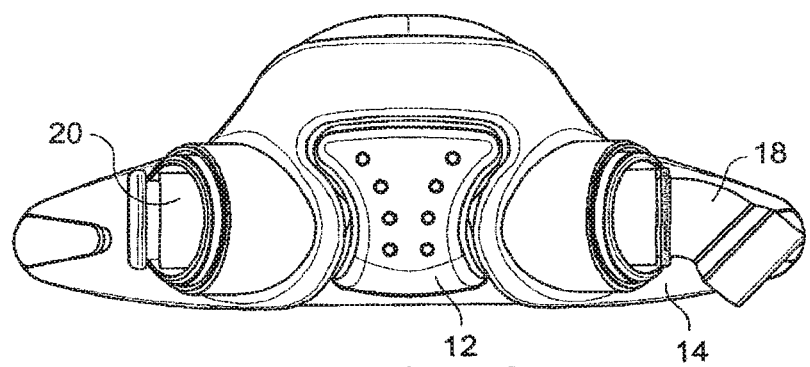
FIG. 6 schematically depicts a front view of the mask of FIG. 1.
Figure 7:
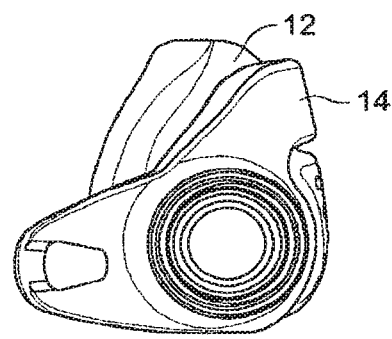
FIG. 7 schematically depicts a right side view of the mask of FIG. 1.
Figure 8:
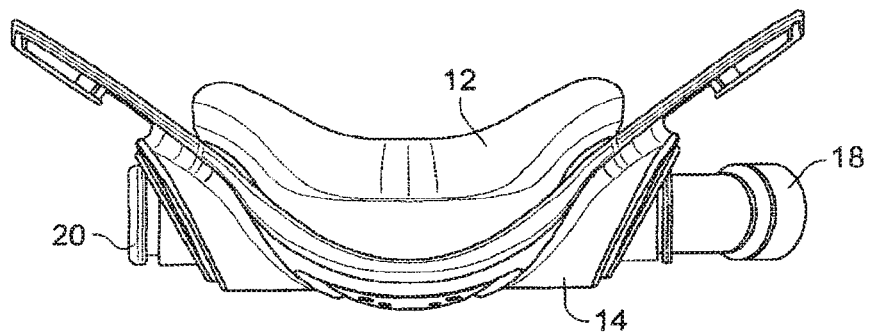
FIG. 8 schematically depicts a top view of the mask of FIG. 1.
Figure 9:
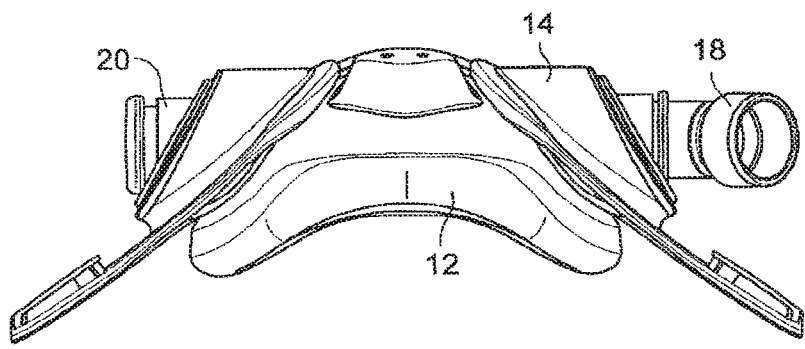
FIG. 9 schematically depicts a bottom view of the mask of FIG. 1.
Figure 10:
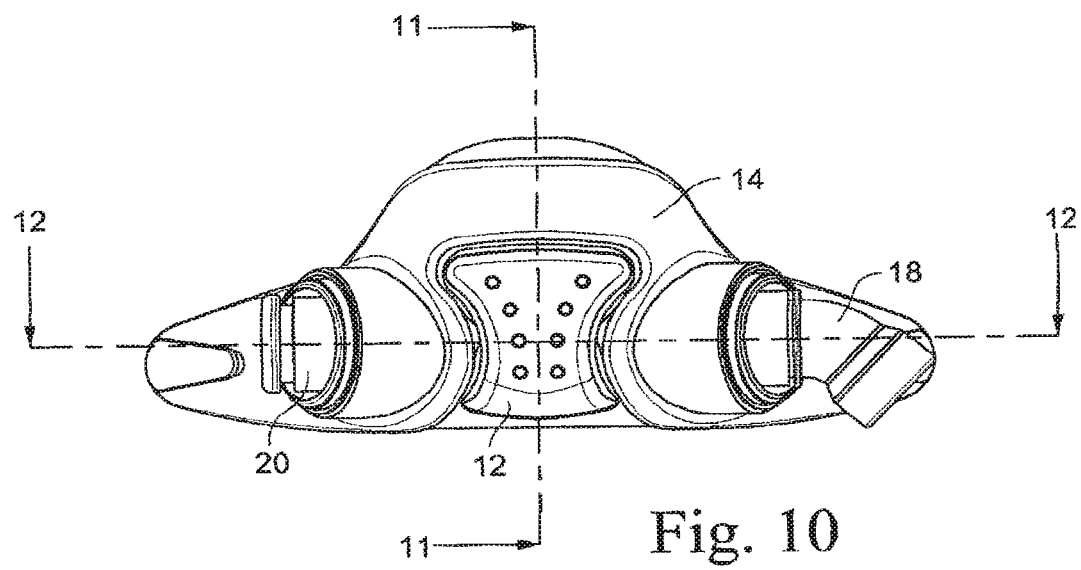
FIG. 10 schematically depicts a front view of the mask of FIG. 1.
Figure 11:
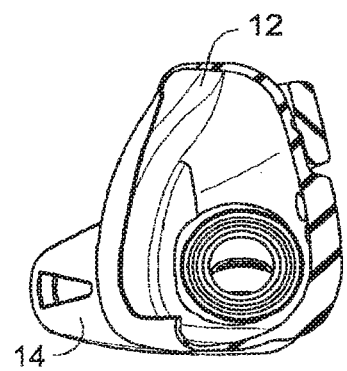
FIG. 11 schematically depicts a cross-sectional view through Section 11-11 of FIG. 10.
Figure 12:
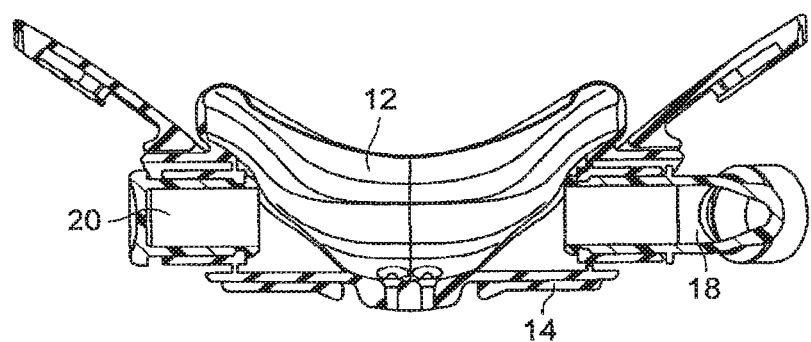
FIG. 12 schematically depicts a cross-sectional view through Section 12-12 of FIG. 10.
Figure 14:
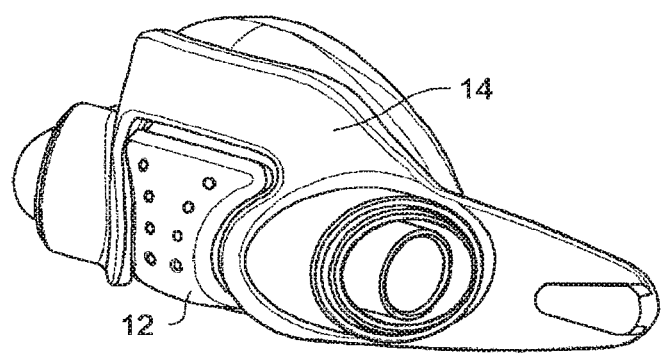
FIG. 14 schematically depicts a front perspective view of a cushion and support structure of the mask of FIG. 1.
Figure 15:
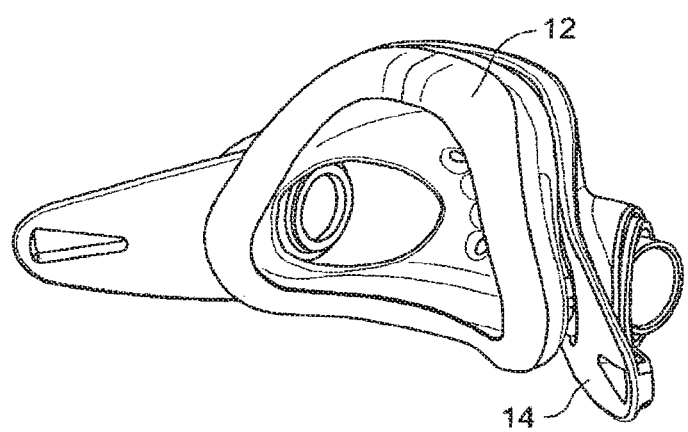
FIG. 15 schematically depicts a rear perspective view of a cushion and support structure of the mask of FIG. 1.
Figure 16:
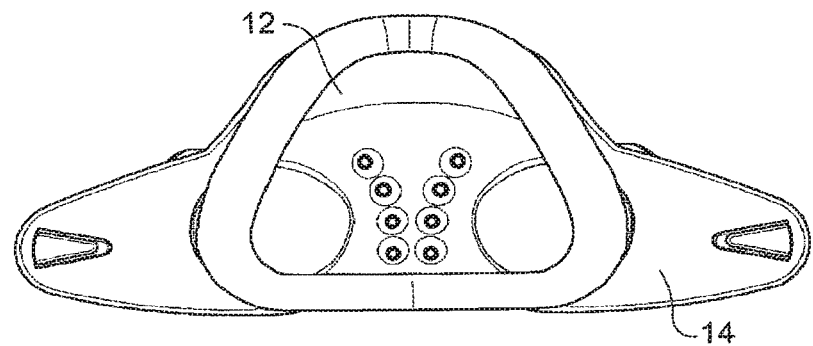
FIG. 16 schematically depicts a rear view of a cushion and support structure of the mask of FIG. 1.
Figure 17:
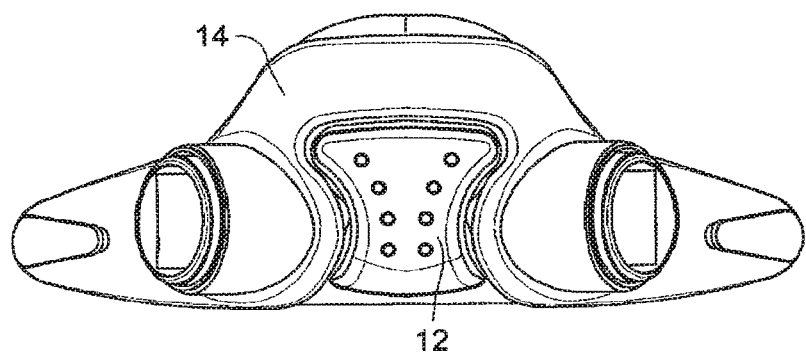
FIG. 17 schematically depicts a front view of a cushion and support structure of the mask of FIG. 1.
Figure 18:
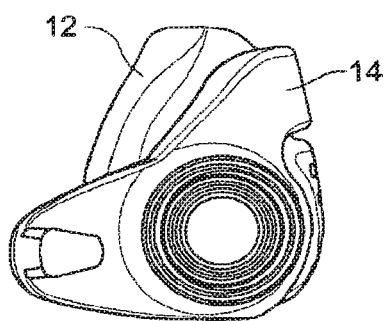
FIG. 18 schematically depicts a right side view of a cushion and support structure of the mask of FIG. 1.
Figure 19:
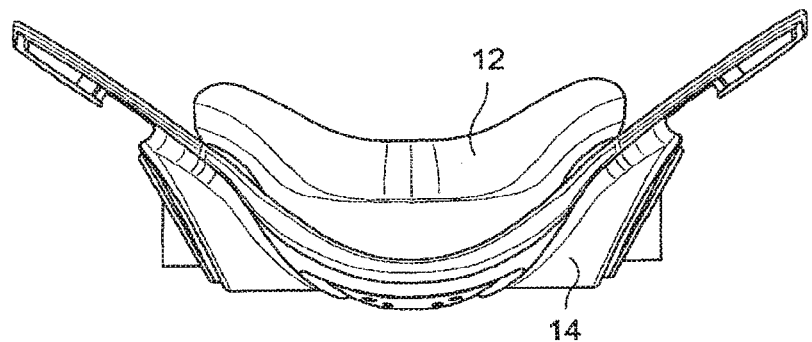
FIG. 19 schematically depicts a top view of a cushion and support structure of the mask of FIG. 1.
Figure 20:
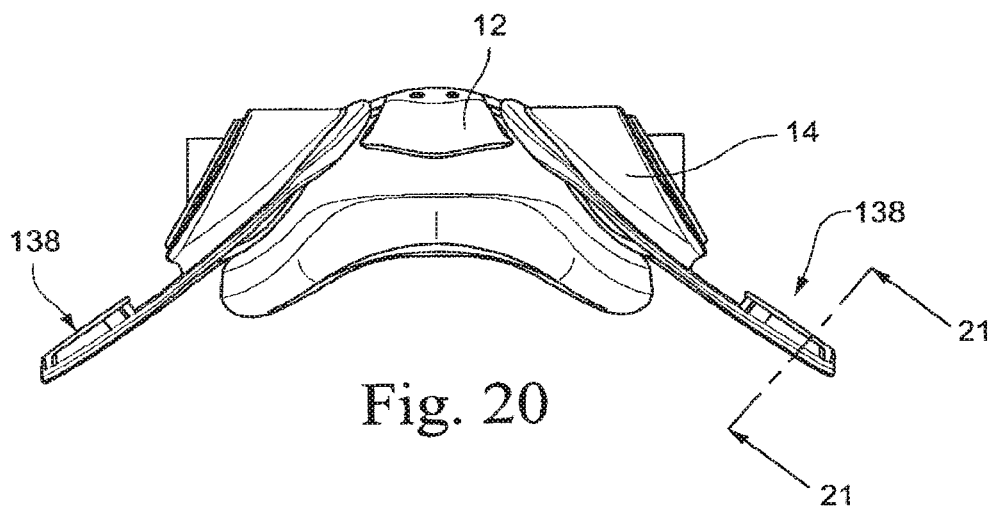
FIG. 20 schematically depicts a bottom view of a cushion and support structure of the mask of FIG. 1.
Figure 21:
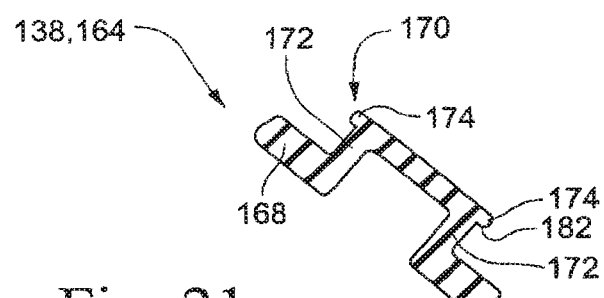
FIG. 21 schematically depicts a cross-sectional view through Section 21-21 of FIG. 20.
Figure 22:
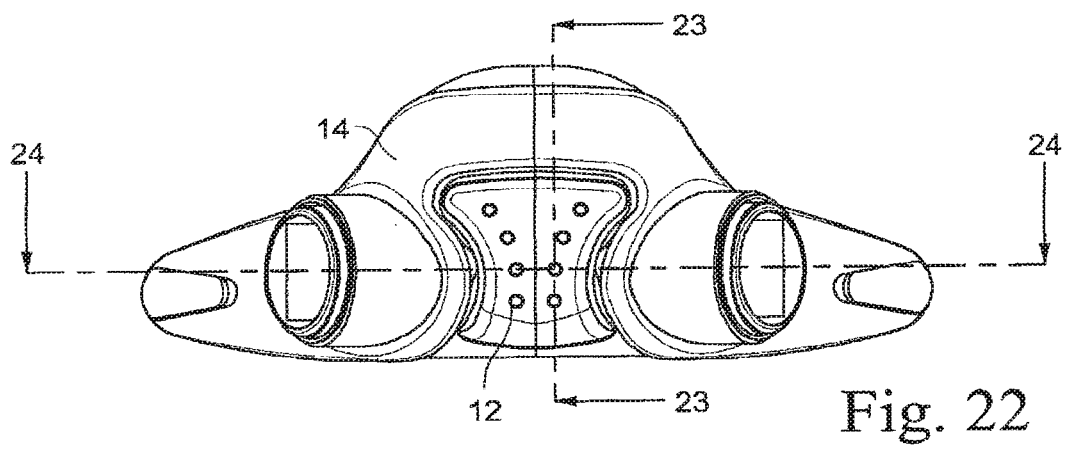
FIG. 22 schematically depicts a front view of a cushion and support structure of the mask of FIG. 1.
Figure 23:
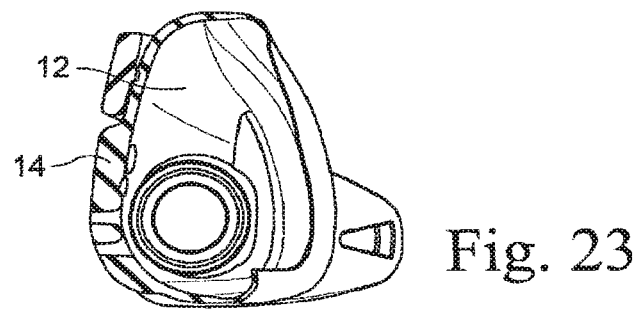
FIG. 23 schematically depicts a cross-sectional view through Section 23-23 of FIG. 22.
Figure 24:
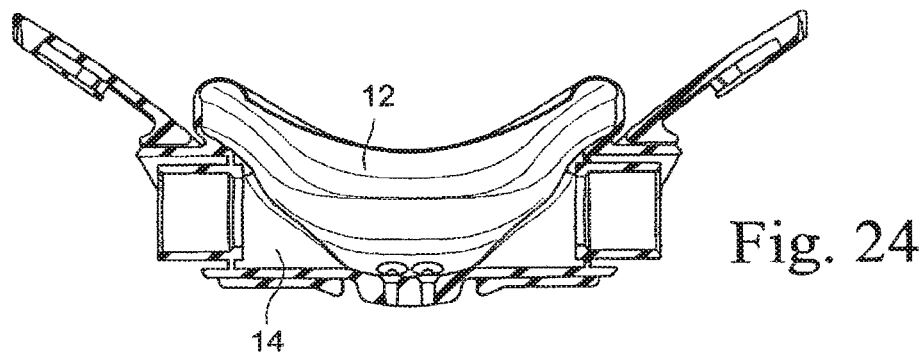
FIG. 24 schematically depicts a cross-sectional view through Section 24-24 of FIG. 22.
Figure 25:
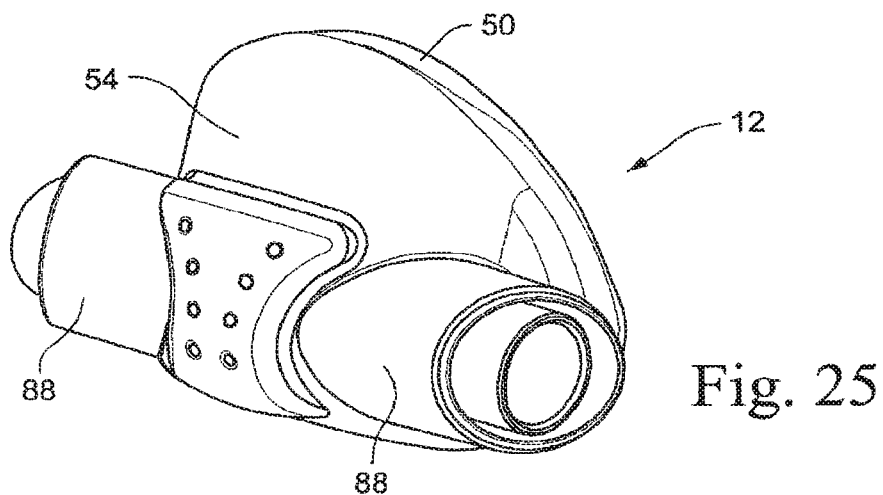
FIG. 25 schematically depicts a front perspective view of a cushion of the mask of FIG. 1.
Figure 26:
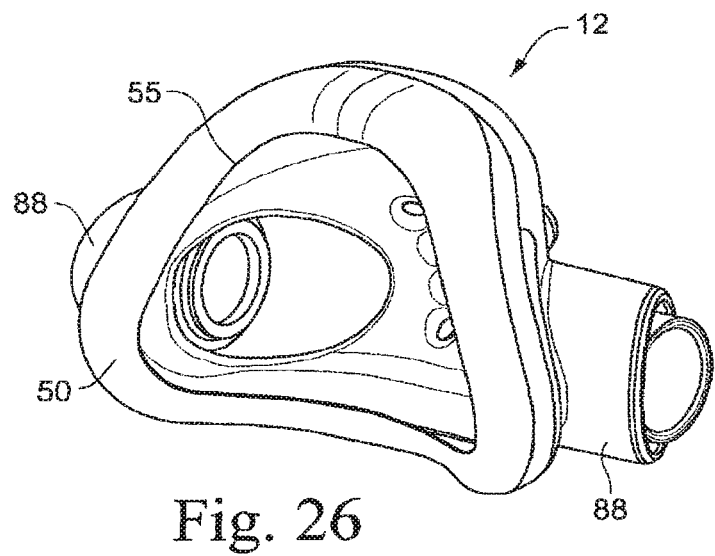
FIG. 26 schematically depicts a rear perspective view of the cushion of FIG. 25.

The present invention relates to a respiratory system that has been designed for pediatric use (i.e. with infants or children) although aspects of the system may be used advantageously by adults. The respiratory system comprises a mask, a blower/flow generator/Continuous Positive Airway Pressure (CPAP)/Variable Positive Airway Pressure Device (VPAP) device and an air delivery tubing arrangement connecting the two.

Generally, the mask is intended for use by patients in the range from neonates to pre-pubescent children. The particular specifications of the mask in FIGS. 1-12 are particularly effective in the 2-4 year age group, but may also be effective in treating neo-natal patients. Referring to FIGS. 1-24, the respiratory system comprises a mask 10 that is particularly effective in the treatment of 2-4 year old children and an air delivery tube 11 (FIGS. 71-74). The mask 10 may comprise a cushion 12, a support structure 14, headgear 16 (FIGS. 71-74), an elbow 18 and a plug 20. The headgear 16 may include a pair of relatively rigid members 22 and the support structure 14 may include a pair of cheek pads 24.

Mask Overall Configuration

A preferred form of mask provides at least one air inlet on a side of the mask (e.g. left or right) rather than via a front-mounted inlet, or a top-located inlet (e.g. between the eyes). Preferably there are two inlets, one on the left and the other on the right side. The use of a side-mounted inlet leads to a much lower profile than a front mounted inlet. See for examples, FIGS. 1, 2 & 4.

Another preferred aspect of the mask is that it does not have a forehead support. This reduces the obtrusiveness of the mask and protects the soft, developing bones of pediatric patient's foreheads from impairment or damage. Alternative features of the present invention stabilize the mask to compensate for the lack of forehead support. Such stabilizing features may be in one form as described in WO/2003/090827 (Moore et al, assigned to ResMed) the contents of which are hereby incorporated by cross-reference. Other aspects will be discussed in further detail.

Cheek Pads

Referring to FIGS. 3, 4 and 13a-13g, cheek pads 24 are also provided on the support structure 14 to (i) stabilize the mask 10 in terms of lateral movement or rotation, and (ii) to receive and distribute the load due to headgear tension so that the cushion is not stretched or crushed. Cheek pads also provide greater comfort to the patient by reducing hard surfaces contacting the skin and may therefore allow comfortable stomach sleeping. The cheek pads 24 may be approximately 32 mm long, 18 mm wide and 3 mm thick, although it should be appreciated that in other embodiments these dimensions may vary up 10%, up to 20% or up to 50% and still achieve the same or similar functionality. The cheek pads 24 are generally trapezoidal in shape, but could also be square or rounded or any other suitable shape.

In the depicted sample embodiment, the distance between the face contacting surfaces 124 of the cheek pads 24 is less than the width of a typical patient's face such that the pads 24 grip the patient's face and thereby stabilizes the cushion 12 and so also the support structure 14.

Figure 55:
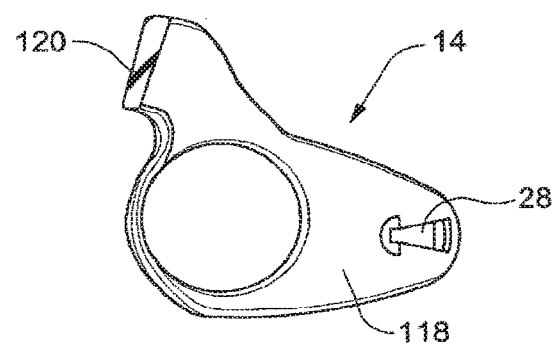
FIG. 55 schematically depicts a cross-sectional view through Section 55-55 of FIG. 54.
Figure 56A:
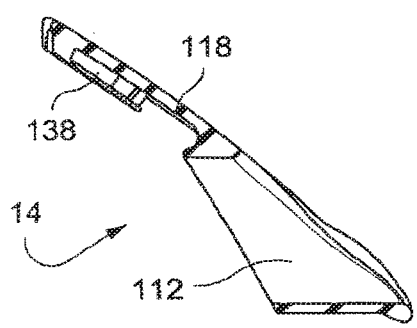
FIGS. 56a and 56b schematically depict a cross-sectional view through Section 56a-56a of FIG. 54.
Figure 56B:
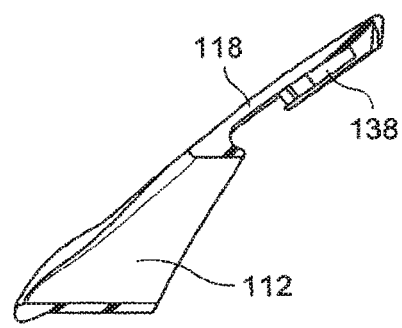
Figure 57:
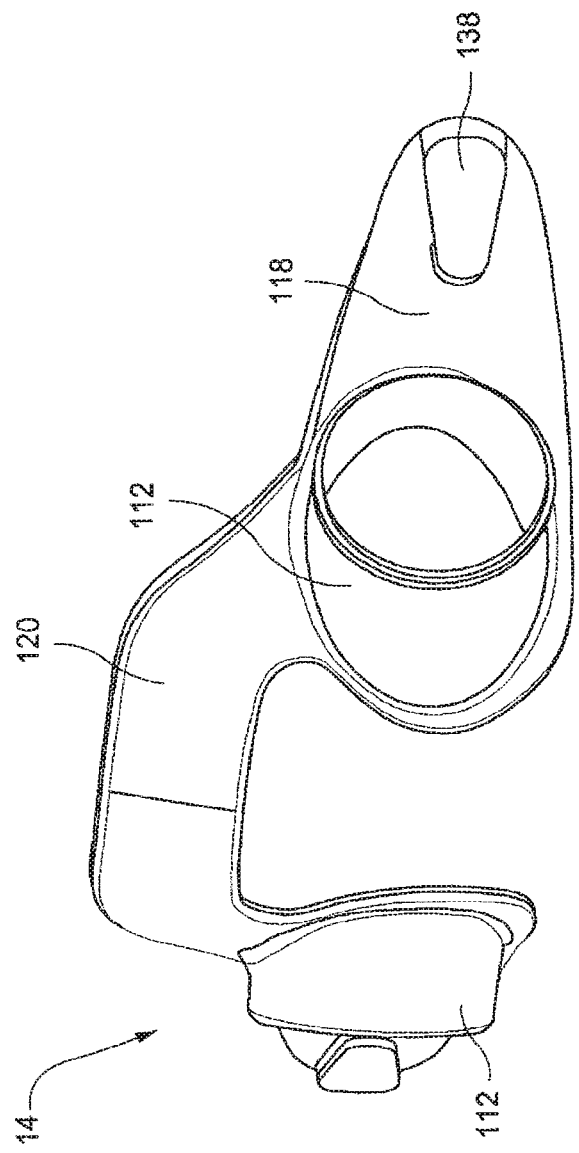
FIG. 57 schematically depicts another front perspective view of the support structure of FIG. 47.
Figure 58A:
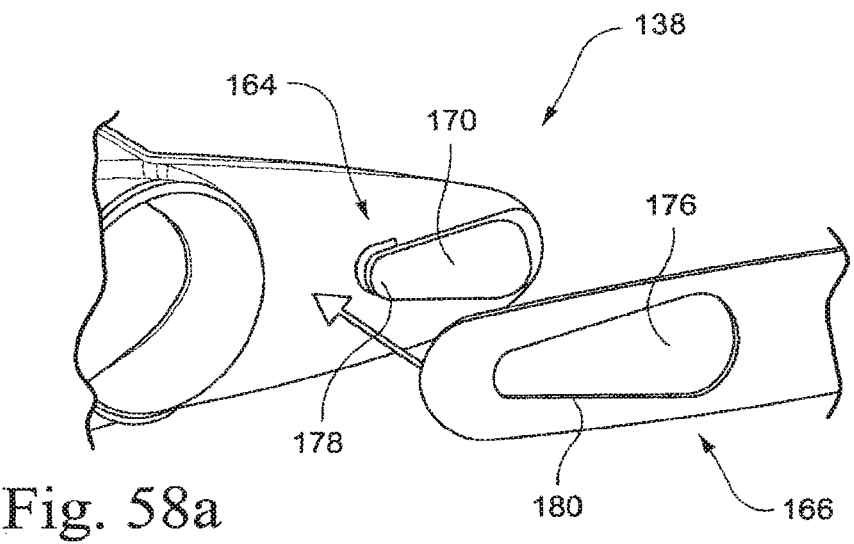
FIG. 58a schematically depicts one of the relatively rigid members being moved towards the support structure, FIG. 58b schematically depicts the one of the relatively rigid members and the support structure in mating relation but not yet locked, and 58c schematically depicts the one of the relatively rigid members locked to the support structure.
Figure 58B:
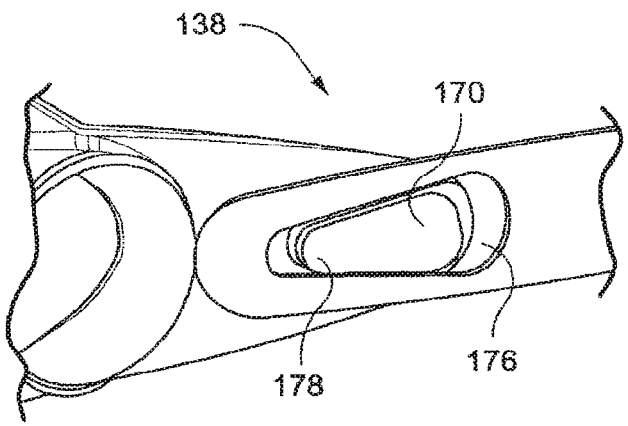
Figure 58C:
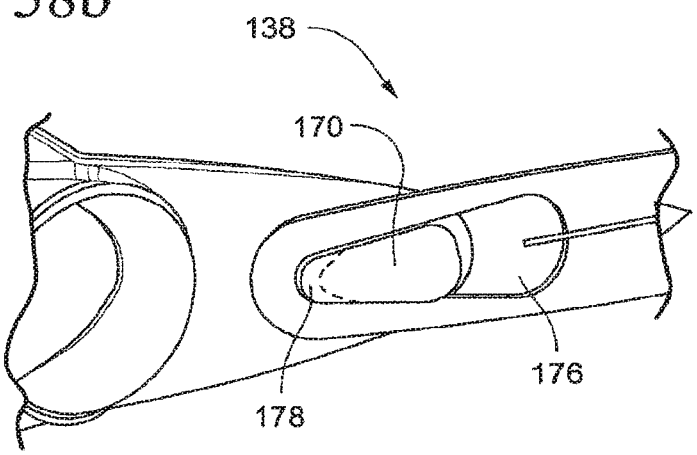
Figure 59:
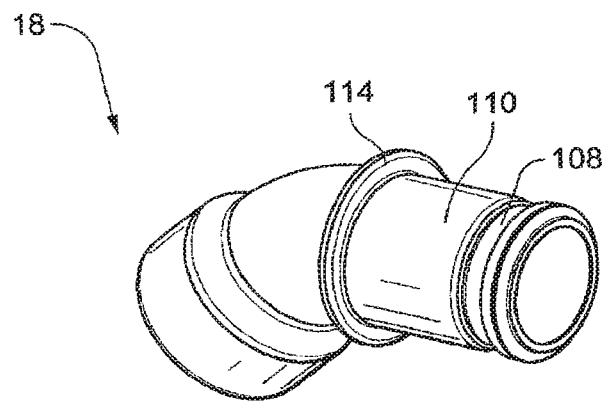
FIG. 59 schematically depicts a perspective view of a swivel elbow of the mask of FIG. 1 from the swivel end.
Figure 60:
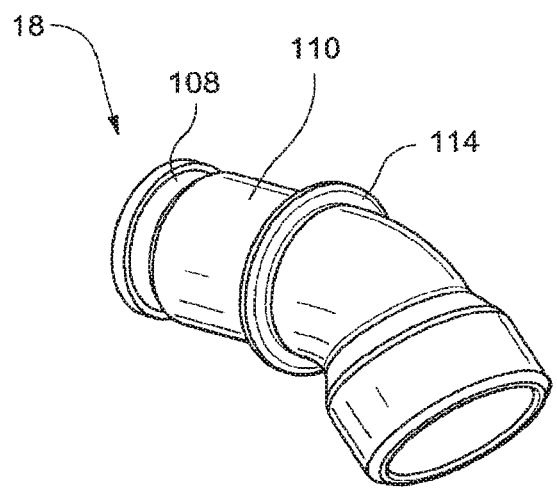
FIG. 60 schematically depicts a perspective view of the swivel elbow of FIG. 59 from the elbow end.
Figure 61:
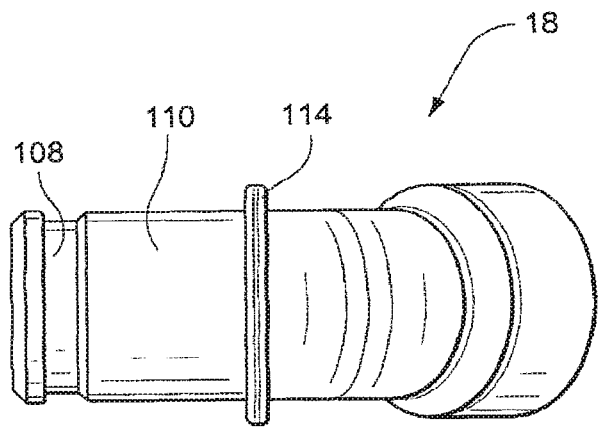
FIG. 61 schematically depicts a top view of the swivel elbow of FIG. 59.
Figure 62:
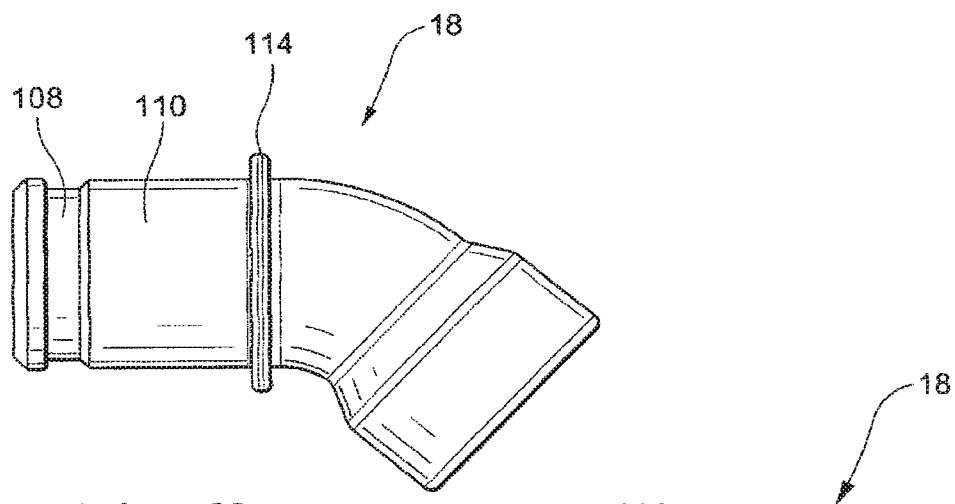
FIG. 62 schematically depicts a front view of the swivel elbow of FIG. 59.
Figure 63:
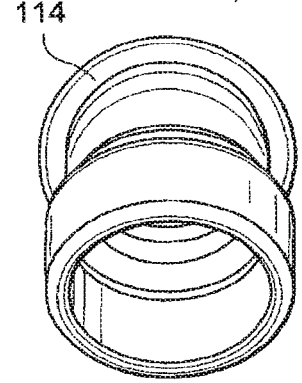
FIG. 63 schematically depicts an end view of the swivel elbow of FIG. 59 from the elbow end.
Figure 64:
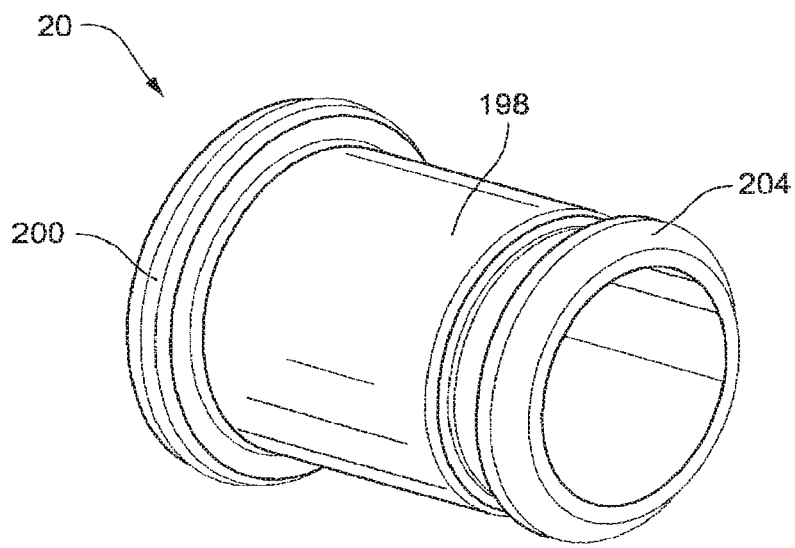
FIG. 64 schematically depicts a perspective view of a plug of the mask of FIG. 1 from the connection end.
Figure 65:
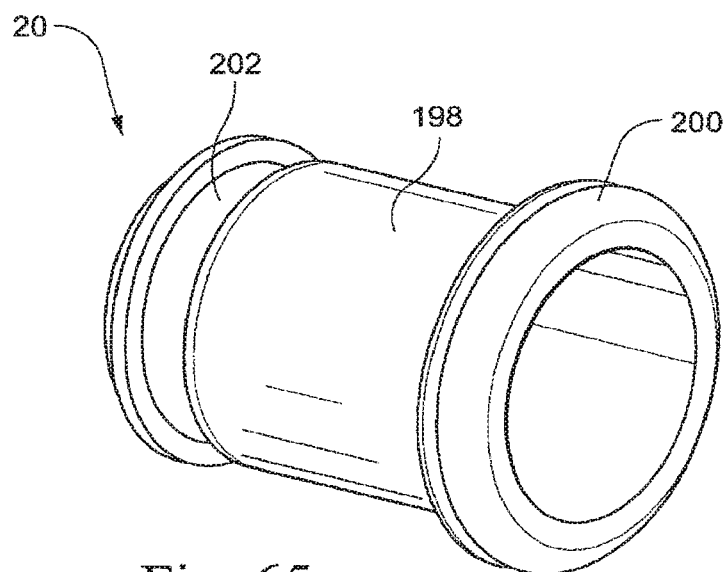
FIG. 65 schematically depicts a perspective view of the plug of FIG. 64 from the plug end.
Figure 66:
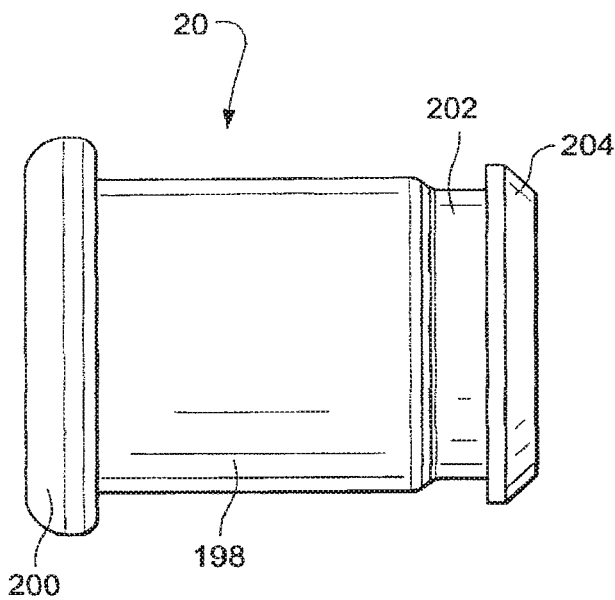
FIG. 66 schematically depicts a side view of the plug of FIG. 64.

In the depicted embodiment, the cheek pads 24 are joined to the support structure 14 via an adhesive. To assist the adhesive, the pads 24 also include a key-hole shaped rib 26 which is designed to locate in a friction-fit in a cooperating key-hole shaped groove 28 (FIG. 55) in the support structure 14. The friction and increase in adhesive area both enhance the attachment of the cheek pads 24 to the support structure 14.

In this embodiment the cheek pads 24 are made of a low durometer silicone. In other variations, the cheek pads 24 could be made of open or closed cell, soft, viscoelastic foam or another suitably soft engineering material that fulfils known biocompatibility requirements.

In another embodiment, no discrete cheek pads 24 are provided, but the cushion 14 is stabilized on the patient's face by a specific arrangement of the headgear 16, for example, extensions of the headgear 16 along the inside surfaces of the wings 118 of the support structure 14.

Cushion

Referring now to FIGS. 25-46, the cushion 12 is formed from a flexible, elastomeric material, in this case silicone that is designed to provide comfort to the patient while forming an adequate seal. The cushion defines an air chamber 26 (FIG. 5) into which the patient's nose is inserted in use. The cushion 12 locates above the patient's nasal vents and below the patient's nostril openings so that it does not impinge upon them. This allows a ready flow of air around the air chamber 26 to assist breathing and exhalation.

The cushion 12 is generally trapezoidal in shape and has a front side 28 facing away from the patient, a rear side 30 in contact with the patient's face, a top side 32, a bottom side 34 and two lateral sides 36. The top side 32 of the cushion 12 corresponds to the shorter of the substantially parallel sides of the trapezoid and is the side closest to the top of the patient's nose. The bottom side 34 of the cushion 12 corresponds to the longer of the substantially parallel sides of the trapezoid and is the side closest to the bottom of the patient's nares. The lateral sides 36 of the cushion 12 correspond to the non-parallel sides of the trapezoid and are closest to the patient's nostrils.

Figure 27:
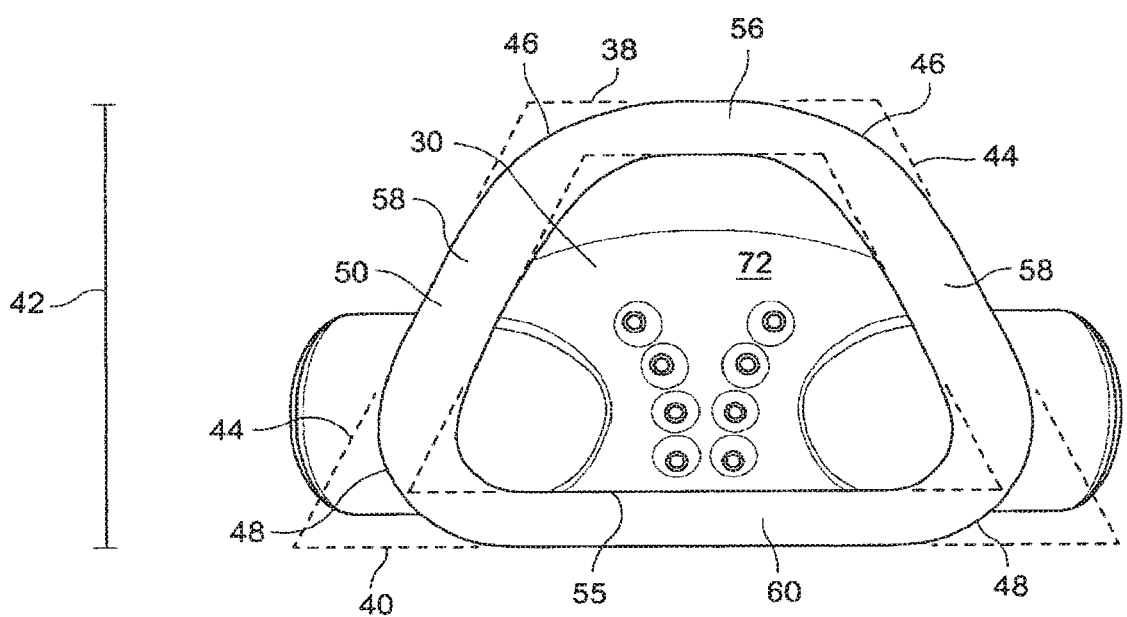
FIG. 27 schematically depicts a rear view of the cushion of FIG. 25.
Figure 28:
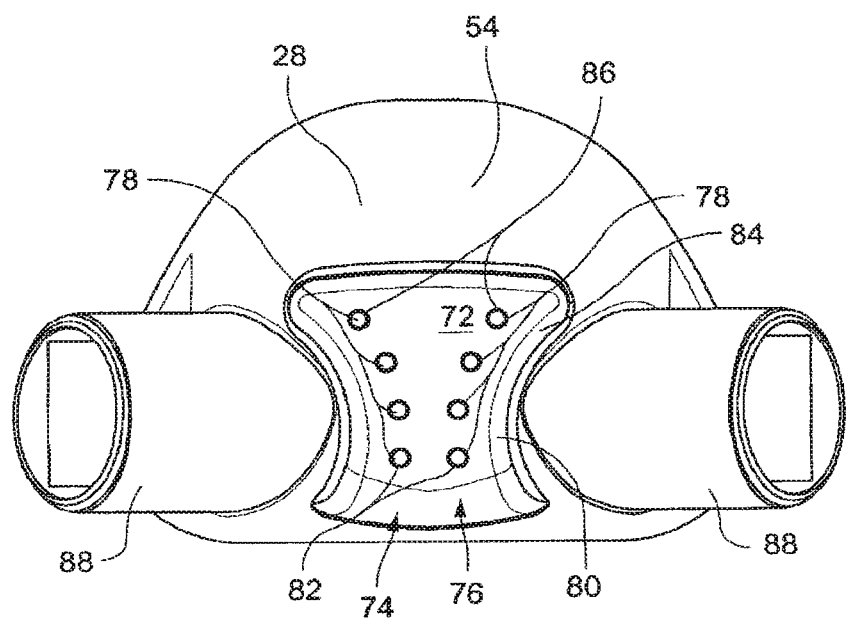
FIG. 28 schematically depicts a front view of the cushion of FIG. 25.

The dimensions of the depicted cushion 12 will now be described with reference to FIG. 27 where the rear side 30 of the depicted cushion 12 is shown inscribed within the boundaries of a trapezoid. The length of the top side 38 of the trapezoid is about 28.4 mm, and the length of the bottom side 40 is about 55.4 mm. The length of each lateral side 44 is about 36.5 mm. As depicted, however, the edges of the cushion 12 are rounded. In this embodiment, the rounds are not radiuses but can be approximated as such. Thus, the top rounds 46 approximate to a radius of about 13 mm, and the bottom rounds 48 approximate to a radius of about 5 mm.

The trapezoidal shape is anatomically suitable to allow the cushion 12 to surround the patient's nose without obstructing the patient's field of vision. This shape is particularly suitable for infants and children. It should be appreciated that these dimensions may vary but still be suitable, for example, the top side of the trapezoid 38 may be between about 10 mm and 50 mm in length and the bottom side of the trapezoid 40 may be between about 20 mm and 90 mm in length. The length 44 of each lateral side 36 may be between about 20 mm and 60 mm in length. The top corners may include rounds 46 having a radius of up to 30 mm and the bottom corners may include rounds 48 having a radius of up to 20 mm. One reason for the provision of masks within these dimensional ranges is that different patients (e.g. infants, children, babies born prematurely, teenagers and adults) require differently sized cushions. In a size range suitable for pediatric patients, the dimensional ratio of length-to-width remains substantially constant while the depth changes very little. During puberty patient's noses grow more rapidly than during their preceding years, thus necessitating a mask of increased depth.

The rear side 30 of the cushion 12 comprises at least one thin flexible membrane 50 and at least one base wall 52 that connects the at least one membrane 50 with a dome portion 54 of the cushion 12 (i.e. at the front side 28 of the cushion 12). In the depicted sample embodiment one membrane 50 and one base wall 52 are provided and together form part of the side wall 32, 34 and 36 of the air chamber 26. The membrane 50 forms a seal against the adjacent portion of the patient's face around the patient's nose while the base wall 52 elevates the front side 28 of the cushion 12 above the patient's nose. This allows pressurised air (e.g. CPAP therapy) to be delivered to the patient. Although one membrane is shown, it should be appreciated that the cushion may be a double membrane cushion, or that any number of membranes greater than one may be provided.

The membrane defines an aperture 55 for receiving the patient's nose. The shape of the aperture 55 is similar to the shape of the cushion 12. The dimensions of the depicted aperture 55 will now be described with reference to FIG. 27 where the aperture 55 of the depicted cushion 12 is shown inscribed within the boundaries of a trapezoid. The length of the top side of the trapezoid is about 18.5 mm and the length of the bottom side is about 40.2 mm. The length of each lateral side is about 28.1 mm. As depicted, however, the edges of the aperture 55 are rounded. In this sample embodiment, the rounds are not radiuses but can be approximated as such. It should be appreciated that these dimensions may vary in proportion with or in relation to the size of the cushion 12. The dimension could vary by 50% or more.

The membrane 50 generally has three portions, each having a different cross-sectional shape. A top portion 56 is located substantially over the patient's nasal bridge, two side portions 58 are located substantially at either side of the patient's nares and a bottom portion 60 is located substantially under the patient's nose. The exterior dimensions of the membrane 50 from a rear perspective (as shown in FIG. 27) are the same as the corresponding overall dimensions of the cushion 12 as detailed above.

The cross-sections of each of these three portions 56, 58 and 60 are generally C-shaped but they vary with resect to radius, curvature and material thickness. By way of a general comparison, the top and bottom portions 56 and 60 have a larger curvature or roll than the side portions 58 and the bottom portion 60 is thicker than the top 56 and side portions 58.

The word "curvature" as used in this specification means the angle of a circle subtended by the membrane 50. A greater curvature allows the cushion membrane 50 to bend more easily since it rolls more easily. This, in turn, allows a greater degree of compression for a given force (i.e. the membrane 50 is softer). Thus, regions of high curvature have been incorporated into the top and bottom portions 56 and 60 of the mask cushion 12 which contact sensitive areas of the patients face (i.e. nasal bridge region and region between the patient's nose and mouth). This increases patient comfort and reduces the possibility of pressure sores.

The advantage of the thicker bottom portion 60 is that it provides the mask 10 with greater stability.

The dimensions for radius, curvature and material thickness are provided in Table 1 below.

TABLE 1

|  | Radius (mm) | Curvature (deg) | Thickness at tip (mm) |
| --- | --- | --- | --- |
| Top Section | 2.5 | 106 | 0.2 |
| Side Section | 2.25 | 160 | 0.2 |
| Bottom Section | 2.5 | 108 | 0.4 |

Suitable ranges for dimensions for radius, curvature and material thickness are provided in Table 2 below.

TABLE 2

|  | Radius (mm) | Curvature (deg) | Thickness at tip (mm) |
| --- | --- | --- | --- |
| Top Section | 2-3 | 90-120 | 0.1-0.4 |
| Side Section | 1.75-2.75 | 145-175 | 0.1-0.4 |
| Bottom Section | 2-3 | 90-120 | 0.2-0.6 |

Figure 29:
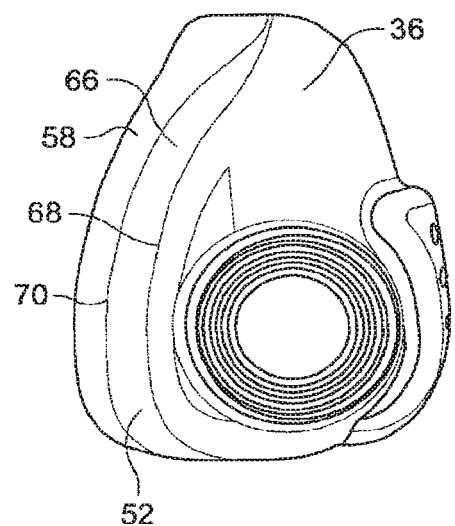
FIG. 29 schematically depicts a right side view of the cushion of FIG. 25.
Figure 30:
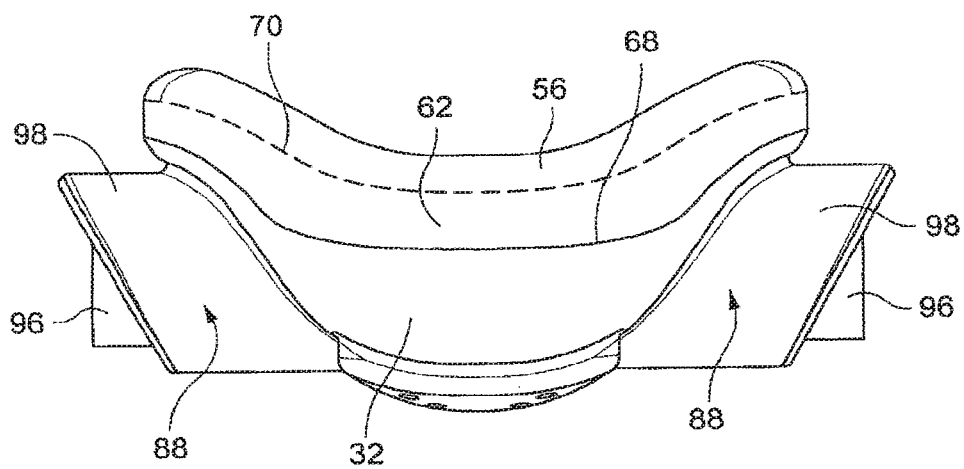
FIG. 30 schematically depicts a top view of the cushion of FIG. 25.
Figure 31:
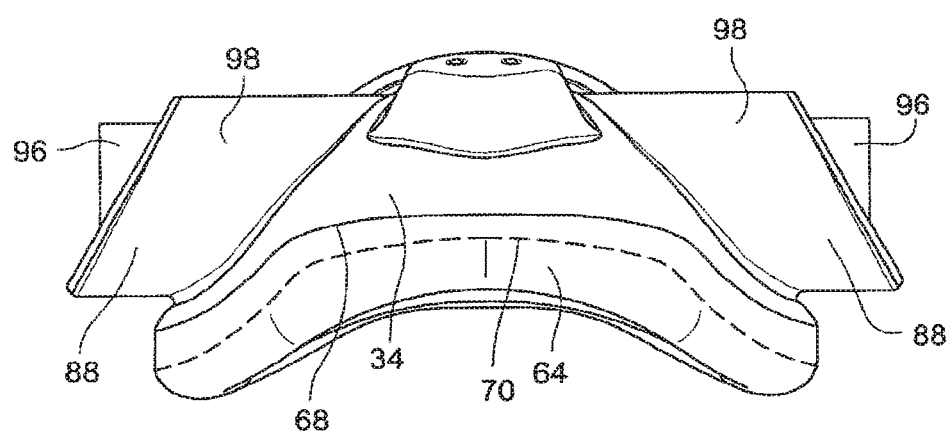
FIG. 31 schematically depicts a bottom view of the cushion of FIG. 25.
Figure 32:
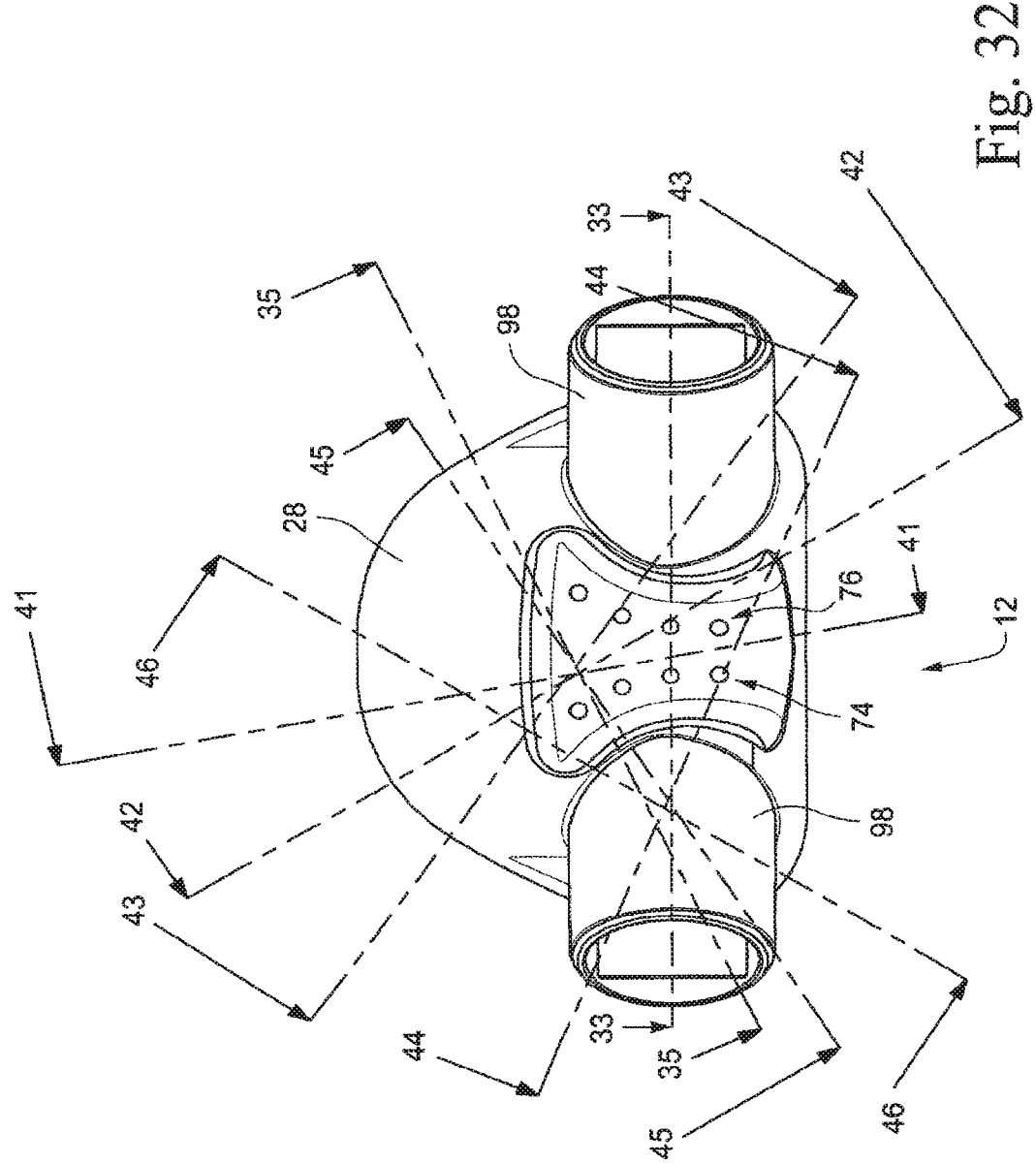
FIG. 32 schematically depicts a front view of a cushion of the mask of FIG. 1.
Figure 33:
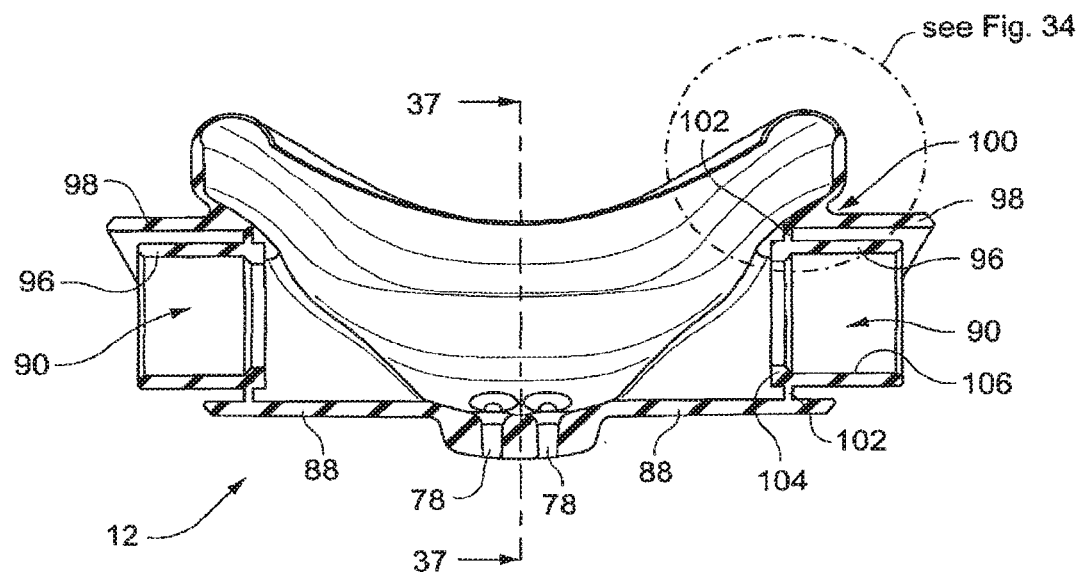
FIG. 33 schematically depicts a cross-sectional view through Section 33-33 of FIG. 32.
Figure 34:
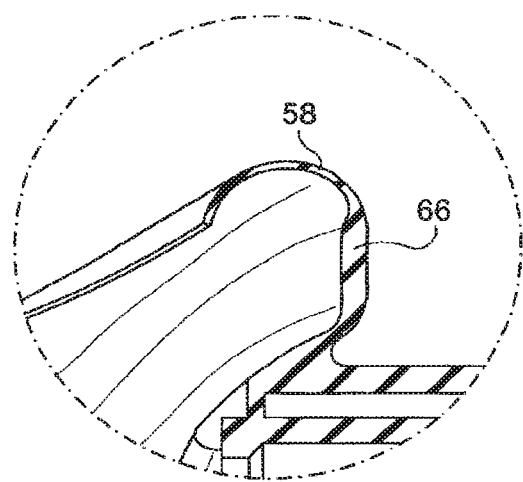
FIG. 34 schematically depicts detail of FIG. 33.
Figure 35:
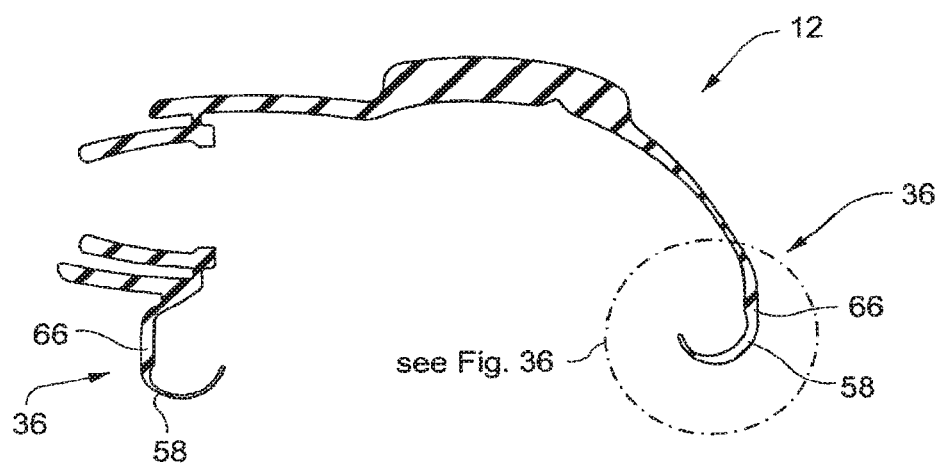
FIG. 35 schematically depicts a partial cross-sectional view through Section 35-35 of FIG. 32.
Figure 36:
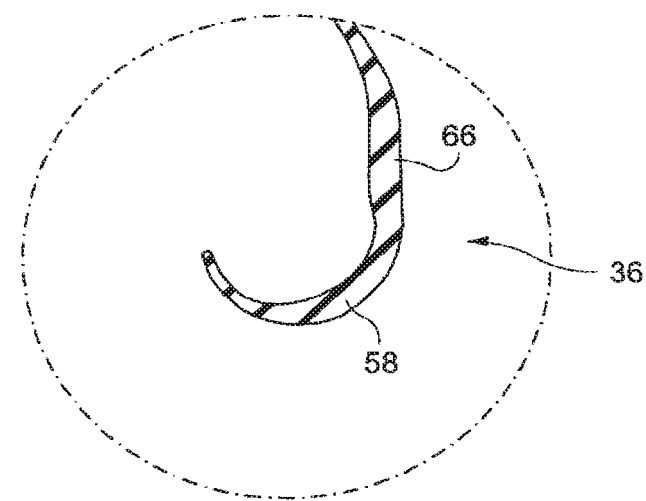
FIG. 36 schematically depicts detail of FIG. 35.
Figure 37:
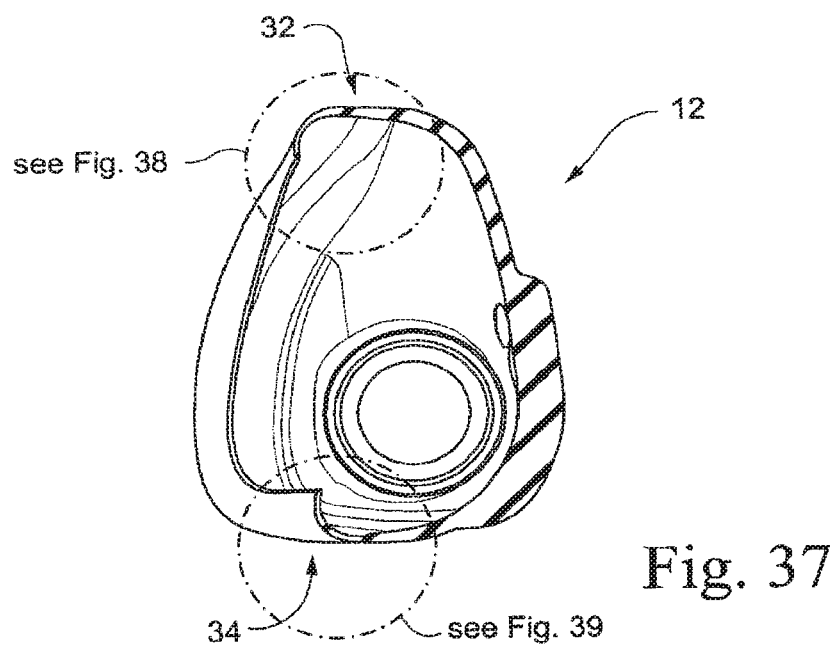
FIG. 37 schematically depicts a cross-sectional view through Section 37-37 of FIG. 33.
Figure 38:
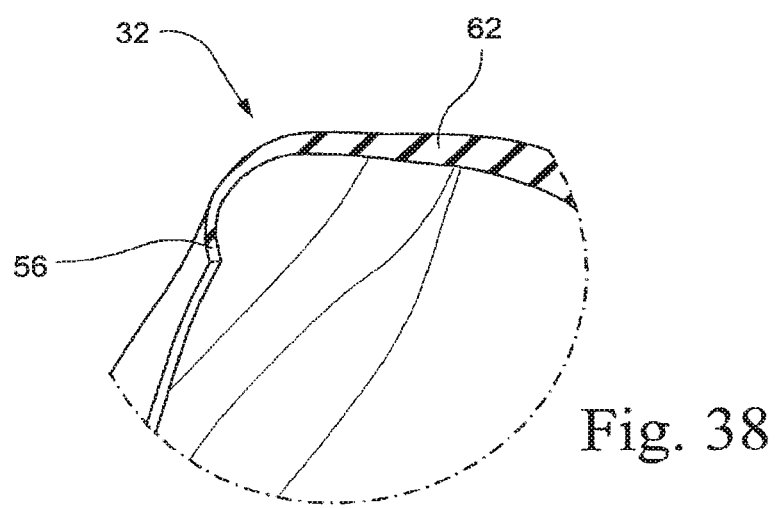
FIG. 38 schematically depicts a first detail of FIG. 37.
Figure 39:
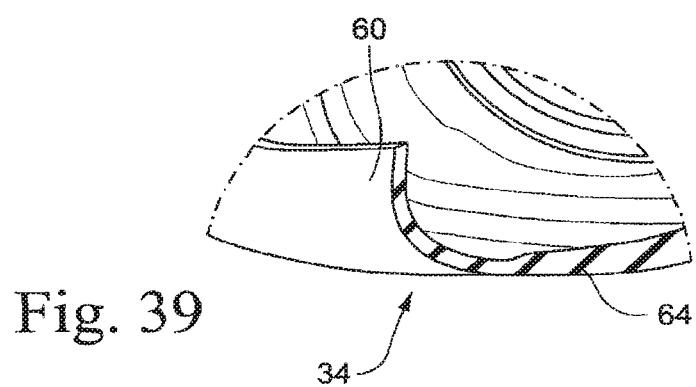
FIG. 39 schematically depicts a second detail of FIG. 37.
Figure 40:
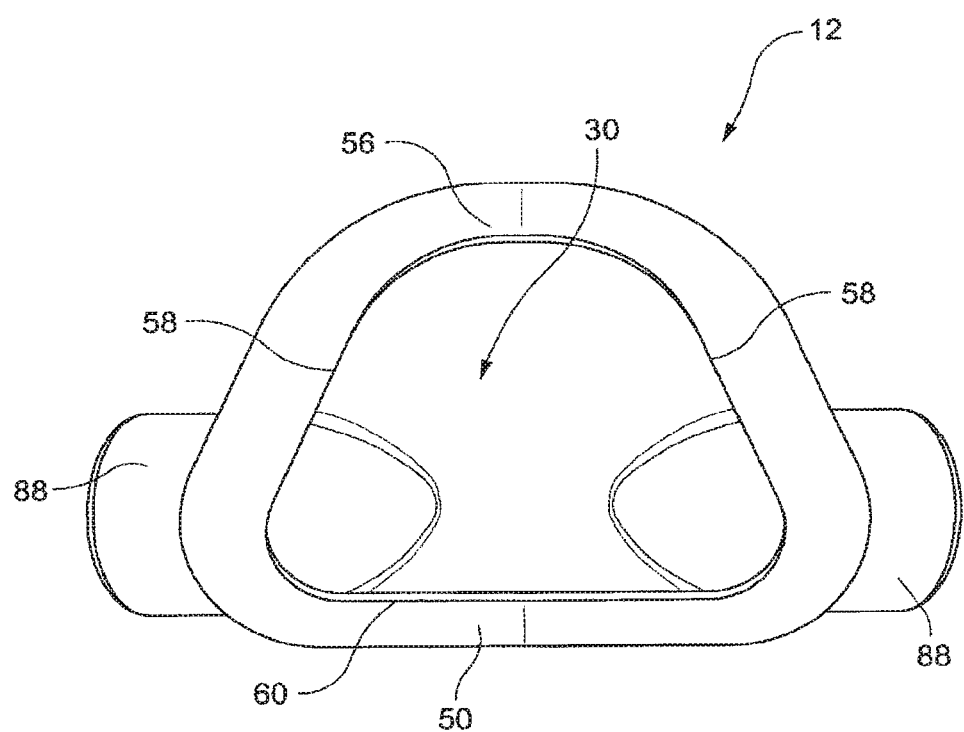
FIG. 40 schematically depicts a rear view of the cushion of the mask of FIG. 1 and highlights various membrane regions.
Figure 42:
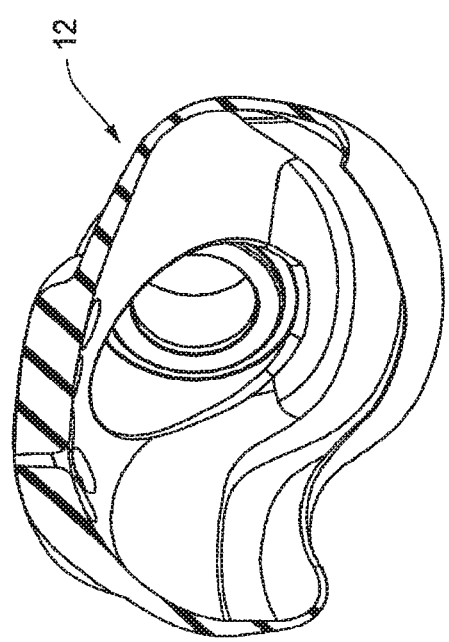
FIGS. 41-46 schematically depict cross-sectional views through sections 41-41-46-46 of FIG. 32, respectively.
Figure 41:
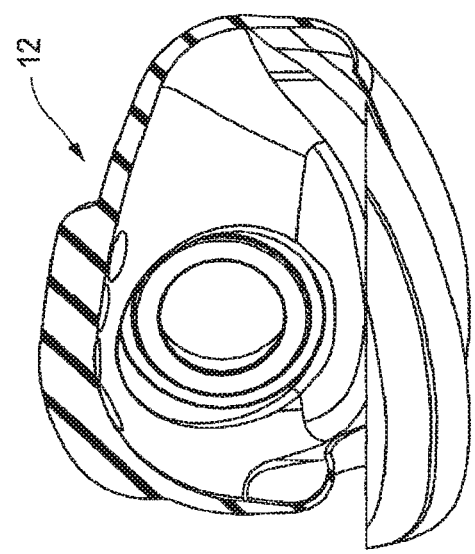
Figure 44:
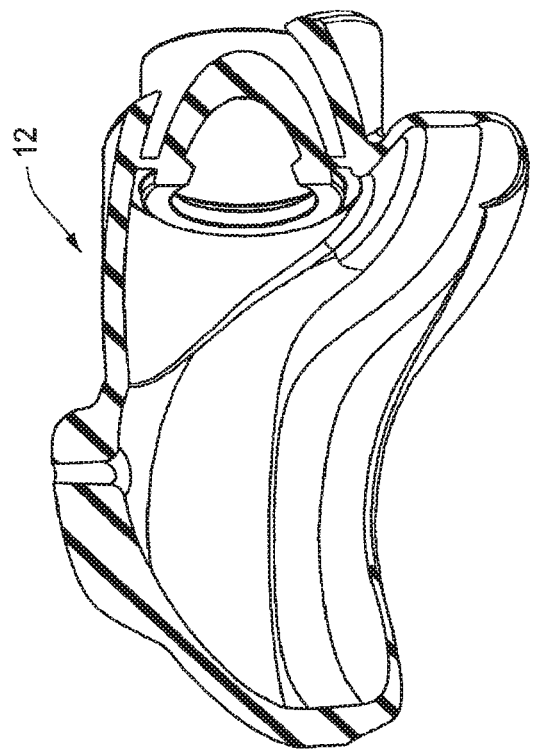
Figure 43:
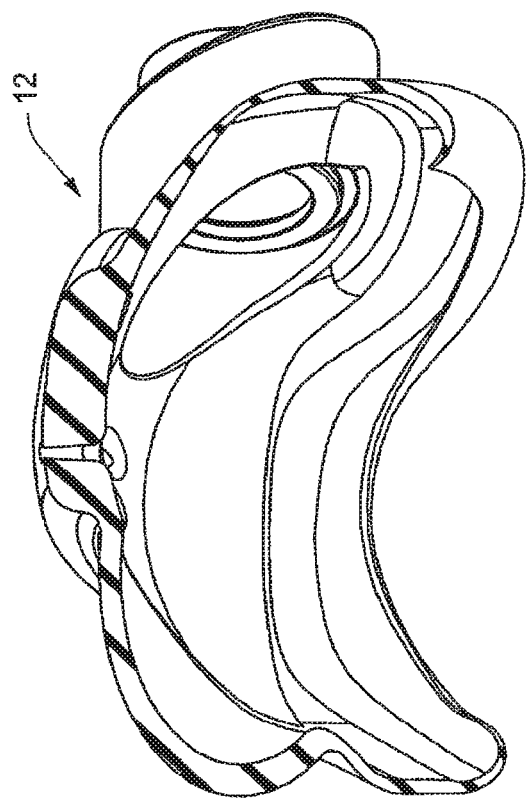
Figure 46:
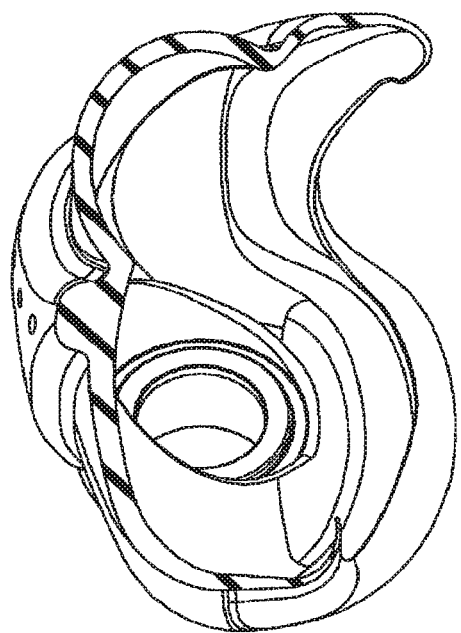
Figure 45:
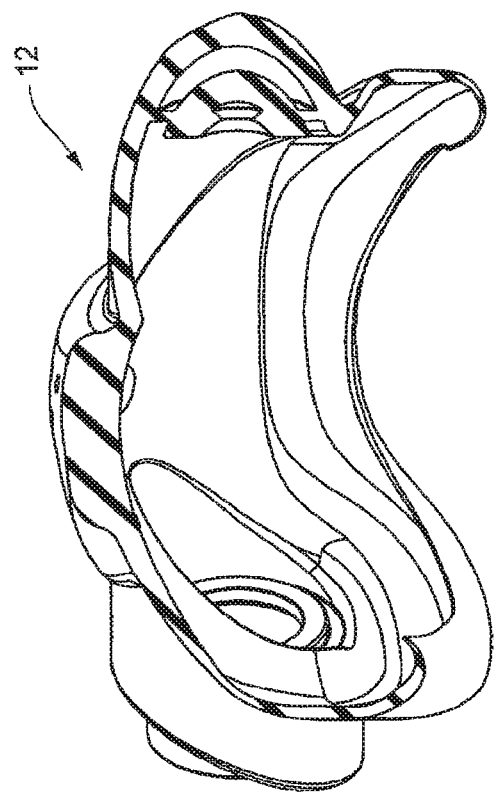
Figure 47:
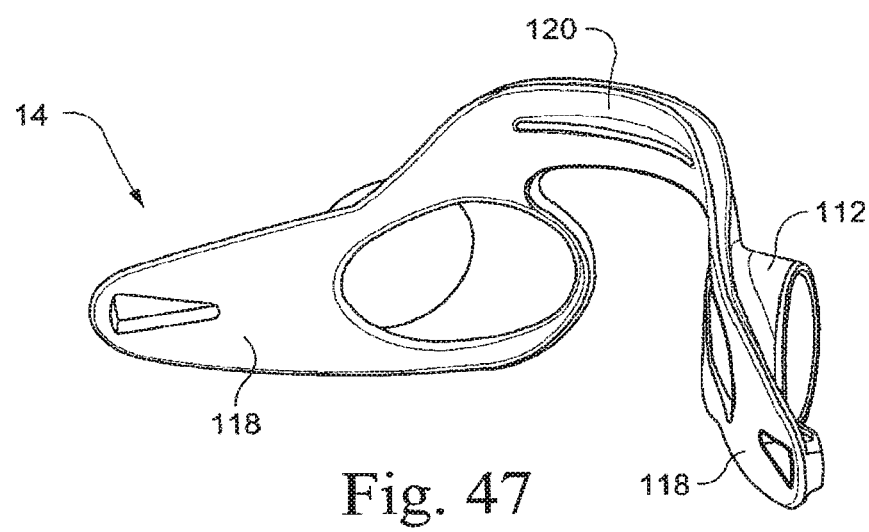
FIG. 47 schematically depicts a rear perspective view of a support structure of the mask of FIG. 1.
Figure 48:
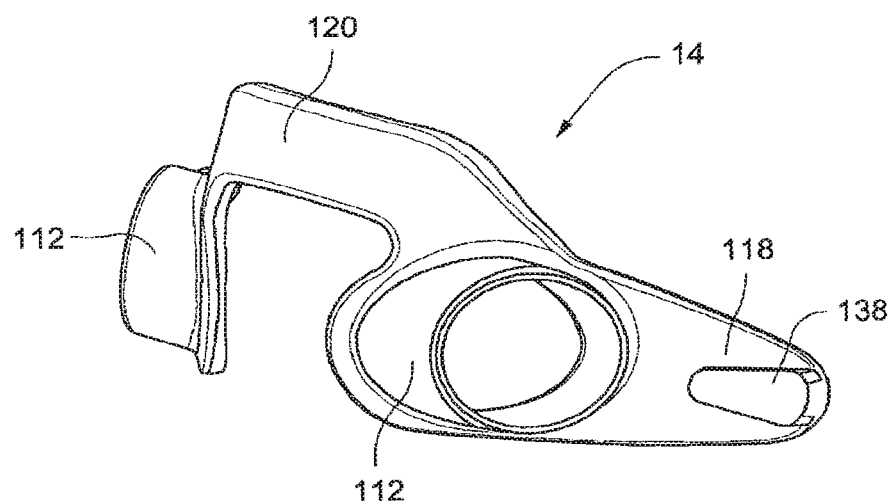
FIG. 48 schematically depicts a front perspective view of the support structure of FIG. 47.
Figure 49:
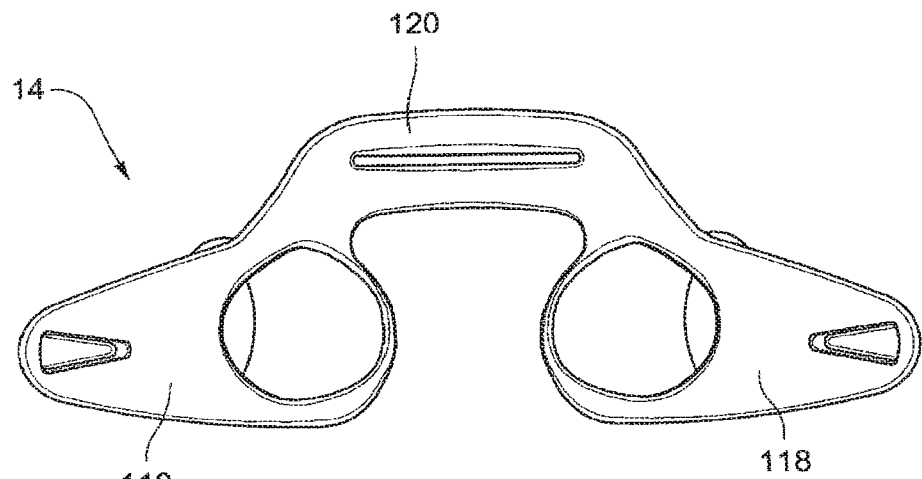
FIG. 49 schematically depicts a rear view of the support structure of FIG. 47.
Figure 50:
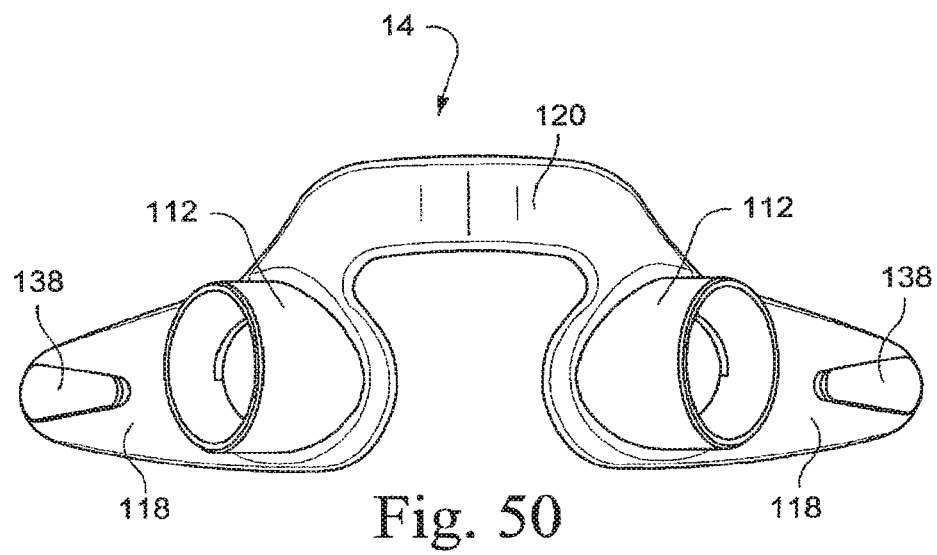
FIG. 50 schematically depicts a front view of the support structure of FIG. 47.
Figure 51:
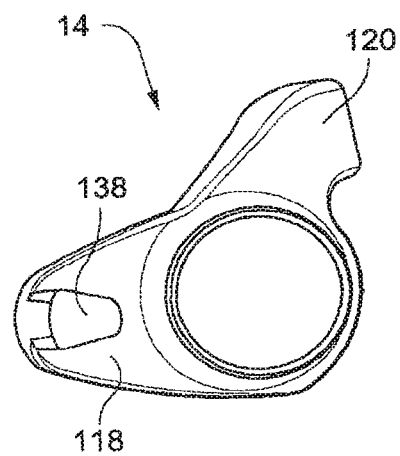
FIG. 51 schematically depicts a right side view of the support structure of FIG. 47.
Figure 52:
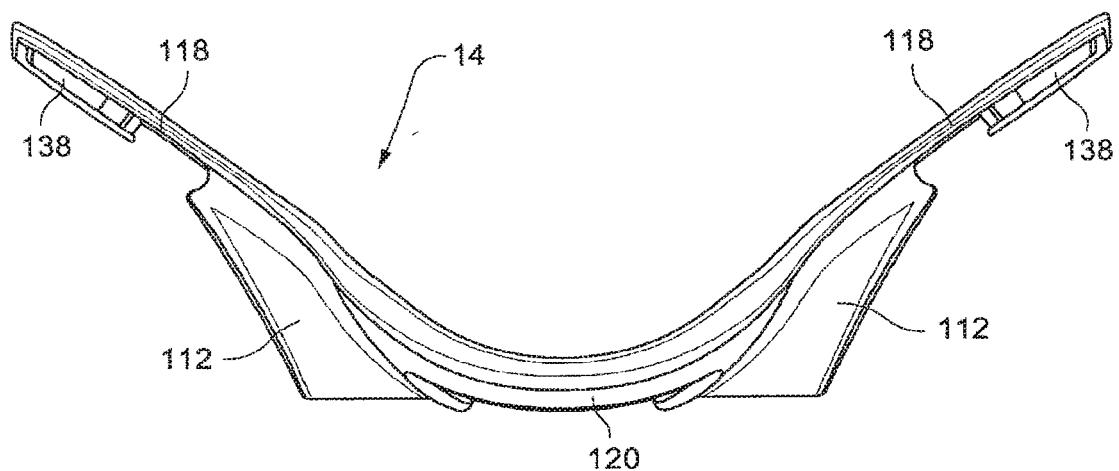
FIG. 52 schematically depicts a top view of the support structure of FIG. 47.
Figure 53:
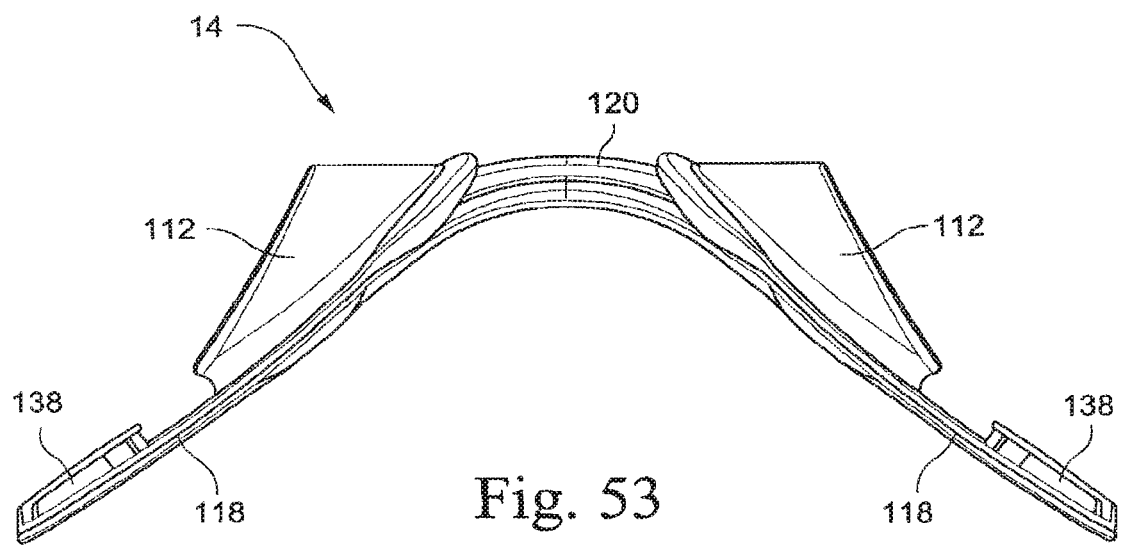
FIG. 53 schematically depicts a bottom view of the support structure of FIG. 47.
Figure 54:
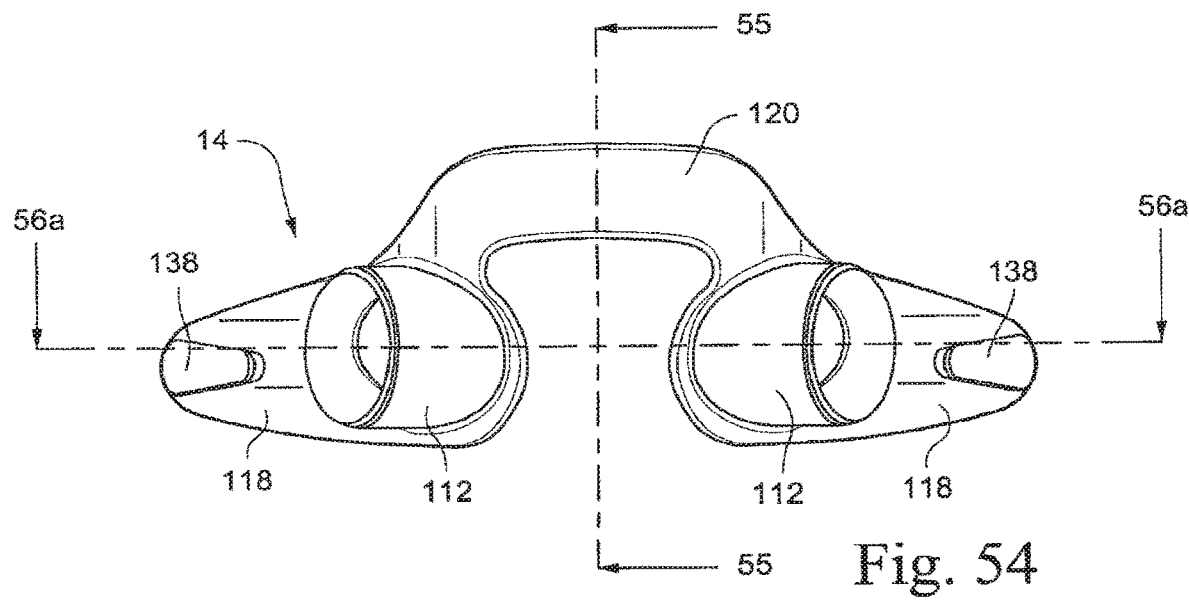
FIG. 54 schematically depicts a front view of the support structure of FIG. 47.

In the depicted sample embodiment the base wall 52 is substantially aligned to the forward-aft direction of the mask 10 and varies in width around the perimeter of the mask 10. The base wall 52, like the membrane 50 comprises three main parts: a top portion 62 (FIG. 30), a bottom portion 64 (FIG. 31) and two side portions 66 (FIG. 29). As can be seen in FIGS. 30 and 31 the base wall 52 has a maximum width at its top and bottom portions 62 and 64 of about 8 mm. Referring to FIG. 29, the base wall 52 tapers down to a minimum width of about 5 mm at its side portions 66. In other sample embodiments, this width varies by up to 50% and in yet other embodiments by up to 100%.

The thickness of the side portions 66 of the base wall 52 may be about 0.9 mm. The thickness of the top and bottom portions 62 and 64 of the base wall 52 tapers down from about 0.9 mm at the base 68 of the base wall 52 to about 0.5 mm at a transition region 70 where the base wall 52 transitions into the membrane 50.

In one sample embodiment, the cushion 12 is transparent or water clear such that a parent or clinician can inspect the patient's nares. This is particularly important in the case of children to ensure that there are no physical obstructions to nasal breathing (e.g. mucus). Additionally, a clear path of sight may also assist in fitting the mask to the patient by a third party (for example, nurse or parent). In other sample embodiments, the cushion 12 is translucent so that any obvious obstructions to breathing can still be identified and rectified.

In another sample embodiment, the thin flexible membrane 50 may be replaced by a line of soft, visco-elastic foam. This line of foam may have a varying cross-section. Advantages of foam are that it has a warming effect on the patient's skin, feels very soft and allows a gradual leak of air, thus avoiding sudden large leaks, and the absorption and subsequent evaporation of moisture from the patient's skin.

It should also be appreciated that although in this embodiment the cushion 12 is trapezoidal in shape, it could also be triangular, rectangular, circular or square. In a sample embodiment where the cushion 12 is substantially triangular, the top side 32 of the cushion 12 corresponds to the apex of the triangle (if an isosceles triangle) or one of the corners of the triangle (if an equilateral triangle). A mask 10 that is shaped generally like an isosceles triangle is more anatomically suited for adults, whereas for children the sides tend to be closer to the same length.

In a sample embodiment where the cushion 12 is substantially rectangular, the top side 32 of the cushion 12 may correspond to either one of the shorter or one of the longer sides of the rectangle. In a sample embodiment where the mask 10 is particularly suitable for use by children, the top side 32 of the cushion 12 corresponds to one of the longer sides of the rectangle. The bottom side 34 of the cushion 12 also corresponds to one of the longer sides of the rectangle and lies underneath the openings of the patient's nares. The lateral sides 36 of the cushion 12 correspond to the shorter sides of the rectangle and lie generally adjacent to the patient's nostrils. In a sample embodiment where the mask 10 is particularly suitable for use by adults, the top and bottom sides 32, 34 of the cushion 12 correspond to one of the shorter sides of the rectangle and the lateral sides 36 of the cushion 12 correspond to the longer sides. The cushion 12 is located in relation to the patient's nose similarly to how it is located in the sample embodiment suited for children.

In another embodiment where the cushion 12 is square, the mask 10 is particularly suited for children and sides of the square are located in relation to the patient's nose similarly to how they are in the rectangular embodiments.

The cushion 12 may be integrally formed from silicone or foam by an injection molding process.

The cushion 12 includes an exhalation vent 72 in the form of two arrays 74 and 76 of apertures 78 disposed along respective curves. The apertures 78 in arrays 74 and 76 are near each other at a lower region 80 (the lowermost apertures 82 are spaced approximately 5 mm from each other) and diverge increasingly away from each other at an upper region 84 (the uppermost apertures 86 are spaced approximately 10 mm from each other). Each aperture 78 in a given one of the arrays 74, 76 is spaced from the other apertures 78 by approximately 5 mm. In this embodiment, eight apertures 78 are provided (four in each one of the arrays 74, 76) and the exit diameter of the apertures 78 is about 1.1 mm. This particular arrangement provides a vent flow that is particularly suitable for pediatric patient's and is easily manufacturable (i.e. apertures 78 in silicone are not too small).

In another sample embodiment about 16-26 holes are provided and each hole has an exit diameter of about 0.8 mm. In yet other sample embodiments, more apertures 78 may be provided of smaller exit diameters resulting in reduced noise. It should be appreciated that other known venting arrangements could be incorporated into the cushion 12 and support structure 14 of this mask 10.

The cushion 12 has a short, hollow cylindrical protrusion 88 extending from each of its lateral sides 36 for receiving an elbow 18 or plug 20. The hollow 90 of each protrusion 88 is in fluid communication with the air chamber 26 of the cushion 12. In this case, the dimensions of the hollows 90 are the same such that the elbow 18 or plug 20 can be fitted into either hollow 90. This allows the elbow 18 and air delivery tube 11 to connect to the most convenient side of the mask 10. With such an arrangement, the patient may lie on their stomach with their head facing to one side without occluding the air delivery tube. Additionally, a clear line of sight to the patient's nose is possible as there is no elbow or air delivery tube positioned on the front of the mask as with other breathing masks.

Advantageously, the mask 10 also provides a connection arrangement 100 between the cushion 12 and air delivery tube 11 that at least partially decouples movement of the tube 11 from the cushion 12 and support structure 14. This means that lateral and some axial movement of the tube 11 (e.g. from tube drag) and tube rotation do not substantially move the cushion 12. Subsequently, movement of the cushion 12 and support structure, or frame, 14 on the patient's face due to tube drag is reduced. This serves to reduce disturbance to the patient, particularly as it aids maintenance of the cushion seal with the patient's face.

The connection arrangement 100 comprises two parts: either of the cylindrical protrusions 88 and the elbow 18. The elbow 18 is releasably and rotatably connected to the cushion 12 and the air delivery tube 11. Each cylindrical protrusion 88 comprises an inner cylinder 96 and an outer cylinder 98 that are substantially concentric and joined at an end closest to the support structure 14 by a thin membrane 102. In the depicted sample embodiment, the thin membrane 102 is about 0.6 mm thick but it should be appreciated that this dimension could vary by up to 50% depending on the level of decoupling required. The desired and suitable dimension ranges for the inner and outer cylinders 96 and 98 are provided in Table 3 below.

TABLE 3

| | Desired Inside Diameter (mm) | Suitable Inside Diameters (mm) | Desired Outside Diameter (mm) | Suitable Outside Diameters (mm) |
|---|---|---|---|---|
| Inner Cylinder | 9.1 | 5-20 | 11.2 | 7-22 |
| Outer Cylinder | 13.1 | 9-21 | 15.3 | 11-26 |

By virtue of the flexibility and elastic properties of the thin membrane 102, the inner cylinder 96 can rotate laterally with respect to the outer cylinder 98, about the thin membrane 102, by a small angle, and also move axially with respect to the outer cylinder 98 by a small distance. In the depicted sample embodiment, the maximum angle of rotation is approximately 20° and an axial displacement of up to approximately 5 mm is possible. Thus, the inner cylinder 96 is substantially decoupled from the outer cylinder 98.

In the depicted sample embodiment, the thin membrane 102 is made from silicone, but it should be appreciated that it could be made from any other suitable material that is flexible and biocompatible.

The outer diameter of the elbow 18 forms a snug fit with the inner diameter of the inner cylinder 96. The inner cylinder 96 includes a circumferential rib 104 on its inner surface 106 that is configured to mate with a cooperating circumferential groove 108 disposed on the outer surface 110 of the elbow 18. Accordingly, when the elbow 18 is inserted into the soft inner cylinder 96 the rib 104 interlocks with the groove 108 to axially fix the elbow 18 in the inner cylinder 96. By virtue of the fact that the inner cylinder 96 is substantially decoupled from the outer cylinder 98, the elbow 18 and air delivery tube 11 are substantially decoupled from the cushion 12. In another sample embodiment, the rib 104 and groove 108 arrangement could be reversed (i.e. rib 104 on elbow 18, groove 108 on inner cylinder 96).

The free end of the outer cylinder 98 is angled towards the centre of the front side of the mask 10 so that a portion of the inner cylinder 96 extends beyond the end of the outer cylinder 98. This allows the inner cylinder 96 to laterally rotate towards the front side of the mask 10 to a greater degree since it is not blocked by the outer cylinder 98 to the same extent. This provides better decoupling of the tube 11 from the cushion 12. Another advantage is that this angle provides the mask with better aesthetics, in that the mask appears more streamlined to the face. The angle towards the center of the front side of the mask 10 is approximately 65° although angles in the range of 30°-85° would also be suitable and offer the same or similar advantage.

The decoupling mechanism is also supported by the support structure 14 since the outer cylinders 98 of the cushion 12 are snugly seated in respective, relatively rigid cylinders 112 provided in the support structure 14.

In another sample embodiment, two flaps made from resilient material (e.g. silicone) are provided at the cylindrical protrusions 88. The flaps are biased towards a closed position whereat they seal against the cylindrical protrusions 88 to block fluid communication between the air chamber 26 and the ambient air. Each flap is readily displaced to an open position by insertion of the elbow 18 to allow fluid communication with the air chamber 26.

Advantageously, in this sample embodiment, the plug 20 is redundant and therefore not required. The flaps can be provided at either end of the cylindrical protrusions 88 or inside the protrusions 88. The flaps may be between about 0.5-4 mm thick, for example approximately 2 mm thick.

Support Structure or Frame

Referring to FIGS. 47-57, the support structure 14 acts as an exoskeleton immediately adjacent the cushion 12. The support structure 14 has two wing portions 118 and an arched bridge 120 connecting the wing portions 118. The wing portions 118 are angled at about 45° to the plane defined by the front side 28 of the cushion 12. The wing portions 118 are approximately 45 mm long, 20 mm wide and 1.2 mm thick although it should be appreciated that in other sample embodiments these dimensions may vary up to 10%, up to 20% or up to 50% and still achieve the same or similar functionality. The arched bridge 120 is located substantially above the winged portions 118 and is approximately 38 mm long, 10 mm wide and 3 mm thick, although it should be appreciated that in other sample embodiments these dimensions may vary up 10%, up to 20% or up to 50% and still achieve the same or similar functionality. The wing portions 118 of the support structure 14 are flexible to provide support to a range of facial geometries.

In other embodiments the arched bridge 120 may also be arranged/molded in line with the cushion wing portions 118 or even substantially below the wing portions 118.

When patients sleep they often move around in bed (e.g. sleep on their stomach or side) and children sometimes sleep with their forehead to the bedding. In this case, a flexible mask without a support structure could collapse and potentially suffocate the child. Thus, one function of the support structure 14 is to stop the cushion 12 collapsing and thereby obstructing the patient's breathing.

Conversely, it is desirous that the mask 10 as a whole be very flexible and soft. Advantageously, this minimizes the mask pressure points on the child's face and assists a clinician or parent feel more comfortable with mask therapy as a whole (particularly in the case of children). Thus, the mask 10 has been designed to be as flexible as possible, while still providing enough support.

Another function of the support structure 14 is to connect the cushion 12 to the headgear. The support structure 14 may include rigid cylinders 112 on each side for receiving respective cylindrical protrusions 88 of the cushion 12. In use, the rigid cylinders 112 may be flexed outwardly to receive the cylindrical protrusions 88 and then released to mechanically lock the cushion 12 to the support structure 14. In one embodiment the cushion 12 can rotate with respect to the support structure 14 by virtue of the fact that the cylindrical protrusions 88 can rotate within the rigid cylinders 112. This rotation will allow the patient to have a greater range of movement without disrupting the seal of the mask. In the depicted embodiment, the inside and outside dimensions of the ring portions may be about 15.6 mm and 17.6 mm, respectively, although it should be appreciated that in other embodiments these diameters may vary between about 11 and 23 mm and between about 13 mm and 25 mm, respectively, or more and still achieve the same or similar functionality.

Advantageously, the support structure 14 has been designed to substantially isolate the cushion 12 from warping in shape under headgear tension. Thus, headgear tension only causes the cushion 12 to be seated more firmly on the patient's face.

The support structure 14 may be made of nylon but could also be made out of polypropylene or other suitable engineering material. The support structure 14 may be formed by an injection molding process.

The support structure 14 is significantly smaller and less bulky than in other masks, particularly due to the exoskeleton like appearance and lack of forehead support. This reduces the visual obtrusiveness and benefits clinician's, patient's and carer's perceptions of the therapy.

The support structure 14 may be water clear so that the patient nares can be inspected to ensure there are no obstructions to breathing. In other sample embodiments, the support structure 14 may be translucent or even transparent.

In one sample embodiment, the cushion 12 is overmolded onto the support structure 14 reducing mask assembly steps and manufacturing costs. In another embodiment, the support structure 14 could be formed as part of the cushion 12 either out of the same material or out of a different material. In one variation, the support structure 12 is also formed from silicone, albeit a silicone with more rigid material properties, and is formed by co-molding with the cushion 12. This reduces mask assembly steps and manufacturing costs. The cushion 12 may, in another sample embodiment, be formed with a pocket, recess or aperture that is adapted to receive the support structure 14. In yet another variation, the cushion 12 may be configured to receive a malleable or bendable wire such that the shape of the cushion 12 could be hand-molded to suit the patient's face. Advantageously, this may lead to a better seal and greater comfort.

In yet another sample embodiment, the part of the support structure 14 that transverses the front side 28 of the cushion 12 is higher up the cushion 12 or lower down the cushion 12 than in the depicted embodiment to achieve greater stabilization of a chosen area of the cushion 12. The support structure 14 may be configured so that upon connection to the headgear, the support structure is rotated upwards and in contact with the top of the cushion 12 directly, e.g. via a customizable or molded support structure 14, or indirectly, e.g. via a padding element or elements. As discussed in more detail below, the support structure 14 and the cushion 12 may be formed as a single piece, e.g. of silicone. As also discussed in more detail below, the support structure 14 and the cushion 12 may be relatively rotatably adjustable with respect to one another.

The use of the support structure 14 permits the use of a single cushion without the need for an undercushion. The single cushion is stabilized by the wings 118 of the support structure 14, and permit the single cushion to form a compliant seal. The support structure 14 also permits the cushion to be lightweight, thinner than currently used cushions, and prevents the cushion from being collapsed in use, e.g. if the patient sleeps facing a pillow. The provision of, for example, the cheek pads, the design of the thickness of the cushion, in combination with the support structure 14 prevents excessive forces from being applied to the cushion.

Relatively Rigid Members to Support Structure Connection

The connection mechanism 138 depicted in FIGS. 20, 21, and 58a-58c includes a male portion 164 extending forwards from each of the lateral frame wings 118. The male portions 164 are configured to mechanically interlock with a respective cooperating female portions 166 defined by the relatively rigid members 22. Each male portion 164 comprises a body 168 and a cooperating rounded trapezoidal lug 170 extending from the body 168, the lug 170 having a body portion 172 and a lip 174 overhanging at least a portion of the body portion 172. The lug 170 is approximately 13.2 mm long, 5.9 mm wide and 1.8 mm deep. The lip 174 overhangs the body portion 172 by approximately 0.35 mm.

The female portion 166 of the connection is formed in the respective thin, plate-like relatively rigid members 22 and has a rounded trapezoidal aperture 176 that is sized and shaped to cooperate with the rounded trapezoidal lug 170. In use, when the lip 174 of the lug 170 is inserted through the aperture 176 in the relatively rigid members 22 and the male portion 164 is pulled towards the tip 178 of an arrow head shape formed by the shape of the lug 170, an edge of the aperture 180 locates between an under-surface 182 of the lip 174 and the body 168 of the male portion 164 to form a releasable connection. In order to release the connection, the male portion 164 is pulled away from the tip 178 and the lug 170 is removed from the aperture 176.

Advantageously, this headgear to frame connection 138 is unique, inexpensive, intuitive, easy for both a patient and third party to connect and disconnect, smaller and less bulky, and less fiddley than those connections provided on prior art mask arrangements. This connection is particularly adapted for easy connection and disconnection by a clinician and by children. This is particularly helpful in the treatment of pediatric patients.

It should be noted that in other sample embodiments the rounded trapezoidal lug 170 may be a substantially triangular lug or another trapezoidal variant and the rounded trapezoidal aperture 176 may be a substantially triangular aperture or another trapezoidal variant. It should also be appreciated that a differently sized connection could be provided, for example if larger, to increase ease of use, and for example if smaller, to increase unobtrusiveness.

In another sample embodiment, the rounded trapezoidal aperture 176 includes an enlarged area at its narrow end (so the aperture is shaped like a keyhole) and the trapezoidal lug 170 includes a cooperating rib at its narrow end. This structure allows the lug 170 to lock into the aperture 176 by pressing the rib into the enlarged area of the aperture (i.e. a detent style lock).

Elbow

Referring to FIGS. 59-63, the elbow 18 also includes a circumferential extrusion 114 around its outer surface 116 to act as a mechanical stop to prevent the elbow 18 from sliding right through the inner cylinder 96 and into the air chamber 26 formed by the cushion 12. The circumferential extrusion 114 may have a diameter that is 1 mm greater than the diameter of the elbow 18, but may be up to 2 mm greater than the diameter of the elbow 18 and the same or similar benefit achieved.

The bend in the elbow 18 is approximately 30°. In other sample embodiments the bend may be about 5-90°, depending on the particular tubing arrangement and location required. The other end of the elbow 18 is adapted for connection with a short tube. The elbow 18 connects to the tube by a snap-fit. The advantage of the rotatable elbow 18 is that tube drag is reduced.

The cushion inlet is arranged at the side of the cushion 12 to reduce visual obstruction and allow the patient to sleep with their forehead resting on the bedding as infants and children sometimes do. In other variants, the elbow 18 is connected to the front side 28 of the cushion 12.

Plug

Referring to FIGS. 3, 4 and 64-68, a plug 20 may be provided and is sized for insertion into one of the inner cylinders 96. The plug 20 comprises a body 198, a head 200 and a groove 202. The head 200 prevents the plug from being pushed through into the air chamber 26 and has a diameter of about 11.6 mm, which is larger than the diameter of body 198, which is about 9.2 mm. The groove 202 is analogous in function to the groove 108 provided by the elbow 18 and serves to lock the plug 20 in the cushion 12. The groove 202 may have a diameter of about 8.4 mm. The plug 20 also includes a front portion 204 directly adjacent the groove 202 that has a diameter of about 9.8 mm. The larger diameter of the front portion 204 with respect to the diameter of the plug body 198 helps retain it on the other side of the cushion rib 104 in use and thus aids in the retention of the plug 20 in the inner cylinder 96. The plug may be about 13.8 mm long. It should appreciated that all these dimensions may vary with changes in the dimensions of the cylindrical protrusions 88.

The plug 20 is used in the inner cylinder 96 opposite that which the elbow 18 is connected to and serves the purpose of preventing excessive venting. This, in turn, allows pressure to build up in the mask system 10 and effective therapy to be delivered to the patient.

Relatively Rigid Members

Referring to FIGS. 3, 4, 69 and 70, each of the relatively rigid members 22 (otherwise known as the "headgear yokes" or "reinforcing structure" or "rigidizer") include a forward finger 130, an upper finger 132 and a lower finger 134. Most of each rigid member 22 overlies a forward portion 136 of the headgear 16 to provide a level of rigidity or reinforcement to the headgear 16. This increased rigidity stabilizes the mask 10 on the patient's face providing a more stable and continuous seal. This stabilization helps maintain the mask 10 and headgear 16 at a correct and comfortable location on the patient's face and head avoiding known pressure points. The increased rigidity also helps maintain the mask 10 out of the patient's field of vision. Connection of the rigid members 22 by the support structure 14 synergistically increases the total level of stabilisation of the mask on the patient's face. All of these factors contribute to the patient's experience of the mask system and therapy, which aids compliance with their therapy.

The forward finger 130 is located approximately mid-way between the patient's eyes and mouth in the height direction or in line with the bottom of the patient's nares. Advantageously, therefore, it is substantially removed from the patient's field of vision.

The forward finger 130 extends rearward to a position approximately 2-4 cm from the patient's ear depending on the age and size of the patient. The length of the forward finger 130 may be about 43 mm in the depicted sample embodiment. In other sample embodiments, this length may be between about 20 mm and 70 mm. The width of the forward finger 130 may be about 10 mm in the depicted sample embodiment. In other sample embodiments, this width may be between about 8 mm and 30 mm. The forward finger 130 includes part of a connection mechanism 138 at its forward end 140 for attachment to the support structure 14. This connection mechanism 138 is discussed in greater detail in a subsequent section.

The upper finger 132 branches upwards from the rear end 142 of the forward finger 130 and may be configured so that it substantially avoids the patient's field of vision. A rear end 144 of the upper finger 132 of each member 22 is located above the patient's respective ear. The upper finger 132 is angled upwards from the forward finger 130 by an angle of approximately 45°. In other sample embodiments, the angle may be between about 30°-60°. In the depicted sample embodiment, the upper finger 132 may be about 77 mm. In other embodiments, this length may be between about 50 mm and 100 mm. The width of the depicted upper finger 132 may be about 8 mm, but may be between about 5 mm and 30 mm. The rear end 144 of the upper finger 132 is angled rearwards so that is approximately parallel with the forward finger 130.

The lower finger 134 branches downwards from the rear end 142 of the forward finger 130 and may be configured so that it has a rear end 146 located below the patient's respective ear lobe, and desirably below the sensitive region. The lower finger 134 is angled downwards from the forward finger 130 by an angle of approximately 60°. In other sample embodiments, this angle may be between about 30°-90°. In the depicted sample embodiment, the lower finger 134 may be about 33 mm long. In other sample embodiments, this length may be between about 20 mm-50 mm. The width of the depicted lower finger 134 may be about 9 mm, but may be between about 5 mm-30 mm. The rear end 146 of the lower finger 134 is angled rearwards by about 30°.

The rear end 146 of the lower finger 134 includes an aperture 160 for receiving a lower headgear strap.

The thickness of each member 22 may be about 0.8 mm in the depicted sample embodiment. This thickness provides a high degree of flexibility in out-of-plane bending and in torsion, but a low degree of flexibility in in-plane bending. In other sample embodiments, the thickness may be between about 0.6 mm-1 mm, which provides the above advantages but maybe not to the same extent, or between about 0.4 mm-2 mm, which provides these advantages, at least to a degree.

In this sample embodiment, the members 22 may be made from nylon, but in other sample embodiments may be made from polypropylene or any other suitable engineering material. The members 22 may also be made of silicone for a high degree of softness and flexibility creating comfort for the patient. The material that the relatively rigid members 22 are made out of is thin enough to be able to be die-cut. This manufacturing process is cheaper and more time efficient that injection molding of mask components. The relatively rigid members 22 can also be formed by an injection molding process.

It should be appreciated that any of the above dimensions could be altered by up to 5%, by up to 10% or by up to 20%.

In one variation the relatively rigid members 22 and the support structure 14 are formed in one piece. This removes an assembly step leading to a reduction in the cost of goods. In this case, the headgear 16 may be formed such that it is releasably connectable to the rigid members 22 (e.g. via a clip). In another variation, the rigid members 22 and cushion support structure 14 could be overmolded providing similar benefits. However, it should be appreciated that the support structure 14 and the rigid members 22 may be formed separately and connected, for example by adhesive.

Headgear

Referring to FIGS. 71-74, the headgear may comprise a forward portion 136 that underlies the relatively rigid members 22, an upper strap 152, a middle strap 154 and a lower strap.

The forward portion 136 underlies the upper and lower fingers 132, 134 of the relatively rigid members 22, as well as a portion of the forward finger 130, but it stops short of the headgear-to-frame connection mechanism 138. The forward portion 136 is also wider than the relatively rigid members 22. In the depicted sample embodiment, forward portion 136 may be about 16 mm wide, which may be about 3-5 mm wider than the relatively rigid members 22. This reduces or cancels the lines of pressure associated with the edges of the relatively rigid members 22. The greater width also aids the distribution of headgear tension onto the face and therefore aids in avoiding discomfort and pressure sores. In other sample embodiments, the headgear 16 may be wider than the relatively rigid members 22 by between about 1 mm and 20 mm. The wider embodiments provide even greater pressure distribution that might be suitable for a patient with very sensitive skin.

Figure 67:
FIG. 67 schematically depicts an end view of the plug of FIG. 64.
Figure 68:
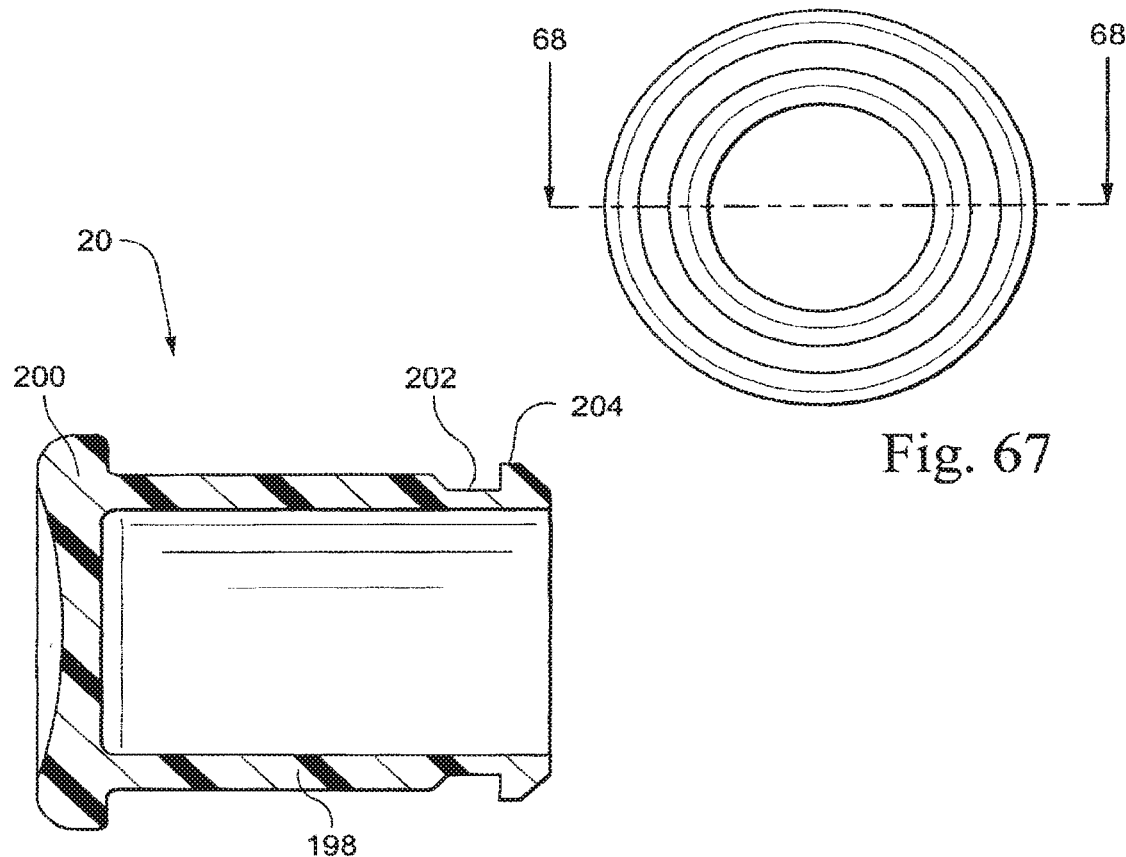
FIG. 68 schematically depicts a cross-sectional view through Section 62-62 of FIG. 67.
Figure 71:
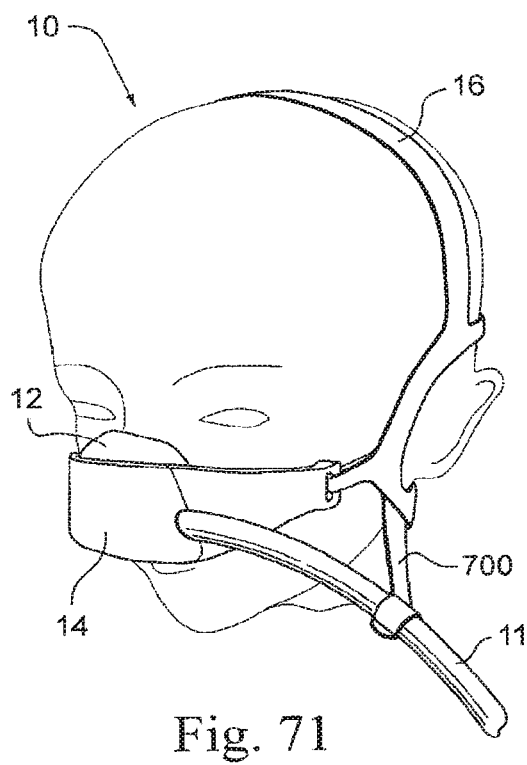
FIGS. 71-74 schematically depict various tube routing arrangements according to further embodiments of the present invention.
Figure 72:
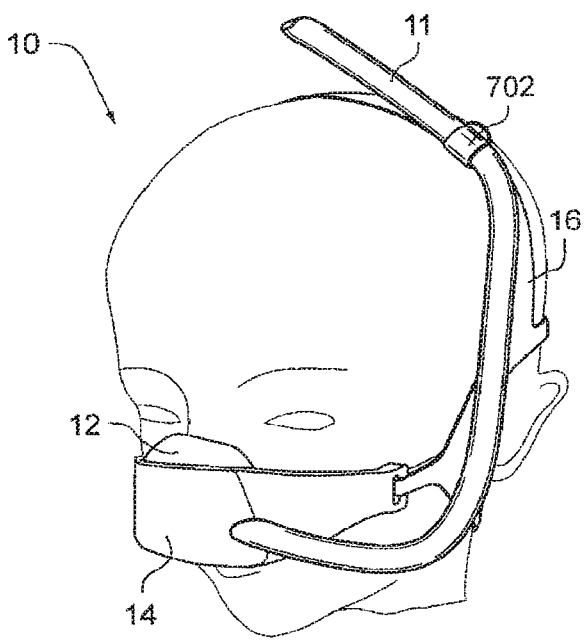
Figure 73:
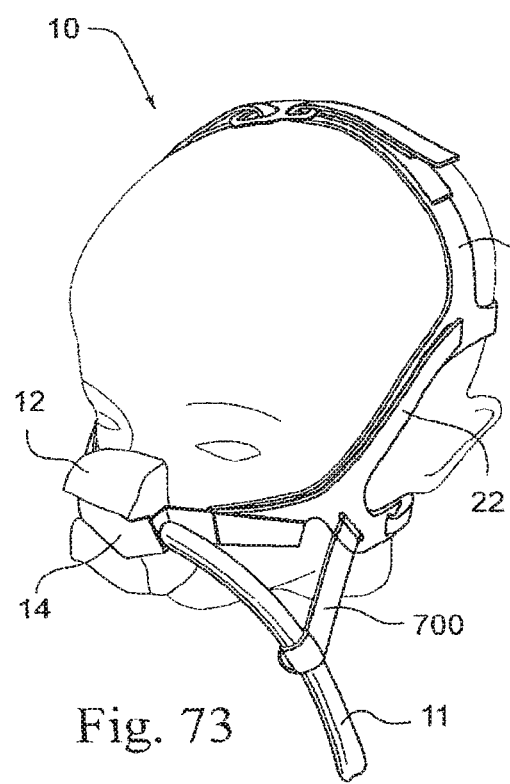
Figure 74:
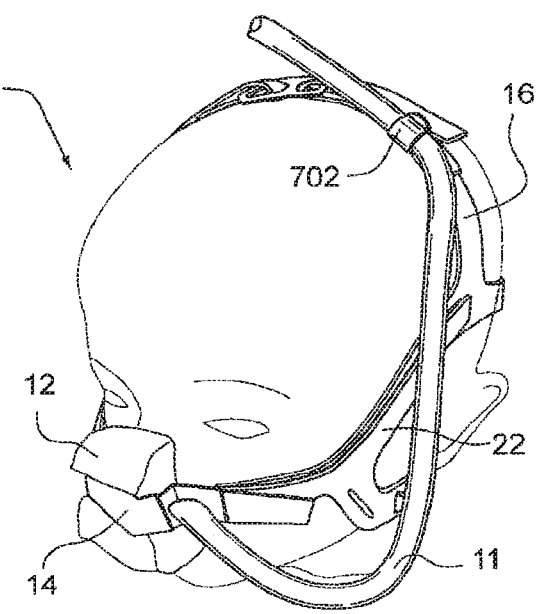

The upper strap 152 branches upwardly from the forward portion 136. The angle subtended between the upper strap 152 and the middle strap 154 may be approximately 75°. This locates the upper strap 152 over the top of the patient's head above the occiput, but behind the bregma. Under headgear tension this allows the upper strap 152 to apply a force to the mask 10 having an upward and rearward component. In other sample embodiments, the angle may be between about 75°-90°, which provides a greater upward force component to the mask 10. In yet other sample embodiments, the angle may be between 75°-45°, which provides a greater rearward force component to the mask. The upper ends 158 of the upper straps 152 maybe connected by a ladder-lock style buckle 180 as shown in FIGS. 67 and 68, as the rear ends of the lower straps may be (not shown). As shown in FIGS. 71 and 72, the headgear 16 may be attached to the support structure 14 without the rigid members 22. As shown in FIGS. 71 and 73, the tube 11 may be supported by a support strap 700 that is attached to the headgear strap (FIG. 71) or the rigid member (FIG. 73) at a side of the patient's face. As shown in FIGS. 72 and 74, the tube 11 may be supported by a support strap 702 that is attached to the headgear 16 at a region toward the side of the top of the patient's head. These configurations may distribute some of the load on the tube (e.g. tube drag) from the support structure 14 to the headgear 16.

In this sample embodiment, the headgear 16 is made of a flexible foam and fabric composite called BREATHOPRENE™, which is manufactured by Accumed. In another sample embodiment, the headgear 16 may be made from foam, and in another, from foam adhered to a thin plastic. In both of the above sample embodiments the headgear 16 is, relative to many prior art masks, extremely soft resulting in high levels of patient comfort. This is especially advantageous for young children who have very soft skin.

In the depicted sample embodiment, the headgear 16 may be about 2.5 mm thick. However, the headgear 16 may also be very thin in the thickness direction. This may provide greater comfort and unobtrusiveness. Some advantage can be achieved by headgear 16 that varies up to 20% or up to 50% from these dimensions.

Another advantage of the headgear 16 of the sample embodiments is that it does not incorporate hard buckles at the back or top of the head. Such buckles can cause significant discomfort to patients.

The headgear 16 and relatively rigid members 22 provide a high level of stability to the cushion 12 and mask 10. This aids in maintaining a continuous seal resulting in more effective therapy and a higher level of patient comfort.

The headgear 16 material may also incorporate different colors, decals, themes or cartoon characters that can be particularly effective in encouraging pediatric patient compliance. Example themes are a space theme and a dinosaur theme.

It should also be appreciated that in the sample embodiments of FIGS. 73 and 74, the rigid members 22 and the support structure 14 may be formed as one piece instead of using, for example, the connection mechanism described above with respect to FIGS. 58a-58c. The headgear 16 may instead include a release mechanism, e.g. a quick release clip, between the lower strap of the headgear 16 and the rigid member(s) 22.

The headgear 16 may comprise a lower strap, e.g. extending around the back of the patient's head beneath the patient's ears that creates appropriate force vectors that create appropriate sealing forces for the cushion, in particular for an over-the-nose type cushion described herein. The force vectors provided by the lower strap rotate the top of the cushion into the patient's nasal bridge to pull the cushion directly into the face.

Tubing

Figure 75A:
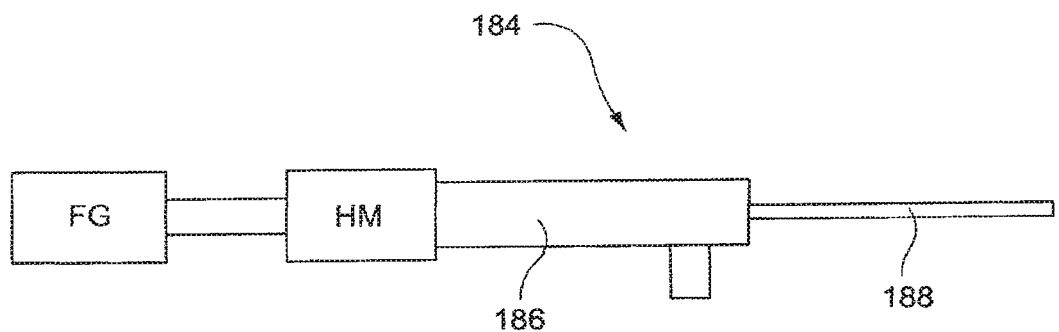
FIGS. 75a and 75b schematically depict two different tubing arrangements connected to a flow generator and humidifier according to further sample embodiments of the present invention.

Referring to FIGS. 75a-76b, various tubing arrangements are shown. One tubing arrangement 184 depicted in FIG. 75a is connected to a flow generator FG via a humidifier HM. This arrangement comprises either a 15 mm or 19 mm diameter tube 186 of about, for example 2 m in length, connected to and in fluid communication with a tube 188 that may have a diameter of, for example about 6-8 mm, for example 7 mm, and a length of about, for example, 3 m.

Figure 75B:
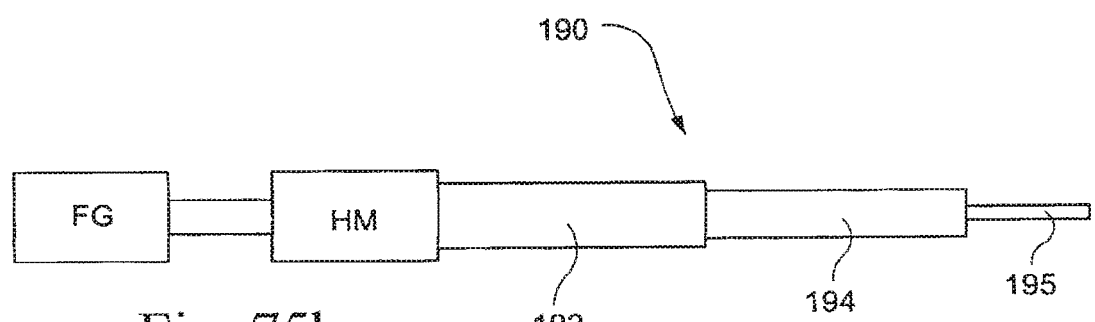
Figure 76A:
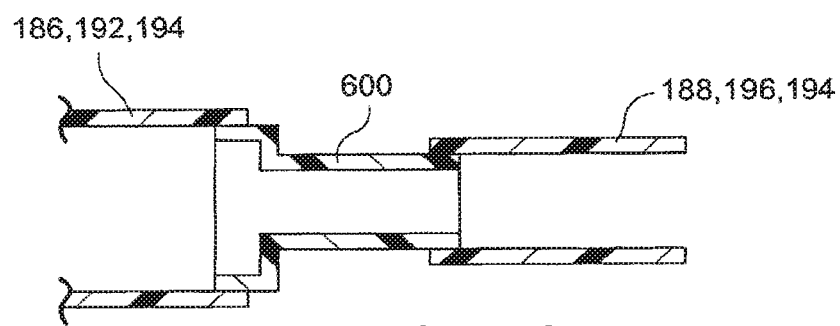
FIGS. 76a and 76b schematically depicts a two different couplings for the tubing arrangements according to further sample embodiments of the invention.
Figure 76B:
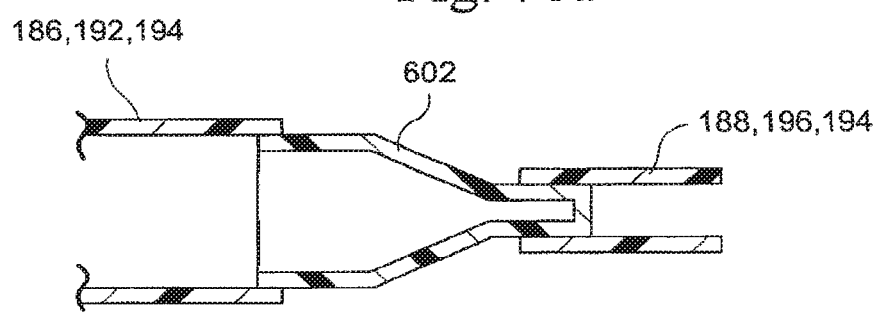

Another tubing arrangement 190 is depicted in FIG. 75b and is three-staged and may include a 1 m length of 19 mm tube 192, a 1 m length of 15 mm tube 194 and a 1 m length of 6-8 mm, for example 7 mm, tube 196. Either or both of tubes 192 and 194 may be connected to a bed head or other stable surrounding object via a clip or clamping mechanism (e.g. a spring clamp). Tube 196 may be a 7 mm diameter tube, about 300 mm in length which is attached to the headgear 16 via a clip to stabilize the tube 196. The 8 mm tube is advantageous in that it locates fairly close to the patient's face and so is visually unobtrusive. As shown in FIGS. 76a and 70b, the tubes 186, 188 and 192, 194, 196 may be connected using connectors 600 or 602, respectively. As shown in FIG. 76a, the connector 600 provides a sharper transition between tubes, whereas as shown in FIG. 76b, the tapered connector 602 provides a more gradual transition between tubes.

In another sample embodiment, a tapered tube is provided that is between 1 and 4 m in length and tapers from a diameter of about 15 mm or 19 mm at the flow generator or humidifier end down to a diameter of about 6-8 mm, for example about 7 mm, at the patient interface end. The tapering down in diameter may be linear or in another version only occur near the mask 10.

These sample embodiments are particularly suitable to pediatric use where smaller tidal volumes are involved. For example, in an adult mask, the flow generator may provide a flow of about 70 l/min, and the mask may vent about 30 l/min. However, in a mask configured for treatment of an infant or child, the flow generator may be configured to generate a flow of approximately 12-15 l/min. The vent in such a mask configured for an infant or child may be configured to vent flow in an amount equal to, or less, than a mask configured for an adult. It should be appreciated that any of the above dimensions may vary depending on the particular mask system and patient arrangement. For example, the particular tubing diameter may be selected to best suit child breathing dynamics. The tubing, including any or all of the individual tubing, may be configured as retractable tubing such as disclosed in U.S. Applications 60/973,902, file Aug. 29, 2007, and 60/987,825, filed Nov. 14, 2007, the entire contents of both being incorporated herein be reference. The use of retractable tubing would provide further decoupling of the support structure or frame from tube drag.

It should also be appreciated that the flow generator may also be configured to provide instantaneous adjustments to the flow.

Bonnet Headgear

Figure 77:
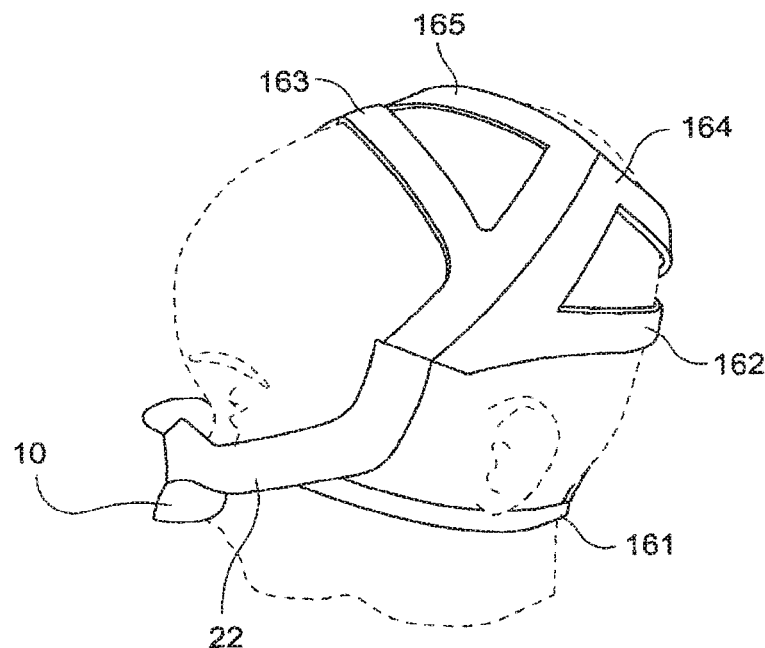
FIGS. 77-81 schematically illustrate a mask according to another sample embodiment of the invention.
Figure 78:
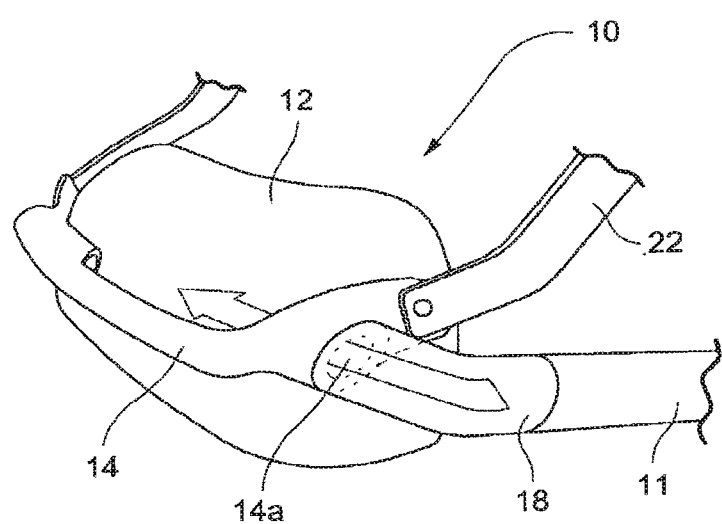
Figure 79:
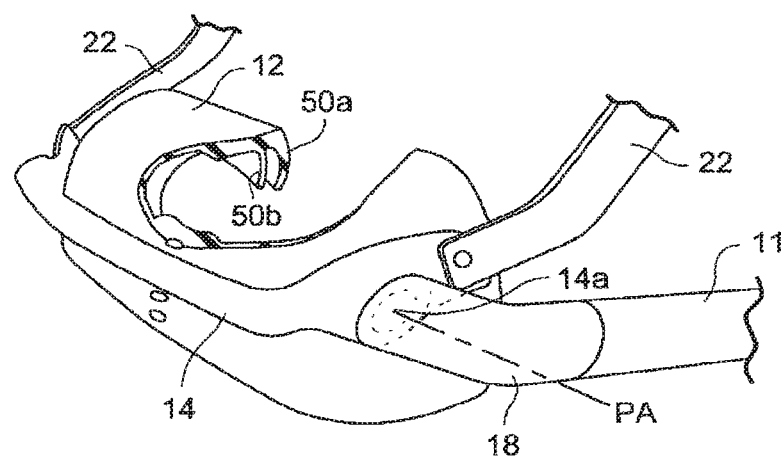

Referring to FIG. 77, a headgear according to another sample embodiment of the invention includes a "bonnet" that is configured to engage the top and back of the patient's head. A "bonnet" style headgear configuration may be more familiar to parents and thus make them feel at ease with their child's respiratory therapy. The mask 10 may be connected to the headgear 16 by a rigid member, or stiffening element, or rigidizer, 22. The headgear 16 may include a lower strap 161 connected to the stiffening element 22 that is configured to extend around the back of the patient's head below the ears. The headgear 16 may also include an upper strap 162 that is configured to extend around the back of the patient's head above the patient's ears. The headgear 16 may further include a top strap 163 that is configured to extend across the top of the patient's head. The upper strap 162 and the top strap 163 may be connected to a side strap 164 that extends from the stiffening element 22. A second top strap 165 may extend from the end of the side strap 164 and encircle the back of the patient's head.

Slim Support Structure or Frame with Adjustable Cushion

Referring to FIGS. 78-81, a mask 10 according to another sample embodiment of the invention may include a frame or support structure 14 and a cushion 12 that is supported by the frame or support structure 14. The frame 14 may be connected to, or formed in one piece with, a rigid member, or stiffening element, or rigidizer, 22 for connection of the mask 10 to a headgear system. An air delivery tube 11 may be connected to the frame or support structure 14 for delivering a pressurized flow of breathable gas to the cushion 12. The air delivery tube may be connected to an elbow 18 that is connected to the frame 14 for delivery of the flow of pressurized breathable gas into the cushion in a manner similar to that disclosed above.

Figure 80:
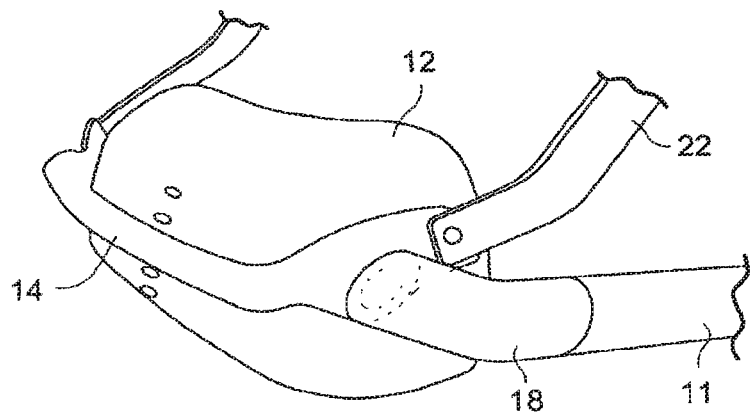

As shown in FIG. 80, the cushion 12 is rotatably supported on the frame 14 for pivoting engagement with the face of the patient. The cushion 12 is pivotably supported by the frame 14 for rotation about a pivot axis PA (FIG. 79) that is generally coincident with or parallel to the axis of an opening 14a formed in the frame 14 for receiving the elbow 18. The cushion 12 includes a hole (not shown) in communication and/or aligned with the hole 14a in the frame for receipt of the flow of pressurized breathable gas. For example, the frame 14 may include a cylindrical boss extending from the hole 14a that is received in the hole of the cushion 12. It should also be appreciated that the frame 14 may have a hole 14a on each side for receipt of an elbow 18 and/or a delivery tube 11, in which case the cushion would include a corresponding hole on each side.

Figure 81:
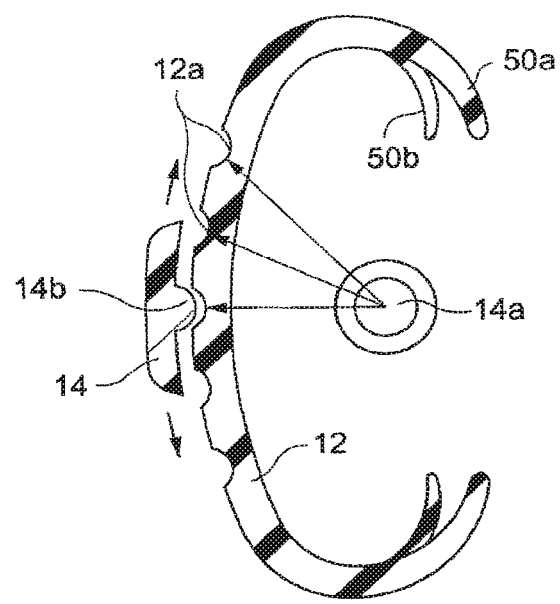

Referring to FIG. 81, the position of the cushion 12 may be adjusted with respect to the frame 14 by the adjustment of a seat or indentation 12a formed in the outer surface of the cushion 12 with respect to a projection 14b formed on an inner surface of the frame 14. It should be appreciated, however, that the cushion may be provided with a plurality of projections and the support structure or frame 14 may be provided with a recess configured to receive one of the projections on the cushion. The indentations or seats 12a are formed generally equidistant from the axis of the opening 14a in the frame 14 so that the adjustment of the position of the cushion 12 with respect to the frame 14 does not change the distance of the membrane 50 of the cushion 12 from the face of the patient. It should be appreciated that other adjustment mechanisms, for example one utilizing friction between the cushion 12 and frame 14, may be used. The adjustment of the cushion 12 with respect to the frame 14 allows the membrane to be moved higher or lower on the bridge of the patient's nose and the bottom portion of the membrane to be moved higher or lower with respect to the top lip of the patient. This means that the invention may fit a larger proportion of patients.

Full Support Structure or Frame

Figure 82:
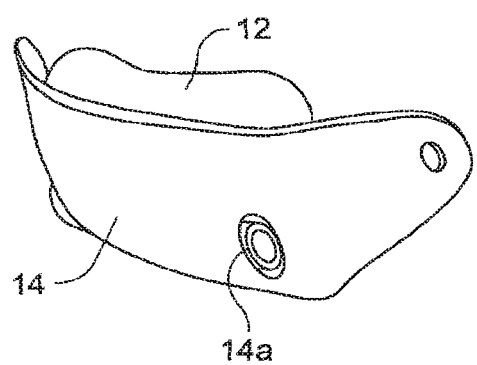
FIG. 82 schematically depicts a mask according to another sample embodiment of the invention.

Referring to FIG. 82, the frame 14 may be provided to extend around the sides of the cushion 12 so that provision of a stiffening element is not necessary for connection to the headgear system. It should be appreciated, however, that a stiffening element (or padded material thereof) may also be provided to contact, for example, the cheeks of the patient, when connecting the frame 14 and cushion 12 to the headgear 16.

Full Support Structure or Frame with Adjustable Cushion

Figure 83:
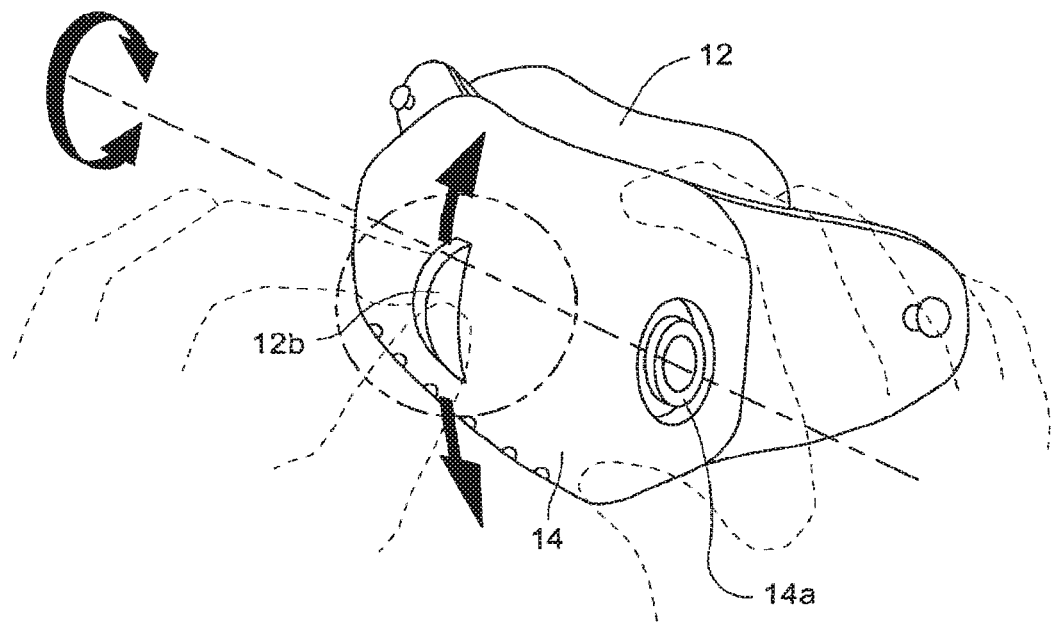
FIGS. 83-85 schematically depict a mask according to another sample embodiment of the invention.
Figure 84:
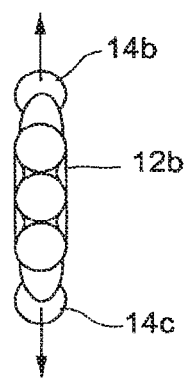
Figure 85:
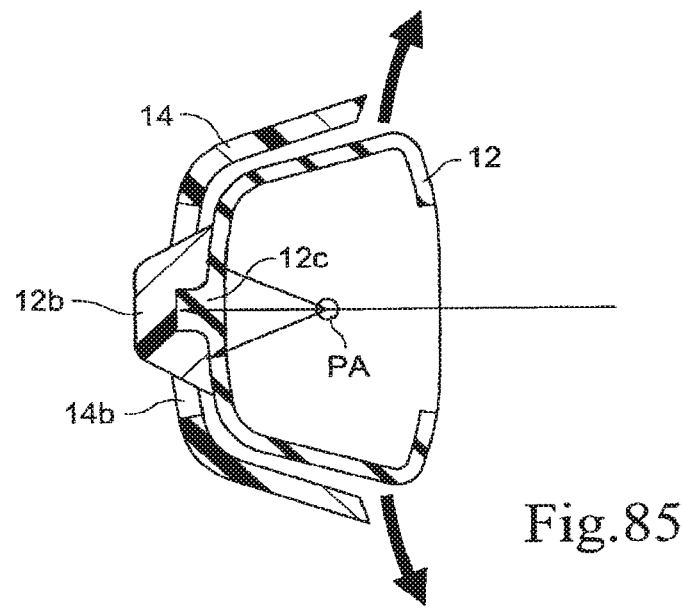
Figure 86:
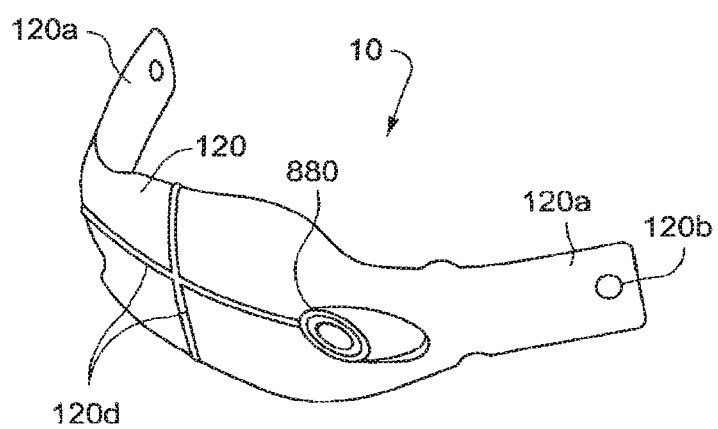
FIGS. 86-91 schematically depict a mask according to another sample embodiment of the invention, wherein FIG. 86 schematically depicts a front perspective of the mask, FIG. 87 schematically depicts the mask connected to a headgear system by a rigid element, stiffening element, or rigidizer, FIG. 88 schematically depicts a rear perspective of the mask, FIG. 89 schematically depicts a front elevation view of the mask, FIG. 90 schematically depicts a side elevation section view of the mask, and FIG. 91 schematically depicts a plan section view of the mask.

As shown in FIGS. 83-85, the cushion 12 may comprises an adjustment member 12b that is connected to a mount 12c provided on the cushion 12. The adjustment member 12b is received in a slot 14b provided in a front face of the frame 14. The position of the cushion 12 with respect to the frame 14 may be adjusted by pivoting the adjustment member 12 about the pivot axis PA. As shown in FIG. 84, the slot 14b in the frame 14 may include a plurality of positional indentations 14c that engage the sides of the adjustment member 12b to maintain the position of the cushion 12 in a selected position. The adjustment member 12b may be made of resilient material, e.g. the same material as the cushion 12, to permit the indentations 14c to engage the sides of the adjustment member 12 to maintain the position of the cushion 12. The indentations are configured to engage the adjustment member 12 in a frictional engagement sufficient to prevent the cushion from pivoting while engaged with the patient's face, but to permit pivoting of the cushion when the adjustment member is grasped by the user, or a clinician. The position of the cushion 12 may be changed by the user, or a clinician, by grasping the exposed adjustment member 12b, as shown in FIG. 83, and moving the adjustment member in the direction shown by the double headed arrow. Such adjustment means the mask is likely to fit more patients, and fit these patients more comfortably due to the greater level of fine-tuning.

One Piece Soft Cushion

Figure 87:
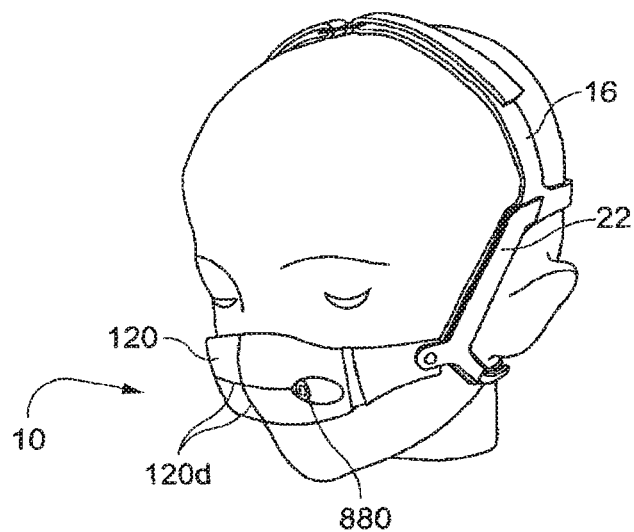

Referring to FIGS. 86-91, a mask 10 according to another sample embodiment of the invention may be formed of a one piece silicone cushion 120. As shown in FIG. 87, the cushion 120 may include two air delivery tube connectors 880 comprising cylindrical projections extending from a surface of the cushion 120. An elbow may be connected to the connectors 880 for connection to a delivery tube or conduit that delivers the flow of pressurized breathable gas to the patient. It should also be appreciated that only one connector 880 may be connected to an elbow and/or delivery tube and the other connector 880 may be plugged in a manner similar to that disclosed above. It should also be appreciated that the cushion 120 may be formed with only one connector 880. The cushion 120 maybe connected to a rigid element, or stiffening element, or rigidizer 22 for connection to a headgear system 16.

Figure 88:
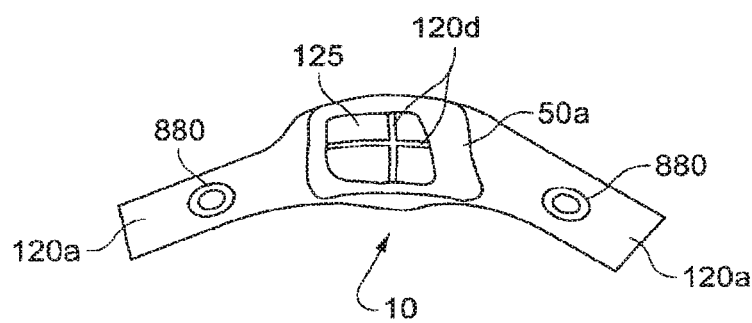
Figure 89:
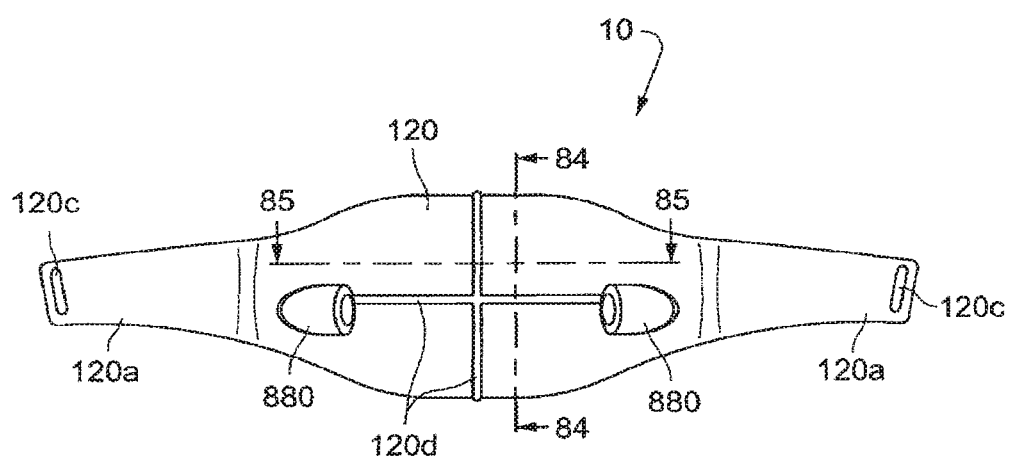
Figure 90:
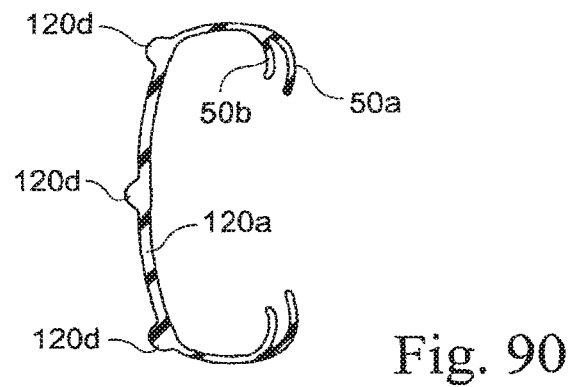
Figure 91:
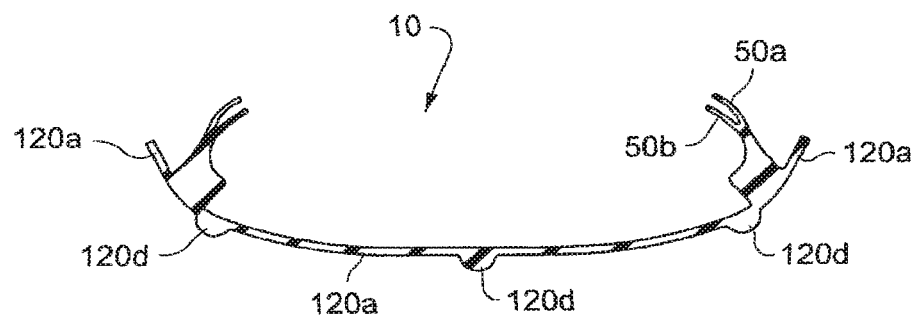

As shown in FIGS. 86, 87 and 89-91, a cross rib 120d may be provided on a front surface of the cushion 120. The cross rib 120d helps to maintain the mask structure when tension is applied to the ends 120a of the cushion 120. As shown in FIGS. 88-90, the cushion 120 may be a dual membrane structure, including a first membrane 50a and second, inner membrane 50b, although it should be appreciated that the cushion may include any number of membranes. The membrane, or membranes, surround a breathing cavity 125 defined by the mask/cushion.

Throughout a particular age group, a plurality of anthropometric variations may exist. It is difficult to provide a cushion geometry that will suit all of the anthropometric variations within an age group. The mask/cushion of FIGS. 86-91 may be advantageous as it provides a low facial deformation risk. The mask/cushion is also comfortable, light and may be formed smaller in size than conventional masks. The mask/cushion of FIGS. 86-91 also does not include any rigid parts, and thus does not pose any choking hazards to infants who may be fitted with the mask/cushion. The mask/cushion is also of simple construction as it is formed of a single piece, e.g., of soft and flexible silicone, and is unobtrusive when fitted on an infant or neo-natal patient. The mask 10 of FIGS. 86-91 also has friendly aesthetics.

The mask/cushion of FIGS. 86-91 may also be made available in different sizes. It has been found that the height of the bony part of an infant's nose corresponds to the infant's height. Accordingly, the appropriate mask size may be determined by examining the infant's height. In contrast, in adults the appropriate mask size is determined on the basis of the adults actual facial dimensions.

The mask/cushion may be made of 100% LSR or at least a rubber-like substance, for example, soft silicone. As shown in FIGS. 86-91, the mask/cushion does not have headgear clips so the mask/cushion may be made relatively soft and comfortable on the patient. The material forming the mask/cushion may also be transparent to allow a clinician to view the nares of the patient.

The mask/cushion of FIGS. 86-91 may also be used to provide CPAP or ventilation treatment to an infant or neo-natal patient. It should also be appreciated that the mask/cushion of FIGS. 86-91 may be formed as a nasal mask or as a full face mask.

As shown in FIGS. 86-91, the mask/cushion may be formed with a flatter profile than a conventional mask as it has been found that a child's nose does not project much more than beyond their forehead. The mask/cushion may be made of a thin membrane and the membrane may be thin enough so that it conforms to the infant or neo-natal patient's nose and reduces dead space.

The area of an infant's or neo-natal's face that are sensitive to pressure are also different than those on an adult's face. On an infant or neo-natal patient, it is acceptable to apply some pressure to the region between the bottom of the child's nose and their mouth, which would not be acceptable in adult patients. Moreover, the mask/cushion may be formed with areas of different softness, for example, by changing the thickness of the material or including gel or foam portions. The areas of pressure in use can be located at the most suitable parts of the infant's or neo-natal patient's face.

In addition, or as an alternative, to the cross ribs 120d shown in FIGS. 86-91, it should also be appreciated that the mask 10 may be formed so that certain portions of the frame 14 and the cushion have thicker sections to improve or provide rigidity to the mask/cushion.

One Piece Soft Cushion Headgear Connection Systems

Figure 92:
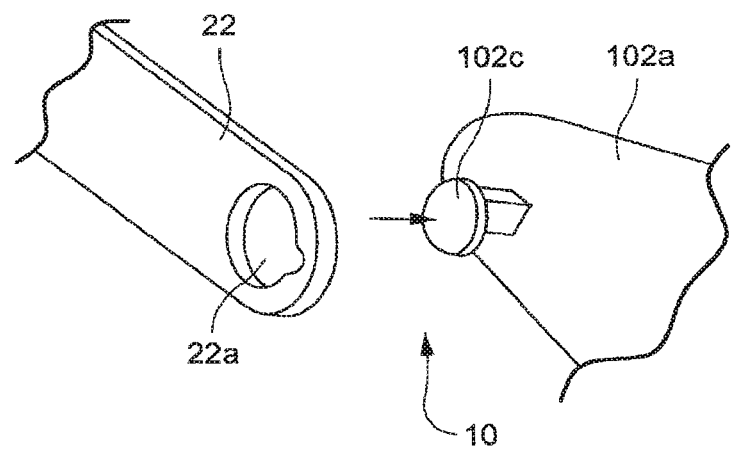
FIG. 92 schematically depicts an attachment system according to a sample embodiment of the invention.
Figure 93:
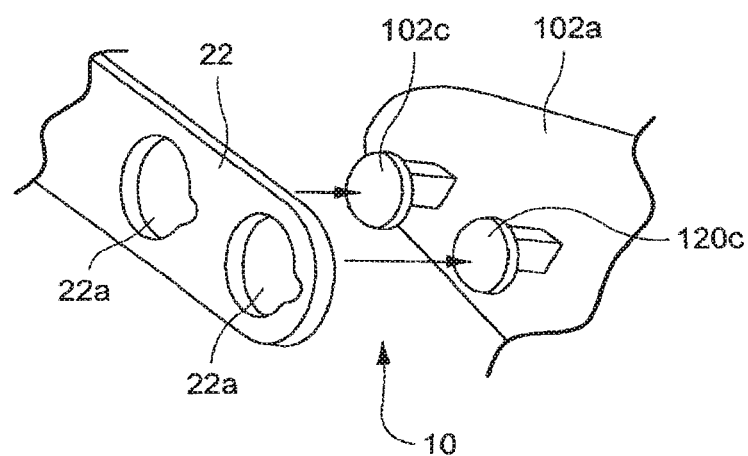
FIG. 93 schematically depicts an attachment system according to another sample embodiment of the invention.

Referring to FIG. 92, a headgear connection system for the mask/cushion may include a single projection 120c on each end of the cushion 120 that is received in a corresponding aperture 22a in a rigid member, or stiffening element, or rigidizer 22. According to another sample embodiment of the invention shown in FIG. 93, the attachment system may comprise two projections 120c on each end 120 of the cushion that are received in corresponding apertures 22a, in the rigid member, or stiffening element, or rigidizer 22. As shown in FIG. 92, some relative rotation between the cushion 120 and the stiffening element 22 may be permitted by the engagement of the projection 120c in the aperture 22a. However, in the embodiment shown in FIG. 93, the engagement of the two projections 120c a in the apertures 22a prevents relative rotation between the cushion 120 and the stiffening element 22.

Figure 94:
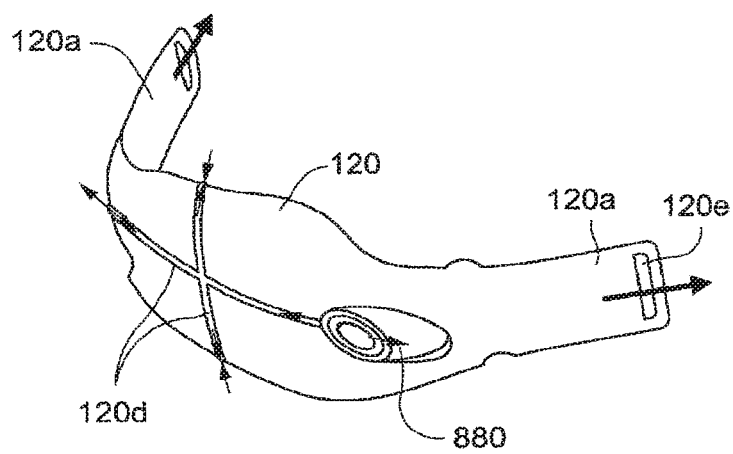
FIG. 94 schematically depicts mask comprising an attachment system according to another embodiment of the invention.

Referring to FIG. 94, the headgear connection system for the cushion 120 may comprise a slot 120e on each end 120a of the cushion 120. A rigid member, or stiffening element, or rigidizer may be connected to the slot 120e. For example, the stiffening element may include a hook that engages the slot 120e. The slots 120e of the cushion 120 may also directly receive a looped end of a strap of the headgear system.

Such additional headgear connection systems are designed to allow easier connection of the headgear to the patient interface, particularly by a third party.

Elbow and/or Tube Connection

Figure 95:
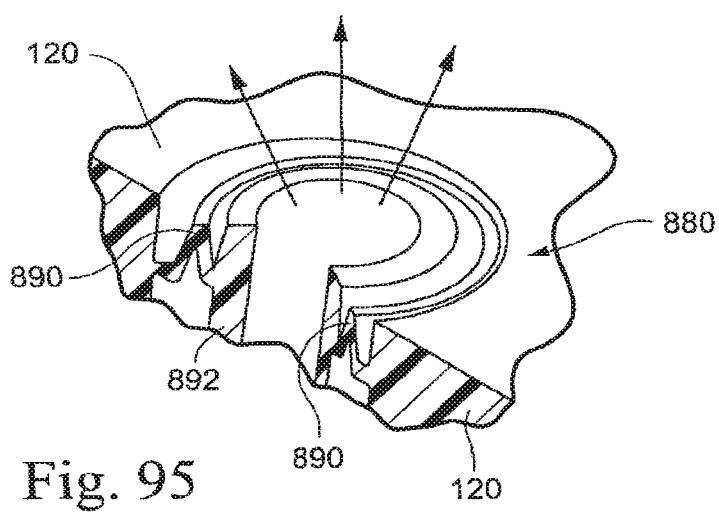
FIGS. 95 and 96 schematically depict a tube connection system according to a sample embodiment of the invention.
Figure 96:
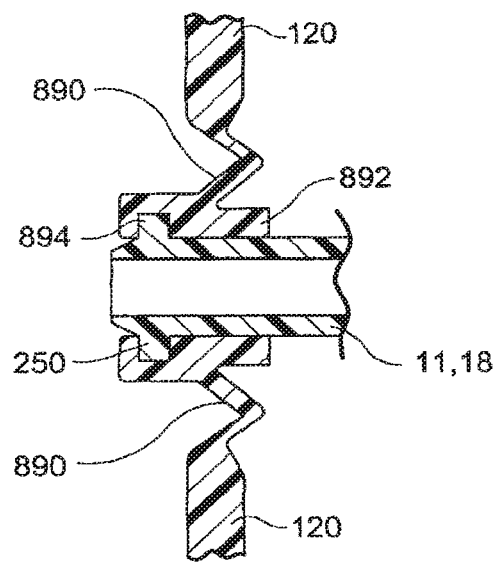

Referring to FIGS. 95 and 96, the elbow and/or tube connectors 880 formed on the mask/cushion comprise thin walls 890 that are configured to decouple tube dragging forces applied to the elbow and/or air delivery tube 11 that may be connected to the mask/cushion. The thin walls 890 are flexible and support a cylindrical support 892 that is configured to receive the end of an elbow or the end of a delivery tube. The thin walls 890 may have, for example, a V-shaped configuration to absorb tube drag forces or headgear forces without transmitting those forces to the mask/cushion.

The mask/cushion may be subject to forces, for example, by stretching of the headgear, and the thin walls 890 are stretched to minimize distortion of the cushion seal. Due to equilibrium of forces, the thin walls 890 may not absorb forces to the mask/cushion, but may delay the forces by stretching. The mask/cushion may be formed to resist headgear forces as discussed in more detail below. The stretching of the thin walls 890 may also be useful in assisting finer adjustment of the headgear and fitting of the mask/cushion to the patient.

As shown in FIG. 96, seals 250 may be provided on the outer diameter of the elbow or air delivery tube to form a seal between the elbow or air delivery tube and the connectors 880 of the mask/cushion. The seals may be formed of, for example, silicone. The cylindrical support 892 may include a recess 894 configured to receive the seals 250 upon insertion of the elbow or delivery tube into the connector(s). It should be appreciated that the seals 250 may be provided separately to the elbow or the delivery conduit, or the seals may be integrally formed with the end of the elbow or the delivery conduit.

In general, infant or neo-natal patients require less pressure for effective therapy. For example, an infant or neo-natal patient may have effective CPAP therapy using a pressure of 4 cm $H_2O$. As the treatment pressure for children may be less than for adults, the use of a 22 mm tube, as is used in the treatment of adult patients, need not be used in the treatment of children. However, many available flow generators have fittings for 22 mm tubes for the treatment of adult patients.

The treatment of children and/or neo-natal patients also requires less flow than for adult patients. For example, the treatment of an adult may require a flow of 70 l/min, or 30 l/min for vent flow. In a child, or neo-natal patient, a flow of 12-15 l/min may be appropriate. The vent flow for the treatment of a child or neo-natal patient may be the same as for an adult or it may be less.

As the required pressure and flow for effective treatment or children and/or neo-natal patients is less than for adults, the tubing required for treatment of children or neo-natal patients may be of a reduced diameter, e.g., of a diameter smaller than 22 mm. For example, the tubing from the flow generator to the mask for a child or a neo-natal patient may be staged as described previously herein. For example, a 22 mm diameter tube may be connected to the flow generator and a 7 mm diameter tube may be connected to the mask. A 15 mm tube may be provided between the 22 mm tube and the 7 mm tube. It should also be appreciated that the use of smaller diameter tubing reduces the weight of the respiratory system. For example, the 22 mm diameter tube may be clamped to a structure, such as a table or bed, to reduce the tube drag on the mask. A 15 mm diameter intermediate tube may have a length of, for example, 10 cm to 1 m, for example, 60 cm. A 7 mm diameter tube for connection to the mask may have a length of 20 cm to 1 m, for example, 30 cm.

Mask/Cushion and Headgear System Decoupler

Figure 97:
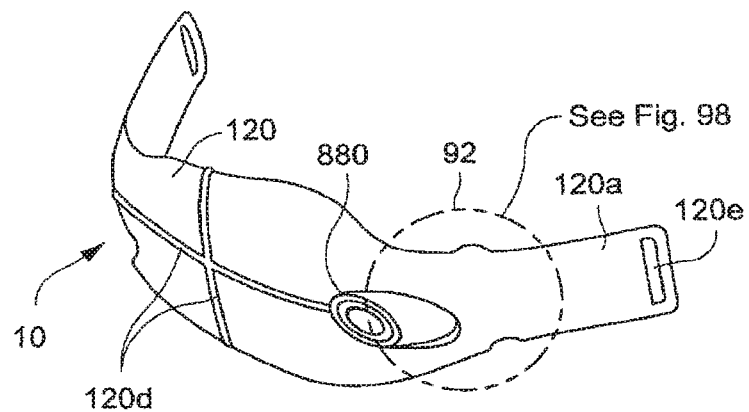
FIG. 97 schematically depicts a mask according to another sample embodiment of the invention.
Figure 98:
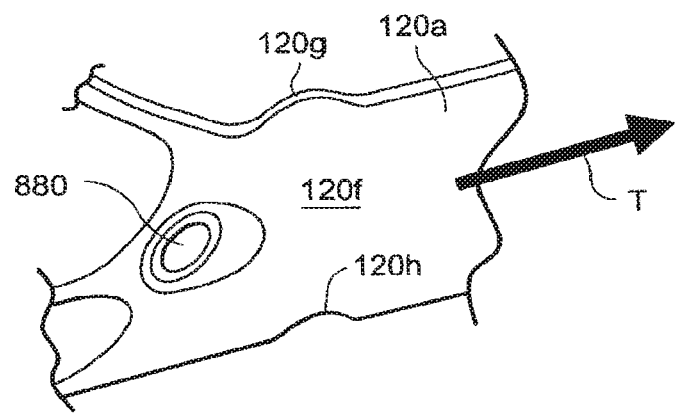
FIG. 98 schematically depicts details of FIG. 97.

Referring to FIGS. 97 and 98, the one piece mask/cushion may comprise a decoupler 120f that is configured to decouple tension T applied to the ends 120a of the mask/cushion from the portion of the mask/cushion that is in sealing engagement with the patient's face to reduce, or minimize, distortion of the cushion seal. The decoupler 120f may comprise a projection 120g on one side of the end 120a of the cushion and a corresponding notch 120h on the opposite side of the end 120a of the cushion 120. Although the projection 120g is shown in FIG. 98 on the top of the end 120a and the notch or recess 120h is shown on the bottom of the end 120a, it should be appreciated that the projection may be on the bottom and the notch or recess on the top. It should also be appreciated that although one projection and one corresponding notch or recess is shown in FIG. 98, the decoupler may comprise plural projections and plural corresponding notches or recesses.

Due to the equilibrium of forces applied by the headgear system, the decoupler may not absorb forces applied to the mask/cushion. The mask/cushion may then be configured to resist forces applied by the headgear. The decoupler may delay forces applied to the mask/cushion by stretching. The stretching of the decoupler may also be useful in assisting finer adjustments of the headgear system and attaching and sealing of the mask/cushion to the face of the patient.

ALTERNATE EMBODIMENTS OF THE INVENTION

It should be appreciated that the interfacing structure may have other interfacing arrangements, e.g., over-the-nose interface, full-face, nasal prongs, pillows, or cannulae, or a combination of a mouth sealing structure in combination with nasal prongs, pillows, or cannulae.

The mask may be configured so that no hard material is exposed. For example, the support structure and or the rigid members may be covered in a material that is softer than the material used to form the support structure and/or the rigid members. In the sample embodiments discussed above in which the cushion and the support structure are formed as a single piece, e.g. by co-molding, the support structure may be formed to be more rigid than the cushion, but less rigid than currently used mask frames or shells made of rigid plastic material.

Prior art masks for treating children are deficient in one or more of the following areas:

Size/bulk

Infants may lie on their stomachs when they sleep. The configuration of prior art masks are too bulky on the infant's face or forehead to readily allow for this. Other mask designs are too flexible and might collapse (e.g. Sullivan—WO 01/32250).

It is desirable for parents to have a clear view of their child. Some prior art masks do not allow for this (e.g. mask covers too much of child's face).

It is desirable for clinicians and carers to have a clear view of the nares to ensure that they are not obstructed.

Hard/rigid components (This may cause pressure sores and can be perceived negatively by patients/clinicians/parents).

Not designed to be fitted by a third party (e.g. clips are difficult to operate).

Unlike the ResMed Infant Bubble mask, the Sullivan/Wilkie (WO/2001/032250) infant mask, and the infant mask described in WO 2007/045023, an infant mask in accordance with the present invention preferably does not include a forehead support, or a forehead contacting portion.

Another aspect of the ResMed Infant Bubble mask, the Sullivan/Wilkie (WO/2001/032250) infant mask, and the infant mask described in WO 2007/045023, is that they all include an air delivery tube on the front of the mask, or for feeding air between the eyes. Preferably in accordance with the present invention, air is supplied on either side and below the nose. In this way, the overall height of the preferred mask system is reduced, making it more comfortable for the patient should they be sleeping face down, or rolling over. See for example FIG. 7 which shows how in a side view, the air delivery tubes do not lead to a greater height projecting out from the face than the reinforcing element of the frame.

Compared to the masks described in WO2007/045023, masks in accordance with the preferred forms of the present invention provide a structure which provides improved resistance to collapse, for example due to the patient rolling over or sleeping face down.

Compared to the ResMed Infant Swift nasal pillows mask, which is described in WO2007/041786, preferred masks according to the present invention are less prone to jetting, which is a decrease in breathing comfort where a cold, frictional or burning sensation may be felt inside the nose from air rushing through the nose, particularly upon inhalation and higher pressures when the air travels at higher speeds through the nose The preferred masks may also provide reduced likelihood of causing trauma to the nasal septum and increased reliability of fitting to the small nares of an infant.

Preferred masks according to the invention have a different sealing vectors to those of the ResMed Infant Swift nasal pillows mask, and provide load back onto the patient's face, which can withstand greater forces.

The masks according to the invention may also exhibit reduced flow impedence, as scaling down of an adult mask as done in some prior art devices may result in the scaled down area of nasal pillows may be too small in diameter to allow for sufficient flow.

Another aspect of a mask in accordance with the present invention is that the cushion does not need to be glued or otherwise adhered to the face.

In one form of the invention, the yokes are not formed as separate pieces but constructed, for example moulded, as part of the frame.

While the invention has been described in connection with what are presently considered to be the most practical and desirable embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A patient interface configured to deliver pressurized breathable gas to a patient's airways, the patient interface comprising:
   a flexible cushion forming at least a portion of a plenum chamber and configured to sealingly engage a portion of the patient's face including a portion of the patient's nose and/or a portion adjacent the patient's nose;
   a support structure that is more rigid than the flexible cushion and is pivotably attached to the flexible cushion; and
   at least one receptacle on a lateral side of the flexible cushion, each receptacle being in direct communication with an interior of the plenum chamber and having a lateral opening configured to receive an air delivery tube,
   wherein the at least one receptacle is more flexible at the lateral opening than the support structure, and
   wherein the flexible cushion is secured to the support structure on a lateral side of the support structure at the at least one receptacle.

2. A patient interface assembly comprising:
   the patient interface of claim 1; and
   headgear configured to support the patient interface on the patient's head,
   wherein the headgear comprises a forward finger, a rear end of the forward finger branching into an upwardly and rearwardly extending upper rearward finger, and a downwardly and rearwardly extending lower rearward finger.

3. The patient interface assembly of claim 2, wherein at least a portion of the headgear is associated with a rigidizer.

4. The patient interface assembly of claim 3, wherein the rigidizer comprises the forward finger, the upper rearward finger, and the lower rearward finger.

5. The patient interface of claim 2, wherein the upper rearward finger branches into a plurality of additional fingers, each being associated with a headgear strap.

6. The patient interface assembly of claim 2, wherein the lower rearward finger comprises a headgear strap connection point, and the forward finger comprises a patient interface connection point.

7. The patient interface assembly of claim 2, further comprising the air delivery tube received by the receptacle.

8. The patient interface of claim 1, wherein the support structure comprises a projection configured to engage one of a plurality of recesses in the flexible cushion to select a position of the flexible cushion with respect to the support structure.

9. The patient interface of claim 8, wherein the plurality of recesses are spaced equidistantly from a pivot axis of the flexible cushion.

10. The patient interface of claim 1, wherein a wall of the flexible cushion separates the support structure from an interior of the plenum chamber.

11. The patient interface of claim 1, wherein the support structure is configured to connect to headgear.

12. The patient interface of claim 1, wherein the support structure is detachable from the flexible cushion.

13. The patient interface of claim 1, wherein each of the at least one receptacle is received within a respective opening in the support structure.

14. The patient interface of claim 1, further comprising a gas washout vent that is equidistant from each of the at least one receptacle.

15. The patient interface of claim 1, wherein the flexible cushion is configured to pivot around a central longitudinal axis of the at least one receptacle.

16. A patient interface configured to deliver pressurized breathable gas to a patient's airways, the patient interface comprising:
a flexible cushion with a rear aperture configured to receive the patient's nose, a tube connection portion of the flexible cushion having a lateral opening configured to connect to an air delivery tube;
a plenum chamber formed by the flexible cushion;
a gas washout vent on a front wall of the flexible cushion that is opposite the rear aperture;
a support structure attached to the flexible cushion on a lateral side of the flexible cushion at the tube connection portion, the support structure being more rigid than the tube connection portion of the flexible cushion at the lateral opening and being fluidly isolated from the interior of the plenum chamber and from the gas washout vent, the tube connection portion being movable relative to the support structure; and
a pair of headgear connectors on the support structure.

17. The patient interface of claim 16, wherein the support structure comprises a pair of lateral portions connected by a bridge.

18. The patient interface of claim 17, wherein the gas washout vent is located between the pair of lateral portions.

19. The patient interface of claim 16, wherein the tube connection portion is arranged to at least partially decouple movement of the air delivery tube from the flexible cushion.

20. The patient interface of claim 19, wherein the tube connection portion of the flexible cushion is rotatable relative to the support structure.

21. The patient interface of claim 16, wherein the flexible cushion is pivotably supported on the support structure.

22. The patient interface of claim 21, wherein the support structure comprises a slot and the flexible cushion comprises an adjustment member extending through the slot and configured to be engagable by fingers for pivoting the flexible cushion relative to the support structure.

23. The patient interface of claim 22, wherein the slot comprises a plurality of indentations configured to frictionally engage the adjustment member.

24. A patient interface assembly comprising:
the patient interface of claim 16; and
headgear configured to support the patient interface on the patient's head,
wherein the headgear comprises a forward finger, a rear end of the forward finger branching into an upwardly and rearwardly extending upper rearward finger, and a downwardly and rearwardly extending lower rearward finger.

25. The patient interface assembly of claim 24, wherein at least a portion of the headgear is associated with a rigidizer.

26. The patient interface assembly of claim 25, wherein the rigidizer comprises the forward finger, the upper rearward finger, and the lower rearward finger.

27. The patient interface assembly of claim 24, wherein each of the pair of headgear connectors comprises multiple connection points so that the headgear is repositionable relative to the support structure.

28. The patient interface assembly of claim 24, comprising the air delivery tube that is connectable to the flexible cushion.

29. The patient interface assembly of claim 24, wherein the upper rearward finger branches into a plurality of additional fingers, each being associated with a headgear strap.

30. The patient interface assembly of claim 24, wherein the lower rearward finger comprises a headgear strap connection point, and the forward finger comprises a patient interface connection point.

31. The patient interface of claim 16, wherein the gas washout vent has plurality of vents.

32. The patient interface of claim 16, wherein the support structure surrounds tube connection portion.

33. The patient interface of claim 16, wherein support structure is removable from the flexible cushion.

34. The patient interface of claim 16, wherein the entirety of the plenum chamber is formed by the flexible cushion.

35. The patient interface of claim 16, wherein the flexible cushion comprises more than one tube connection portion.

36. The patient interface of claim 16, wherein the patient interface is a nasal mask.

37. The patient interface of claim 16, wherein the gas washout vent has plurality of vents,
wherein the support structure surrounds tube connection portion,
wherein the support structure is removable from the flexible cushion,
wherein the entirety of the plenum chamber is formed by the flexible cushion,
wherein the flexible cushion comprises more than one tube connection portion,
wherein support structure comprises a pair of lateral portions connected by a bridge,
wherein the gas washout vent is located between the pair of lateral portions, and
wherein the patient interface is a nasal mask.

38. The patient interface of claim 16, wherein the tube connection portion of the flexible cushion is configured to receive the air delivery tube or an elbow.

39. A patient interface configured to deliver pressurized breathable gas to a patient's airways, the patient interface comprising:
a flexible cushion forming at least a portion of a plenum chamber and configured to sealingly engage a portion of the patient's face including a portion of the patient's nose and/or a portion adjacent the patient's nose;
a support structure that is more rigid than the flexible cushion and is attached to the flexible cushion; and
at least one receptacle on a lateral side of the flexible cushion, each of the at least one receptacle being in direct communication with an interior of the plenum chamber and having a lateral opening configured to receive an air delivery tube,
wherein the at least one receptacle is more flexible than the support structure at lateral opening and is arranged to decouple movement of the air delivery tube from the flexible cushion, and
wherein the flexible cushion is secured to the support structure on a lateral side of the support structure at the at least one receptacle.

40. The patient interface of claim 39, wherein the at least one receptacle is configured to allow at least a partial rotation of the flexible cushion with respect to an air delivery tube.

41. The patient interface of claim 39, wherein the at least one receptacle comprises a pair of tube connection portions located on opposite sides of the patient interface.

42. The patient interface of claim 39, wherein the at least one receptacle is configured to extend through at least one opening in the support structure.

\* \* \* \* \*